(12) United States Patent
Mollere et al.

(10) Patent No.: US 8,926,598 B2
(45) Date of Patent: Jan. 6, 2015

(54) SURGICAL INSTRUMENTS WITH ARTICULATABLE AND ROTATABLE END EFFECTOR

(75) Inventors: Rebecca J. Mollere, Loveland, OH (US); Charles J. Scheib, Loveland, OH (US); Chad P. Boudreaux, Cincinnati, OH (US); Michael J. Vendely, Lebanon, OH (US); Aron O. Zingman, Cambridge, MA (US); Jeffrey S. Swayze, Hamilton, OH (US); Barry C. Worrell, Centerville, OH (US); Janna B. Volz, Fort Thomas, KY (US); John C. Schuckmann, Cincinnati, OH (US); Megan A. O'Connor, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 396 days.

(21) Appl. No.: 13/048,579

(22) Filed: Mar. 15, 2011

(65) Prior Publication Data

US 2012/0239009 A1 Sep. 20, 2012

(51) Int. Cl.
*A61B 17/00* (2006.01)
*A61B 17/072* (2006.01)
*A61B 17/29* (2006.01)

(52) U.S. Cl.
CPC ..... *A61B 17/07207* (2013.01); *A61B 2017/291* (2013.01); *A61B 2017/2927* (2013.01); *A61B 2017/2929* (2013.01); *A61B 2017/293* (2013.01); *A61B 2017/00367* (2013.01)
USPC .......................... 606/1; 227/175.1; 227/175.2

(58) Field of Classification Search
CPC ......... A61B 17/04; A61B 17/10; A61B 17/00
USPC ........ 606/1–10; 227/153, 175.1, 176.1, 177.1
See application file for complete search history.

(56) References Cited

U.S. PATENT DOCUMENTS

| | | |
|---|---|---|
| 2,853,074 A | 9/1958 | Olson |
| 4,619,262 A | 10/1986 | Taylor |
| 4,844,068 A | 7/1989 | Arata et al. |
| 5,405,072 A | 4/1995 | Zlock et al. |
| 5,405,344 A | 4/1995 | Williamson et al. |
| 5,413,272 A | 5/1995 | Green et al. |
| 5,441,494 A | 8/1995 | Ortiz |
| 5,480,089 A | 1/1996 | Blewett |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

U.S. Appl. No. 13/048,566, filed Mar. 15, 2011.

(Continued)

*Primary Examiner* — William Thomson
*Assistant Examiner* — Victor Shapiro

(57) ABSTRACT

Hand-held surgical instruments that have and end effector attached to an elongate shaft are disclosed. The end effector is articulatable and rotatable relative to the shaft by a nozzle arrangement supported by a handle from which the elongate shaft extends. In various embodiments, the nozzle is operable by the same hand that is used to support the handle.

22 Claims, 35 Drawing Sheets

(56) References Cited

U.S. PATENT DOCUMENTS

| | | |
|---|---|---|
| 5,487,499 A | 1/1996 | Sorrentino et al. |
| 5,497,933 A | 3/1996 | DeFonzo et al. |
| 5,505,363 A | 4/1996 | Green et al. |
| 5,520,678 A | 5/1996 | Heckele et al. |
| 5,529,235 A | 6/1996 | Boiarski et al. |
| 5,535,934 A | 7/1996 | Boiarski et al. |
| 5,558,665 A | 9/1996 | Kieturakis |
| 5,562,241 A | 10/1996 | Knodel et al. |
| 5,564,615 A | 10/1996 | Bishop et al. |
| 5,577,654 A | 11/1996 | Bishop |
| 5,588,579 A | 12/1996 | Schnut et al. |
| 5,601,224 A | 2/1997 | Bishop et al. |
| 5,607,094 A | 3/1997 | Clark et al. |
| 5,607,095 A * | 3/1997 | Smith et al. ............ 227/177.1 |
| 5,628,446 A | 5/1997 | Geiste et al. |
| 5,628,743 A | 5/1997 | Cimino |
| 5,630,539 A | 5/1997 | Plyley et al. |
| 5,639,008 A | 6/1997 | Gallagher et al. |
| 5,651,491 A | 7/1997 | Heaton et al. |
| 5,653,373 A | 8/1997 | Green et al. |
| 5,662,258 A | 9/1997 | Knodel et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,692,668 A | 12/1997 | Schulze et al. |
| 5,693,042 A | 12/1997 | Boiarski et al. |
| 5,704,534 A | 1/1998 | Huitema et al. |
| 5,711,472 A | 1/1998 | Bryan |
| 5,715,987 A | 2/1998 | Kelley et al. |
| 5,732,871 A | 3/1998 | Clark et al. |
| 5,792,135 A | 8/1998 | Madhani et al. |
| 5,797,536 A | 8/1998 | Smith et al. |
| 5,807,376 A | 9/1998 | Viola et al. |
| 5,807,378 A | 9/1998 | Jensen et al. |
| 5,817,084 A | 10/1998 | Jensen |
| 5,829,662 A | 11/1998 | Allen et al. |
| 5,836,503 A | 11/1998 | Ehrenfels et al. |
| 5,839,639 A | 11/1998 | Sauer et al. |
| 5,855,311 A * | 1/1999 | Hamblin et al. ......... 227/176.1 |
| 5,941,442 A | 8/1999 | Geiste et al. |
| 6,159,200 A | 12/2000 | Verdura et al. |
| 6,162,208 A | 12/2000 | Hipps |
| 6,231,565 B1 | 5/2001 | Tovey et al. |
| 6,241,139 B1 | 6/2001 | Milliman et al. |
| 6,250,532 B1 | 6/2001 | Green et al. |
| 6,488,196 B1 | 12/2002 | Fenton, Jr. |
| 6,605,078 B2 | 8/2003 | Adams |
| 6,666,854 B1 | 12/2003 | Lange |
| 6,699,235 B2 | 3/2004 | Wallace et al. |
| 6,722,552 B2 | 4/2004 | Fenton, Jr. |
| 6,723,087 B2 | 4/2004 | O'Neill et al. |
| 6,755,338 B2 * | 6/2004 | Hahnen et al. .......... 227/175.1 |
| 6,786,896 B1 | 9/2004 | Madani et al. |
| 6,793,652 B1 | 9/2004 | Whitman et al. |
| 6,830,174 B2 | 12/2004 | Hillstead et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,866,178 B2 | 3/2005 | Adams et al. |
| 6,874,669 B2 | 4/2005 | Adams et al. |
| 6,936,042 B2 | 8/2005 | Wallace et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,964,363 B2 | 11/2005 | Wales et al. |
| 7,000,818 B2 | 2/2006 | Shelton, IV et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,122,028 B2 | 10/2006 | Looper et al. |
| 7,140,527 B2 | 11/2006 | Ehrenfels et al. |
| 7,143,926 B2 | 12/2006 | Shelton, IV et al. |
| 7,159,750 B2 | 1/2007 | Racenet et al. |
| 7,182,239 B1 | 2/2007 | Myers |
| 7,237,708 B1 | 7/2007 | Guy et al. |
| 7,241,288 B2 | 7/2007 | Braun |
| 7,246,734 B2 | 7/2007 | Shelton, IV |
| 7,252,660 B2 | 8/2007 | Kunz |
| 7,303,106 B2 | 12/2007 | Milliman et al. |
| 7,328,828 B2 | 2/2008 | Ortiz et al. |
| 7,334,717 B2 | 2/2008 | Rethy et al. |
| 7,334,718 B2 | 2/2008 | McAlister et al. |
| 7,354,447 B2 | 4/2008 | Shelton, IV et al. |
| 7,364,060 B2 | 4/2008 | Milliman |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,481,347 B2 | 1/2009 | Roy |
| 7,490,749 B2 | 2/2009 | Schall et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,549,563 B2 | 6/2009 | Mather et al. |
| 7,549,564 B2 | 6/2009 | Boudreaux |
| 7,556,185 B2 | 7/2009 | Viola |
| 7,559,450 B2 | 7/2009 | Wales et al. |
| 7,559,452 B2 | 7/2009 | Wales et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,624,902 B2 | 12/2009 | Marczyk et al. |
| 7,631,793 B2 | 12/2009 | Rethy et al. |
| 7,637,409 B2 * | 12/2009 | Marczyk ................... 227/175.1 |
| 7,644,848 B2 | 1/2010 | Swayze et al. |
| 7,658,311 B2 | 2/2010 | Boudreaux |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,691,098 B2 | 4/2010 | Wallace et al. |
| 7,699,204 B2 | 4/2010 | Viola |
| 7,703,653 B2 | 4/2010 | Shah et al. |
| 7,708,180 B2 | 5/2010 | Murray et al. |
| 7,717,312 B2 | 5/2010 | Beetel |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |

(56) References Cited

U.S. PATENT DOCUMENTS

| | | |
|---|---|---|
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,780,054 B2 | 8/2010 | Wales |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,803,151 B2 | 9/2010 | Whitman |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,080 B2 | 11/2010 | Schwemberger |
| 7,845,533 B2 | 12/2010 | Marczyk et al. |
| 7,845,537 B2 | 12/2010 | Shelton, IV et al. |
| 7,846,149 B2 | 12/2010 | Jankowski |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,221 B2 | 3/2011 | Viola et al. |
| 7,913,891 B2 | 3/2011 | Doll et al. |
| 7,918,376 B1 * | 4/2011 | Knodel et al. ............. 227/175.1 |
| 7,918,377 B2 | 4/2011 | Measamer et al. |
| 7,922,061 B2 | 4/2011 | Shelton, IV et al. |
| 7,934,630 B2 | 5/2011 | Shelton, IV et al. |
| 7,950,560 B2 | 5/2011 | Zemlok et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 7,966,799 B2 | 6/2011 | Morgan et al. |
| 7,967,180 B2 | 6/2011 | Scirica |
| 7,980,443 B2 | 7/2011 | Scheib et al. |
| 8,011,551 B2 | 9/2011 | Marczyk et al. |
| 8,020,742 B2 * | 9/2011 | Marczyk ................... 227/175.1 |
| 8,020,743 B2 | 9/2011 | Shelton, IV |
| 8,028,883 B2 | 10/2011 | Stopek |
| 8,056,787 B2 | 11/2011 | Boudreaux et al. |
| 8,066,167 B2 | 11/2011 | Measamer et al. |
| D650,074 S | 12/2011 | Hunt et al. |
| 8,083,119 B2 | 12/2011 | Prommersberger |
| 8,083,120 B2 | 12/2011 | Shelton, IV et al. |
| 8,241,271 B2 | 8/2012 | Millman et al. |
| 8,256,654 B2 | 9/2012 | Bettuchi et al. |
| 8,348,127 B2 | 1/2013 | Marczyk |
| 8,360,296 B2 | 1/2013 | Zingman |
| 8,393,514 B2 | 3/2013 | Shelton, IV et al. |
| 2004/0111081 A1 | 6/2004 | Whitman et al. |
| 2004/0147909 A1 | 7/2004 | Johnston et al. |
| 2004/0173659 A1 | 9/2004 | Green et al. |
| 2004/0254566 A1 | 12/2004 | Plicchi et al. |
| 2005/0103819 A1 | 5/2005 | Racenet et al. |
| 2005/0131390 A1 | 6/2005 | Heinrich et al. |
| 2005/0274768 A1 | 12/2005 | Cummins et al. |
| 2006/0020258 A1 | 1/2006 | Strauss et al. |
| 2006/0049229 A1 | 3/2006 | Milliman et al. |
| 2006/0226196 A1 | 10/2006 | Hueil et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0055219 A1 | 3/2007 | Whitman et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0135803 A1 | 6/2007 | Belson |
| 2007/0158385 A1 * | 7/2007 | Hueil et al. ................. 227/175.1 |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0239028 A1 | 10/2007 | Houser et al. |
| 2007/0246505 A1 | 10/2007 | Pace-Floridia et al. |
| 2007/0270784 A1 | 11/2007 | Smith et al. |
| 2007/0295780 A1 | 12/2007 | Shelton et al. |
| 2007/0299427 A1 | 12/2007 | Yeung et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082125 A1 | 4/2008 | Murray et al. |
| 2008/0082126 A1 | 4/2008 | Murray et al. |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0251568 A1 | 10/2008 | Zemlok et al. |
| 2008/0251569 A1 | 10/2008 | Smith et al. |
| 2008/0283570 A1 | 11/2008 | Boyden et al. |
| 2008/0296346 A1 | 12/2008 | Shelton, IV et al. |
| 2008/0300580 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0314956 A1 * | 12/2008 | Boudreaux ................. 227/175.2 |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0078736 A1 | 3/2009 | Van Lue |
| 2009/0108048 A1 | 4/2009 | Zemlok et al. |
| 2009/0149871 A9 | 6/2009 | Kagan et al. |
| 2009/0198272 A1 | 8/2009 | Kerver et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209990 A1 | 8/2009 | Yates et al. |
| 2009/0242610 A1 | 10/2009 | Shelton, IV et al. |
| 2010/0032470 A1 | 2/2010 | Hess et al. |
| 2010/0069942 A1 | 3/2010 | Shelton, IV |
| 2010/0076474 A1 | 3/2010 | Yates et al. |

(56) References Cited

U.S. PATENT DOCUMENTS

| | | |
|---|---|---|
| 2010/0076475 A1 | 3/2010 | Yates et al. |
| 2010/0089970 A1 | 4/2010 | Smith et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0243709 A1 | 9/2010 | Hess et al. |
| 2010/0258611 A1 | 10/2010 | Smith et al. |
| 2010/0264193 A1 | 10/2010 | Huang et al. |
| 2010/0264194 A1 | 10/2010 | Huang et al. |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0036890 A1 | 2/2011 | Ma |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174861 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0210156 A1 | 9/2011 | Smith et al. |
| 2011/0226837 A1 | 9/2011 | Baxter, III et al. |
| 2011/0233258 A1 | 9/2011 | Boudreaux |
| 2011/0253766 A1 | 10/2011 | Baxter, III et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0290857 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |

(56) References Cited

U.S. PATENT DOCUMENTS

| | | |
|---|---|---|
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0234900 A1 | 9/2012 | Swayze |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239010 A1 | 9/2012 | Shelton, IV et al. |
| 2012/0239012 A1 | 9/2012 | Laurent et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0273551 A1 | 11/2012 | Shelton, IV et al. |
| 2012/0283707 A1 | 11/2012 | Giordano et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2013/0012931 A1 | 1/2013 | Spivey et al. |
| 2013/0012957 A1 | 1/2013 | Shelton, IV et al. |
| 2013/0018361 A1 | 1/2013 | Bryant |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0041371 A1 | 2/2013 | Yates et al. |
| 2013/0056518 A1 | 3/2013 | Swensgard |
| 2013/0056520 A1 | 3/2013 | Swensgard |
| 2013/0056521 A1 | 3/2013 | Swensgard |
| 2013/0056522 A1 | 3/2013 | Swensgard |
| 2013/0075443 A1 | 3/2013 | Giordano et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0105551 A1 | 5/2013 | Zingman |

FOREIGN PATENT DOCUMENTS

| | | |
|---|---|---|
| CA | 2514274 A1 | 1/2006 |
| CN | 2488482 Y | 5/2002 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 81 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0832605 B1 | 6/2000 |

(56) References Cited

FOREIGN PATENT DOCUMENTS

| | | |
|---|---|---|
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1632191 A2 | 3/2006 |
| EP | 1065981 B1 | 5/2006 |
| EP | 1082944 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1857057 A2 | 11/2007 |
| EP | 1402821 B1 | 12/2007 |
| EP | 1872727 A1 | 1/2008 |
| EP | 1897502 A1 | 3/2008 |
| EP | 1908417 A2 | 4/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1990014 A2 | 11/2008 |
| EP | 1693008 B1 | 12/2008 |
| EP | 1759640 B1 | 12/2008 |
| EP | 2000102 A2 | 12/2008 |
| EP | 2005894 A2 | 12/2008 |
| EP | 2008595 A2 | 12/2008 |
| EP | 1736104 B1 | 3/2009 |
| EP | 1749486 B1 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 1550409 A1 | 6/2009 |
| EP | 1550413 B1 | 6/2009 |
| EP | 1745748 B1 | 8/2009 |
| EP | 2090237 A1 | 8/2009 |
| EP | 2090241 A1 | 8/2009 |

(56) References Cited

FOREIGN PATENT DOCUMENTS

| | | |
|---|---|---|
| EP | 2090244 A2 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 1607050 B1 | 12/2009 |
| EP | 1815804 B1 | 12/2009 |
| EP | 1566150 B1 | 4/2010 |
| EP | 1813206 B1 | 4/2010 |
| EP | 1769754 B1 | 6/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 1627605 B1 | 12/2010 |
| EP | 2286738 A2 | 2/2011 |
| EP | 1690502 B1 | 3/2011 |
| EP | 1769755 B1 | 4/2011 |
| EP | 1813205 B1 | 6/2011 |
| EP | 2090243 B1 | 6/2011 |
| EP | 2329773 A1 | 6/2011 |
| EP | 1908414 B1 | 11/2011 |
| EP | 1785102 B1 | 1/2012 |
| EP | 2090253 B1 | 3/2012 |
| EP | 2005895 B1 | 8/2012 |
| EP | 2090248 B1 | 8/2012 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | 50-33988 U | 4/1975 |
| JP | S 58500053 A | 1/1983 |
| JP | 61-98249 A | 5/1986 |
| JP | S 61502036 A | 9/1986 |
| JP | 63-203149 | 8/1988 |
| JP | 3-12126 A | 1/1991 |
| JP | 5-212039 A | 8/1993 |
| JP | 6007357 A | 1/1994 |
| JP | H 6-30945 A | 2/1994 |
| JP | H 6-121798 A | 5/1994 |
| JP | 7051273 A | 2/1995 |
| JP | 7-124166 A | 5/1995 |
| JP | 7-255735 A | 10/1995 |
| JP | 8-33642 A | 2/1996 |
| JP | 8033641 A | 2/1996 |
| JP | 8-164141 A | 6/1996 |
| JP | 8229050 A | 9/1996 |
| JP | 2000-14632 | 1/2000 |
| JP | 2000033071 A | 2/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001286477 A | 10/2001 |
| JP | 2002143078 A | 5/2002 |
| JP | 2002369820 A | 12/2002 |
| JP | 2003-500153 A | 1/2003 |
| JP | 2003-521301 A | 7/2003 |
| JP | 2004-329624 A | 11/2004 |
| JP | 2004-344663 | 12/2004 |
| JP | 2005-028147 A | 2/2005 |
| JP | 2005-028149 A | 2/2005 |
| JP | 2005-505309 A | 2/2005 |
| JP | 2005505322 T | 2/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2006-034975 A | 2/2006 |
| JP | 2006-218297 A | 8/2006 |
| JP | 2006-281405 A | 10/2006 |
| JP | 2007-117725 A | 5/2007 |
| JP | 2008-283459 A | 11/2008 |
| RU | 2008830 C1 | 3/1994 |
| RU | 2141279 C1 | 11/1999 |
| RU | 2187249 C2 | 8/2002 |
| RU | 2225170 C2 | 3/2004 |
| SU | 189517 A | 1/1967 |
| SU | 328636 A | 9/1972 |
| SU | 886900 A1 | 12/1981 |
| SU | 1009439 A | 4/1983 |
| SU | 1333319 A2 | 8/1987 |
| SU | 1377053 A1 | 2/1988 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/22378 A1 | 10/1994 |
| WO | WO 94/23659 A1 | 10/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |

(56) References Cited

FOREIGN PATENT DOCUMENTS

| | | |
|---|---|---|
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A2 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A2 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |

(56) References Cited

FOREIGN PATENT DOCUMENTS

| | | |
|---|---|---|
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/109125 A1 | 9/2008 |
| WO | WO 2008/124748 A1 | 10/2008 |
| WO | WO 2009/137761 A2 | 11/2009 |
| WO | WO 2010/030434 A1 | 3/2010 |
| WO | WO 2010/063795 A1 | 6/2010 |
| WO | WO 2010/098871 A2 | 9/2010 |
| WO | WO 2012/021671 A1 | 2/2012 |
| WO | WO 2012/044844 A2 | 4/2012 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property—Durometer Hardness," (Published Aug. 2000).

ASTM procedure D2240-05, "Standard Test Method for Rubber Property—Durometer Hardness," (Published Apr. 2010).

International Search Report, PCT/US2012/028925, dated Feb. 7, 2013 (8 pages).

* cited by examiner

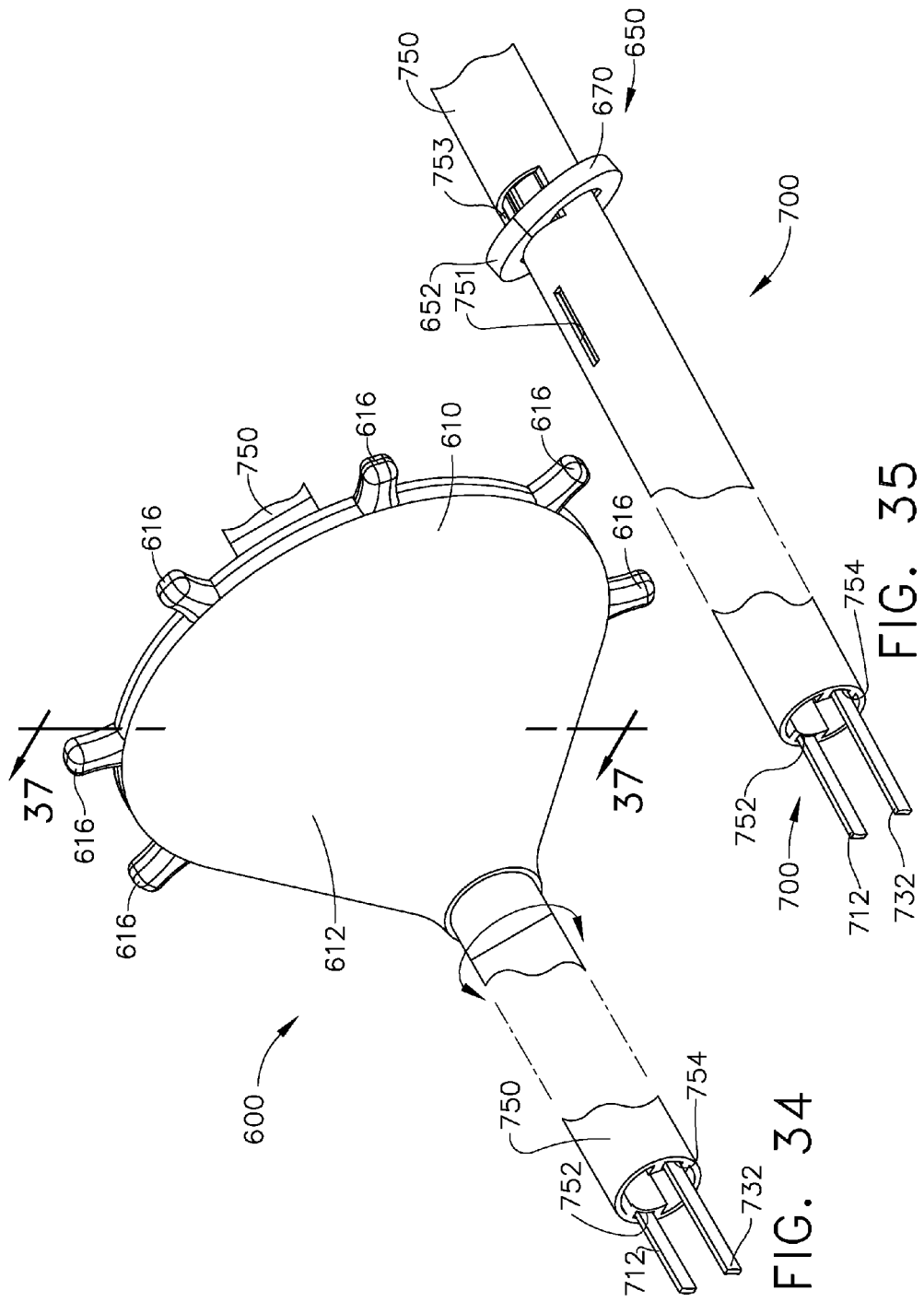

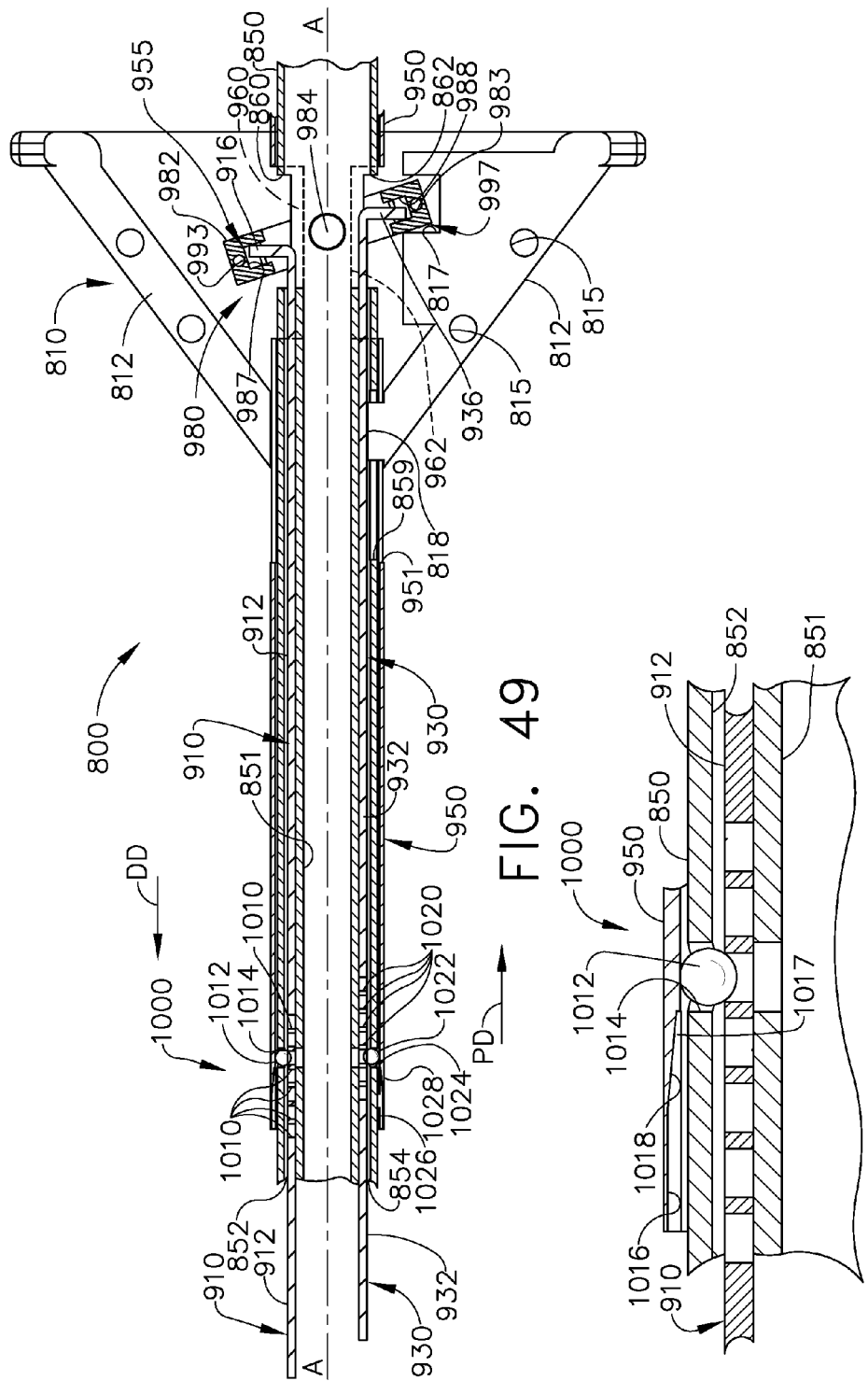

SURGICAL INSTRUMENTS WITH ARTICULATABLE AND ROTATABLE END EFFECTOR

BACKGROUND

1. Technical Field

The present invention relates to surgical instruments and, in various embodiments, to minimally invasive surgical instruments having an articulating end effector.

2. Background

Endoscopic and other minimally invasive surgical instruments typically include an end effector positioned at the distal end of an elongate shaft and a handle at the proximal end of the elongate shaft allowing a clinician to manipulate the end effector. In use, the end effector is provided to a surgical site through a cannula of a trocar. At the surgical site, the end effector engages tissue in any number of ways to achieve a diagnostic or therapeutic effect. Endoscopic surgical instruments are often preferred over traditional open surgical instruments because they require smaller incisions that generally heal with less post-operative recovery time than traditional open surgery incisions. Because of this and other benefits of endoscopic surgery, significant development has gone into a range of endoscopic surgical instruments having end effectors that engage tissue to accomplish a number of surgical tasks. For example, end effectors have been developed to act as endocutters, graspers, cutters, staplers, clip appliers, access devices, drug/gene therapy delivery devices, ultrasound, RF, or laser energy devices, and other surgical instruments.

In use, the positioning of the end effector at the surgical site may be constrained by the trocar cannula. Generally, the elongate shaft of the device enables the clinician to insert the end effector to a desired depth and rotate the end effector about the longitudinal axis of the shaft. This allows the end effector to be positioned at the surgical site, to a degree. With judicious placement of the trocar and use of graspers, for instance, through another trocar, this amount of positioning is often sufficient. Depending upon the nature of the operation, however, it may be desirable to adjust the positioning of the end effector of an endoscopic surgical instrument. In particular, it is often desirable to orient the end effector at any one of multiple angles relative to the longitudinal axis of the elongate shaft of the instrument.

Movement of the end effector through multiple angles relative to the instrument shaft is conventionally referred to as "articulation." Articulation is typically accomplished by a pivot (or articulation) joint being placed in the elongate shaft just proximal to the end effector. This allows the clinician to articulate the end effector remotely to either side for better surgical placement of the tissue fasteners and easier tissue manipulation and orientation. An articulating end effector permits the clinician to more easily engage tissue in some instances, such as behind an organ. In addition, articulated positioning advantageously allows an endoscope to be positioned behind the end effector without being blocked by the elongate shaft.

Approaches to articulating end effectors tend to be complicated because mechanisms for controlling the articulation must be integrated with mechanisms for operating the end effector. For example, for end effectors that have open and closable jaw features, the closure sleeve, drive member and mechanisms for articulation must be implemented within the small diameter constraints of the instrument's shaft. One common prior design involves an accordion-like articulation mechanism ("flex-neck") that is articulated by selectively drawing back one of two connecting rods through the implement shaft wherein each rod is offset respectively on opposite sides of the shaft centerline. The connecting rods ratchet through a series of discrete positions.

Over the years, other forms of articulating end effector arrangements have been developed. For example, U.S. Pat. No. 7,670,334, entitled "Surgical Instrument Having an Articulating End Effector", and U.S. Pat. No. 7,819,298, entitled "Surgical Stapling Apparatus With Control Features Operable With One Hand", the disclosures of which are each herein incorporated by reference in their respective entireties, disclose various surgical instruments that employ articulating end effector arrangements that effectively address many of the shortcomings of prior instruments with articulating effectors.

Many prior surgical instrument arrangements also employ a component commonly referred to as a "nozzle" that is rotatably supported on the instrument handle and is attached to the elongated shaft. When the clinician desires to rotate the end effector about the shaft axis, he or she simply rotates the nozzle relative to the handle. When the clinician also desires to articulate the end effector, the clinician must actuate a slide bar or other form of articulation control member to accomplish the desired articulation. Such control devices (e.g., the nozzle and articulation bar/control arrangement) typically must be actuated by using both hands.

In performing many surgical procedures, it is desirable to effect a desired amount of end effector articulation and rotation by using only one hand. For example, many vascular operations require precise control of the end effector. In such applications, it would be desirable to be able to have a surgical instrument that employs a single control mechanism for selectively articulating and rotating the end effector that can be easily actuated by using the same hand that is supporting the handle portion of the instrument.

The foregoing discussion is intended only to illustrate some of the shortcomings present in the field of the invention at the time, and should not be taken as a disavowal of claim scope.

SUMMARY

In accordance with general aspects of at least one form, there is provided an articulating surgical instrument that includes a shaft that defines a longitudinal axis. An end effector is coupled to the shaft for selective travel about an articulation axis that is substantially transverse to the longitudinal axis. A nozzle is supported relative to the shaft such that the nozzle may be axially moved in first and second axial directions relative to the shaft. Rotation of the nozzle about the longitudinal axis causes the shaft to rotate about the longitudinal axis. An articulation assembly operably interfaces with the end effector and the nozzle such that movement of the nozzle in the first axial direction causes the articulation assembly to apply a first articulation motion to the end effector to cause the end effector to move in a first articulation direction about the articulation axis and movement of the nozzle in the second axial direction causes the articulation assembly to apply a second articulation motion to the end effector to cause the end effector to move in a second articulation direction about the articulation axis.

In accordance with other general aspects of at least one form, there is provided an articulating surgical instrument that includes a shaft that defines a longitudinal axis. An end effector is coupled to the shaft for selective travel about an articulation axis that is substantially transverse to the longitudinal axis. In various forms, a nozzle is pivotally supported relative to the shaft such that the nozzle may be pivoted in first and second actuation directions relative to the shaft and rotation of the nozzle about the longitudinal axis causes the end effector to rotate about the longitudinal axis. An articulation assembly operably interfaces with the end effector and the nozzle such that movement of the nozzle in the first actuation direction causes the articulation assembly to apply a first articulation motion to the end effector to cause the end effector to move in a first articulation direction about the articulation axis and movement of the nozzle in the second actuation direction causes the articulation assembly to apply a second articulation motion to the end effector to cause the end effector to move in a second articulation direction about the articulation axis.

In accordance with still other general aspects of at least one form, there is provided an articulating surgical instrument that includes a shaft that defines a longitudinal axis. An end effector is coupled to the shaft for selective travel about an articulation axis that is substantially transverse to the longitudinal axis. In various forms, a rotation nozzle is coupled to the shaft such that rotation of the rotation nozzle causes the end effector to rotate about the longitudinal axis. An articulation nozzle is coaxially aligned with the rotation nozzle and is pivotally supported relative to the shaft such that the articulation nozzle may be pivotally moved in first and second pivotal directions relative to the shaft. In various forms, an articulation assembly operably interfaces with the end effector and the articulation nozzle such that movement of the articulation nozzle in the first pivotal direction causes the articulation assembly to apply a first articulation motion to the end effector to cause the end effector to move in a first articulation direction about the articulation axis and movement of the articulation nozzle in the second pivotal direction causes the articulation assembly to apply a second articulation motion to the end effector to cause the end effector to move in a second articulation direction about the articulation axis.

In accordance with another general aspect of at least one form, there is provided an articulating surgical instrument that includes a shaft that defines a longitudinal axis. An end effector is pivotally coupled to the shaft for selective pivotal travel about an articulation axis that is substantially transverse to the longitudinal axis. In various forms, the surgical instrument further includes a nozzle assembly that comprises a first nozzle segment that is movably supported on the shaft and a second nozzle segment that is movably coupled to the first nozzle segment and is movably supported on the shaft such that the first and second nozzle segments may be selectively moved on the shaft relative to each other. In various forms the surgical instrument further includes an articulation assembly that operably interfaces with the end effector and the first and second nozzle segments such that movement of the first nozzle segment in a first axial direction causes the articulation assembly to apply a first articulation motion to the end effector and movement of the second nozzle segment a second axial direction causes the articulation assembly to apply a second articulation motion to the end effector.

In accordance with another general aspect of at least one form, there is provided an articulating surgical instrument that includes a shaft that defines a longitudinal axis. An end effector is pivotally coupled to the shaft for selective pivotal travel about an articulation axis that is substantially transverse to the longitudinal axis. An actuator is pivotally supported relative to the shaft and comprises a first actuator portion that is pivotally supported relative to the shaft. The first actuator portion has a first actuator cam slot therein. A second actuator portion is pivotally supported relative to the shaft and has a second actuator cam slot therein. In various forms the articulating surgical instrument further comprises a first elongated articulation member that has a first proximal end and a first distal end. The first distal end is operably coupled to the end effector and the first proximal end has a first pivot pin extending therefrom into the first cam slot. The instrument further comprises a second elongated articulation member that has a second proximal end and a second distal end. The second distal end is operably coupled to the end effector and the second proximal end has a second pin extending therefrom into the second cam slot such that operation of the actuator in a first pivotal direction causes the first elongated articulation member to apply a first articulation motion to the end effector and operation of the actuator in a second pivotal direction causes the second elongated articulation member to apply a second articulation motion to the end effector.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 34 is a perspective view of a non-limiting articulation control system embodiment of at least one other form of the present invention;

FIG. 35 is a perspective view of a portion of the non-limiting articulation control system embodiment of FIG. 34;

FIG. 49 is a cross-sectional view of the non-limiting articulation control system embodiment of FIGS. 43-48 in a locked position; and FIG. 50 is an enlarged cross-sectional view of a portion of the non-limiting articulation control system embodiment of FIGS. 43-49 in a locked position.

DETAILED DESCRIPTION

Figure 1:
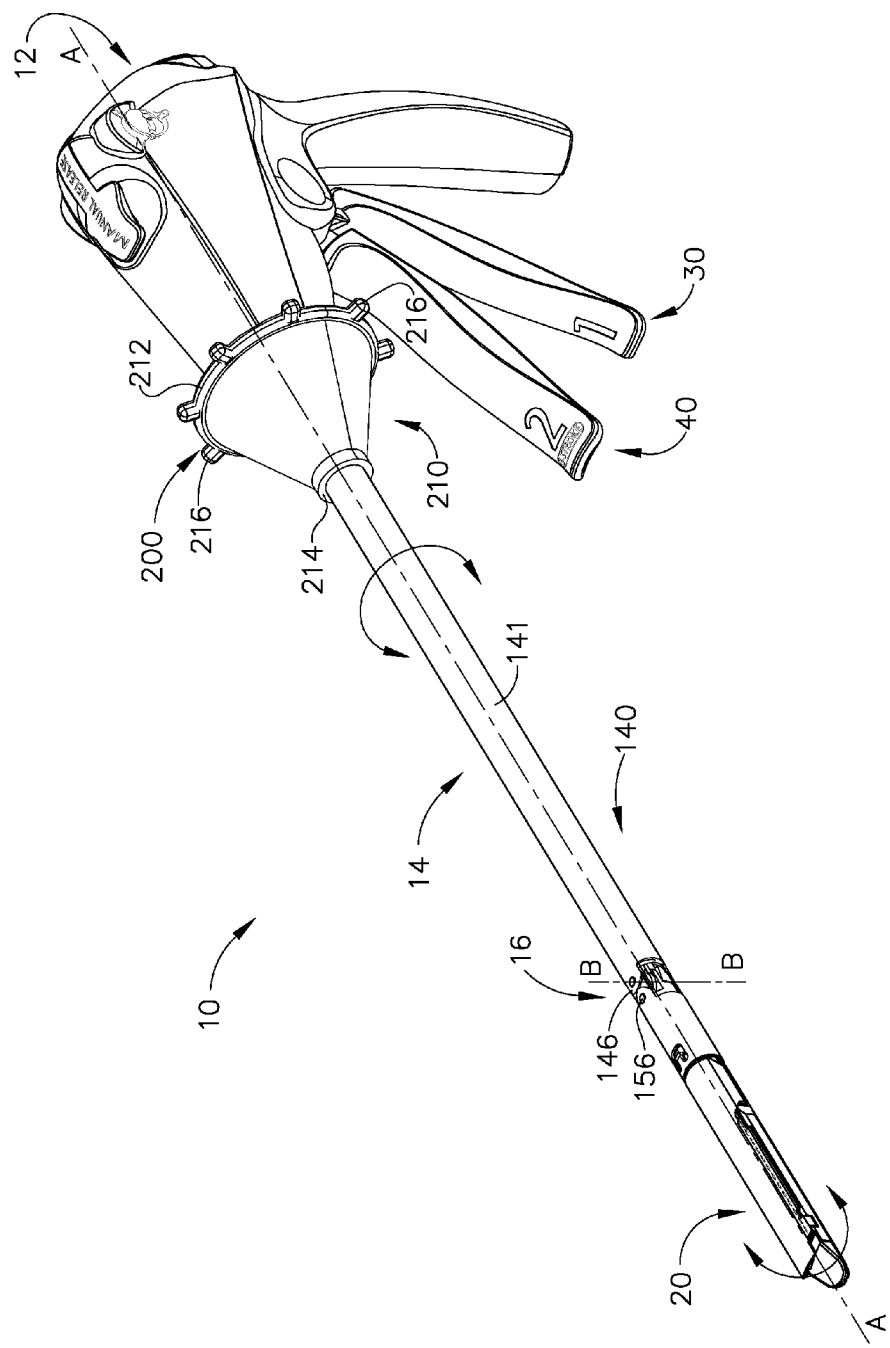
FIG. 1 is a perspective view of a surgical instrument with a non-limiting articulating end effector embodiment of one form of the present invention.

Applicant of the present application also owns U.S. patent application Ser. No. 13/048,566, entitled "SURGICAL INSTRUMENTS WITH LOCKABLE ARTICULATABLE END EFFECTOR", now U.S. Patent Application Publication No. US-2012-0234893-A1, which was filed on even date herewith and which is hereby incorporated by reference in its entirety.

Certain exemplary embodiments will now be described to provide an overall understanding of the principles of the structure, function, manufacture, and use of the instruments and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the various invention embodiments disclosed herein and their respective equivalents.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", "down", "right" and "left" may be used herein with respect to the drawings. However, surgical instruments are used in many orientations and positions, and these terms are not intended to be limiting and/or absolute.

Various exemplary instruments and methods are provided for performing laparoscopic and minimally invasive surgical procedures. However, the person of ordinary skill in the art will readily appreciate that the various methods and instruments disclosed herein can be used in numerous surgical procedures and applications including, for example, in connection with "open" surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device such as a trocar that has a working channel through which the end effector and elongated shaft of a surgical instrument can be advanced.

Turning to the Drawings wherein like numerals denote like components throughout the several views, FIG. 1 depicts one embodiment of a surgical stapling and severing instrument 10 that is capable of practicing various unique benefits of at least one form of the present invention. Various portions of the instrument 10 may be identical to portions of the devices disclosed in U.S. Pat. No. 7,670,334, which has been herein incorporated by reference and/or U.S. Pat. No. 7,000,818, entitled "Surgical Stapling Instrument Having Separate Distinct Closing and Firing Systems", the disclosure of which is herein incorporated by reference in its entirety.

As shown in FIG. 1, in one non-limiting form, the surgical instrument 10 generally includes a handle 12, a shaft 14 and an articulating end effector 20 that is pivotally connected to the shaft 14 at articulation pivot 16. An articulation control 200 is provided to effect rotation of the end effector 20 about the articulation pivot 16. The end effector 20 is shown configured to act as an endocutter for clamping, severing and stapling tissue. However, those of ordinary skill in the art will understand that various embodiments of the present invention may include end effectors (not shown) that are configured to act as other surgical devices including, for example, graspers, cutters, staplers, clip appliers, access devices, drug/gene therapy delivery devices, ultrasound, RF, or laser energy devices, etc.

The handle 12 of the instrument 10 may include a closure trigger 30 and a firing trigger 40 for actuating the end effector 20. It will be appreciated that instruments having end effectors directed to different surgical tasks may have different numbers or types of triggers or other suitable controls for operating an end effector. The end effector 20 is shown separated from a handle 12 by the elongate shaft 14 that defines a longitudinal axis A-A. A clinician may articulate the end effector 20 relative to the shaft 14 about an articulation axis B-B that is substantially transverse to the longitudinal axis A-A (articulation pivot 16) utilizing the articulation control 200 as will be discussed in further detail below. As used herein, the phrase, "substantially transverse to the longitudinal axis" where the "longitudinal axis" is the axis of the shaft 14, refers to a direction that is nearly perpendicular to the longitudinal axis. It will be appreciated, however, that directions that deviate some from perpendicular to the longitudinal axis are also substantially transverse to the longitudinal axis.

Figure 2:
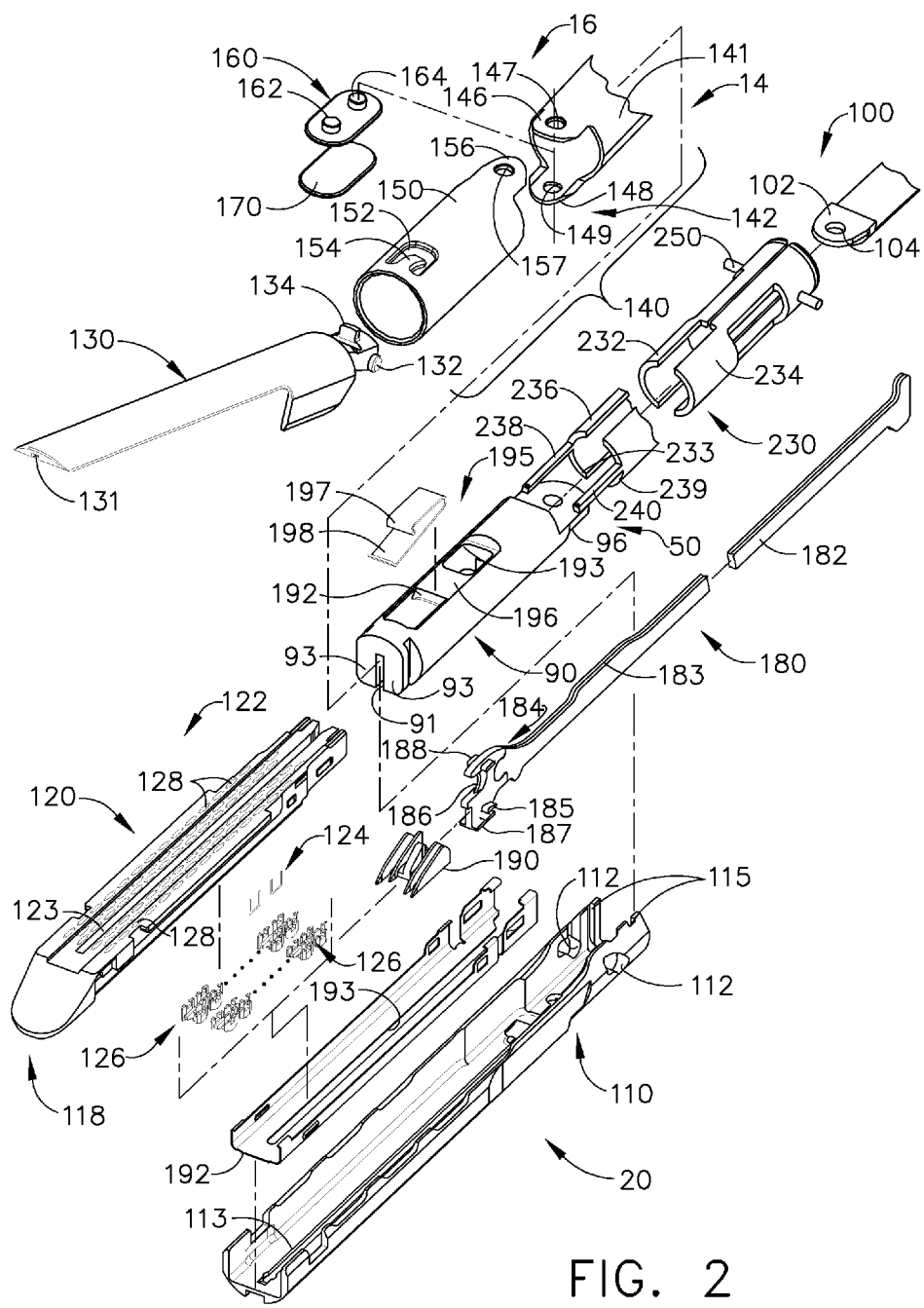
FIG. 2 is an exploded assembly view of a non-limiting end effector embodiment of at least one form of the present invention.

FIG. 2 shows an exploded view of the end effector 20 and elongate shaft 14 including various internal components. An end effector frame 90 and shaft frame 100 are configured to be joined at articulation pivot 50 which defines an articulation axis B-B (FIG. 1). The shaft frame 100 is supported by the handle 12 in a known manner. As such, the construction of shaft frame 100 will not be discussed in great detail herein beyond that which is necessary to understand the various embodiments of the present invention. In various embodiments, for example, the end effector frame 90 has a boss 96 integrally formed or otherwise attached thereto that is coupled to a distally directed tang 102 on the shaft frame 100 defining an aperture 104. The aperture 104 may be positioned to interface with an articulation pin (not shown) included in end effector frame 90 allowing the end effector frame 90 to pivot relative to the shaft frame 100, and accordingly, the end effector 20 to pivot relative to the shaft 14. When assembled, the various components may pivot about articulation pivot 50 at articulation axis B-B as shown in FIG. 1.

As can be further seen in FIG. 2, in one non-limiting form, the end effector 20 includes an elongate channel 110 that is sized and configured to removably support a staple cartridge 120 therein. The elongate channel 110 is attached to the end effector frame 90 by a pair of frame tabs 93 that extend into corresponding slots 115 in the elongate channel 110. The staple cartridge 120 may comprise a molded cartridge body 122 that operably supports a plurality of staples 124 resting upon corresponding staple drivers 126 within respective upwardly open staple apertures 128. In this non-limiting embodiment, the end effector 20 also includes an anvil 130 that is coupled to the elongate channel 110. A pair of apertures 112 may be provided in elongate channel 110 to movably receive trunnions or pins 132 on the anvil 130, allowing the anvil 120 to pivot from an open position to a closed position relative to the elongate channel 110 and staple cartridge 120 in response to opening and closing motions received from a closure tube assembly 140. Such closing motions may also be used to effectively actuate the jaws of other types of end effectors as is known.

As can also be seen in FIG. 2, the closure tube assembly 140 employs a "double pivot" closure sleeve assembly 142. It will be appreciated that the invention is not limited to a double pivot closure sleeve design and may include any suitable closure sleeve arrangement. In various non-limiting embodiments, for example, the double pivot closure sleeve assembly 142 includes a proximal closure tube segment 141 that has upper and lower distally projecting tangs 146, 148. An end effector closure tube section 150 includes a horseshoe aperture 152 and tab 154 for engaging an opening tab 134 on the anvil 130. As is known, when the end effector closure tube section 150 is advanced distally on the end effector frame 90, the horseshoe aperture applies a closing motion to the tab 134 to move the anvil 130 toward the staple cartridge 120. When the end effector closure tube 150 is withdrawn in the proximal direction, the tab 154 engages the tab 134 to move the anvil 130 away from the staple cartridge 120 to an open position. The closure tube section 150 is shown having upper 156 and lower (not visible) proximally projecting tangs.

The end effector closure tube section 150 is pivotally attached to the proximal closure tube segment section 141 by an upper double pivot link 160 and a lower double pivot link 170. The upper double pivot link 160 includes upwardly projecting distal and proximal pivot pins 162, 164 that engage respectively an upper pin hole 157 in the upper proximally projecting tang 156 and an upper proximal pin hole 147 in the upper distally projecting tang 146. A lower double pivot link 170 includes downwardly projecting distal and proximal pivot pins (not shown) that engage respectively a lower distal pin hole in the lower proximally projecting tang and a lower proximal pin hole 149 in the lower distally projecting tang 148. In use, the closure sleeve assembly 140 is translated distally to close the anvil 130, for example, in response to the actuation of the closure trigger 30.

The device 10 further includes a firing bar 180 that is configured to longitudinally translate through the shaft 14, through the flexible closure and pivoting frame articulation joint 50, and through a firing slot 91 in the end effector frame 90 into the end effector 20. The firing bar 180 may be constructed from one solid section, or in various embodiments, may include a laminate material comprising, for example, a stack of steel plates 182. It will be appreciated that a firing bar 180 made from a laminate material may lower the force required to articulate the end effector 20. A distally projecting end of the firing bar 180 is attached to an E-beam 184 that assists in spacing the anvil 130 from the staple cartridge 120 when the anvil 130 is in a closed position. A sharpened cutting edge 186 of the E-beam 184 may also be used to sever tissue.

In operation, the E-beam 184 actuates the staple cartridge 120. A wedge sled 190 is driven distally by the E-beam 184, sliding upon a cartridge tray 192 that holds together the various components of the replaceable staple cartridge 120. The wedge sled 192 upwardly cams the staple drivers 126 to force out the staples 124 into deforming contact with the anvil 130 while a cutting surface 186 of the E-beam 184 severs clamped tissue. The firing bar 180 is movably supported within the shaft 14 such that it passes through the cartridge 120 when the instrument 10 is fired (e.g., actuated). In at least one non-limiting embodiment, the firing bar 180 is instead positioned within the shaft 14 such that all or a portion of the body of the firing bar element 180 is supported by a slot (not shown) in the anvil 130 during firing. Because the anvil 130 may be stronger than the cartridge 120, support from the slot may prevent the firing bar 180 from buckling, even when high loads are applied to the distal end of the firing bar 180. This may be useful in embodiments where the firing bar element 182 includes laminate plates 182.

Various E-beam configurations also include upper pins 188 that are configured to engage the anvil 130 during firing while middle pins 185 and a bottom foot 187 engage various portions of the cartridge body 122, cartridge tray 192 and elongate channel 110. In use, a centrally disposed slot 123 in the cartridge body 122 aligns with a slot 193 in the cartridge tray 190 and with a slot 113 in the elongate channel 110. The leading edge of E-beam 184 slides through the aligned slots 123, 193, and 113. As the firing bar 180 is advanced distally, the foot 187 is braced against the bottom of channel 110 and the upper pins 180 are braced in a groove 131 in the bottom surface of the anvil 130 to prevent the anvil 130 and channel 110 from being forced apart from resistance of tissue. Thereafter, the firing bar 180 is retracted proximally, retracting as well the E-beam 184, allowing the anvil 130 to be opened to release the two stapled and severed tissue portions (not shown).

In various non-limiting embodiments, a spring clip 195 is mounted in the end effector frame 90 as a lockout for firing bar 180. Distal and proximal square apertures 192, 193 formed on top of the end effector frame 90 may define a clip bar 196 therebetween that receives a top arm 197 of a clip spring 195 whose lower, distally extended arm 198 asserts a downward force on a raised portion 183 of the firing bar 180 as is known. It will be appreciated that various embodiments may include other types of lockouts or no lockouts at all.

In the various embodiments depicted in FIGS. 1 and 3-9, the end effector 20 is selectively rotatable about the longitudinal axis A-A and selectively articulatable about articulation axis B-B relative to the proximal shaft segment 141 by the articulation control system 200. In various non-limiting embodiments, the articulation control system 200 includes a nozzle 210 that is rotatably supported relative to the handle 12. In the embodiments depicted in FIGS. 3-9, the nozzle 210 has proximal end portion 212 that tapers to a distal end portion 214. To facilitate easy rotation of the nozzle 210 about the longitudinal axis A-A by a portion of the same hand in which the clinician is gripping the handle 12, a plurality of radially protruding actuation buttons 216 are formed around the proximal end 212 of the nozzle 210 as shown. The clinician may then rotate the nozzle 210 relative to the handle with his or her index finger or other finger or portion of their hand that is supporting the handle 12.

Figure 3:
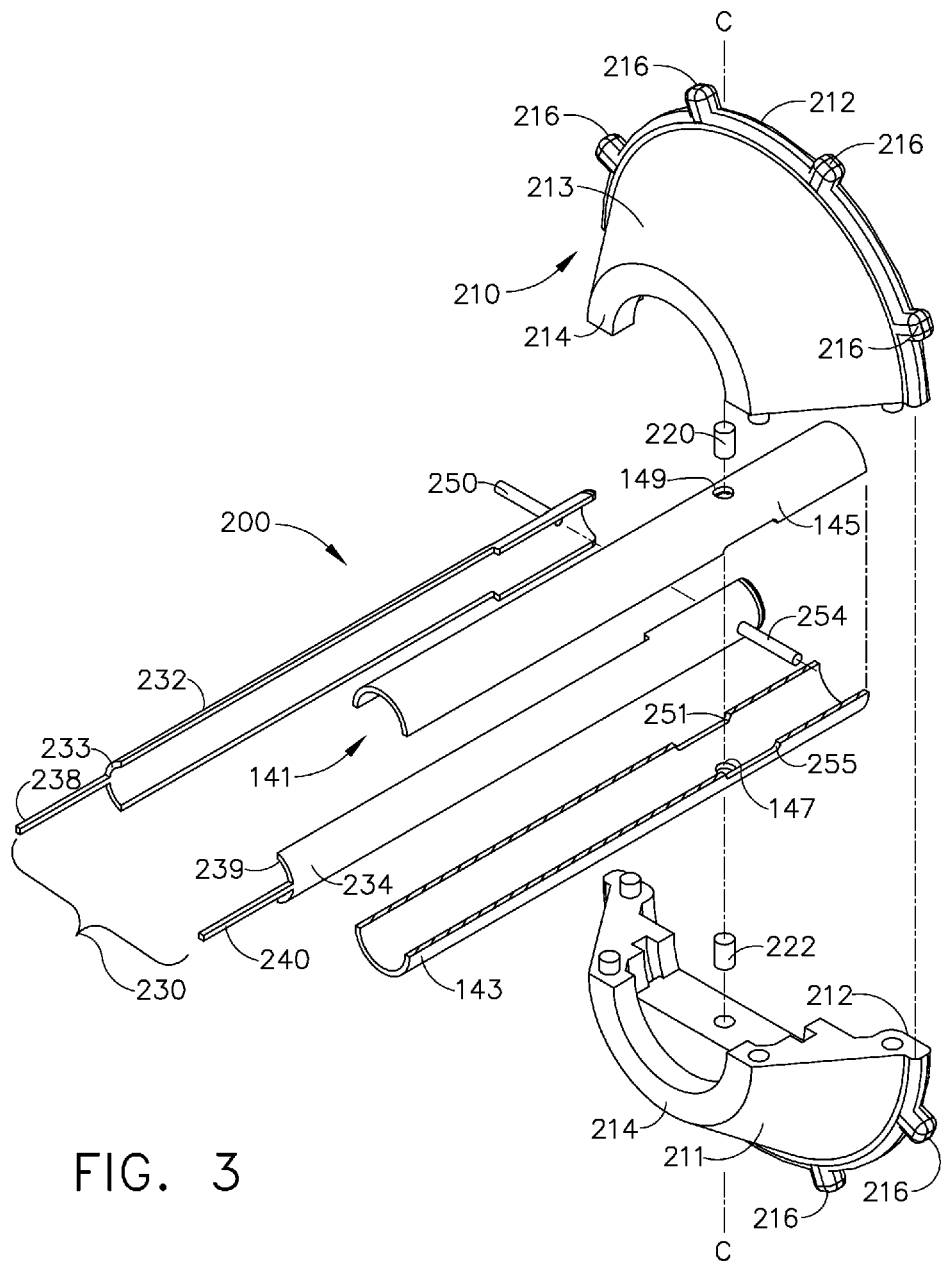
FIG. 3 is an assembly view of a non-limiting articulation control system embodiment of at least one form of the present invention.
Figure 4:
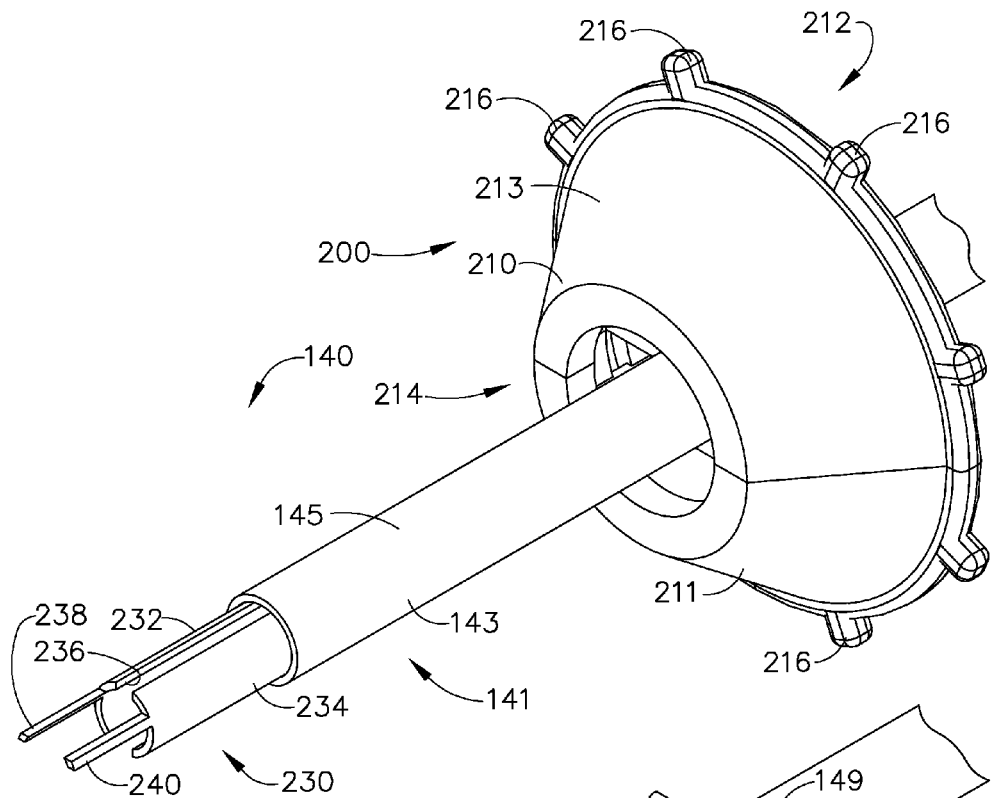
FIG. 4 is a perspective view of the non-limiting articulation control system of FIG. 3.
Figure 5:
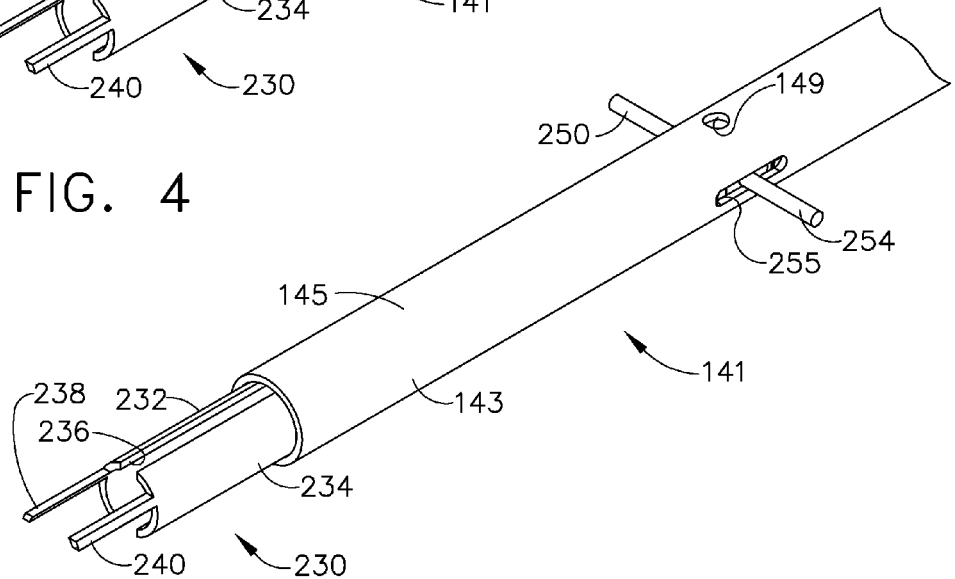
FIG. 5 is a perspective view of a portion of the non-limiting articulation control system of FIGS. 3 and 4.

Turning to FIGS. 3 and 4, it can be seen that the nozzle 210 may be provided in multiple pieces for assembly purposes. In the illustrated embodiment, for example, the nozzle 210 is formed from a lower nozzle portion 211 and an upper nozzle portion 213. Lower and upper nozzle portions 211, 213 may be fabricated from, for example, glass-filled polycarbonate or other suitable material and be interconnected together by appropriate adhesive, welding, snap features, screws, frictional posts/holes, etc. In various non-limiting embodiments, the nozzle 210 is pivotally pinned to the proximal closure tube segment 141 by upper and lower pins 220, 222, respectively. The proximal closure tube segment 141 may be fabricated in multiple segments for assembly purposes. Those of ordinary skill in the art will appreciate that the proximal portion of the proximal closure tube segment 141 will interface with known components for attaching or communicating with the closure trigger of the device. For example, such arrangements are disclosed in U.S. Pat. No. 7,000,818, which has been herein incorporated by reference. However, the actuation of the closure tube assembly may be controlled by a myriad of other known trigger and handle arrangements without departing from the spirit and scope of the present invention. In the embodiment depicted in FIGS. 3-6, the proximal closure tube segment 141 is fabricated from a lower shaft segment 143 and an upper shaft segment 145. In various embodiments, the lower and upper shaft segments 143, 145 may be fabricated from stainless steel or other suitable material and be connected together by an appropriate adhesive or other suitable fastener arrangement to form a substantially hollow tubular structure to accommodate various components of the articulation control system 200 such as an articulation assembly 230 as well as the firing bar 182, shaft frame 100, etc.

Figure 6:
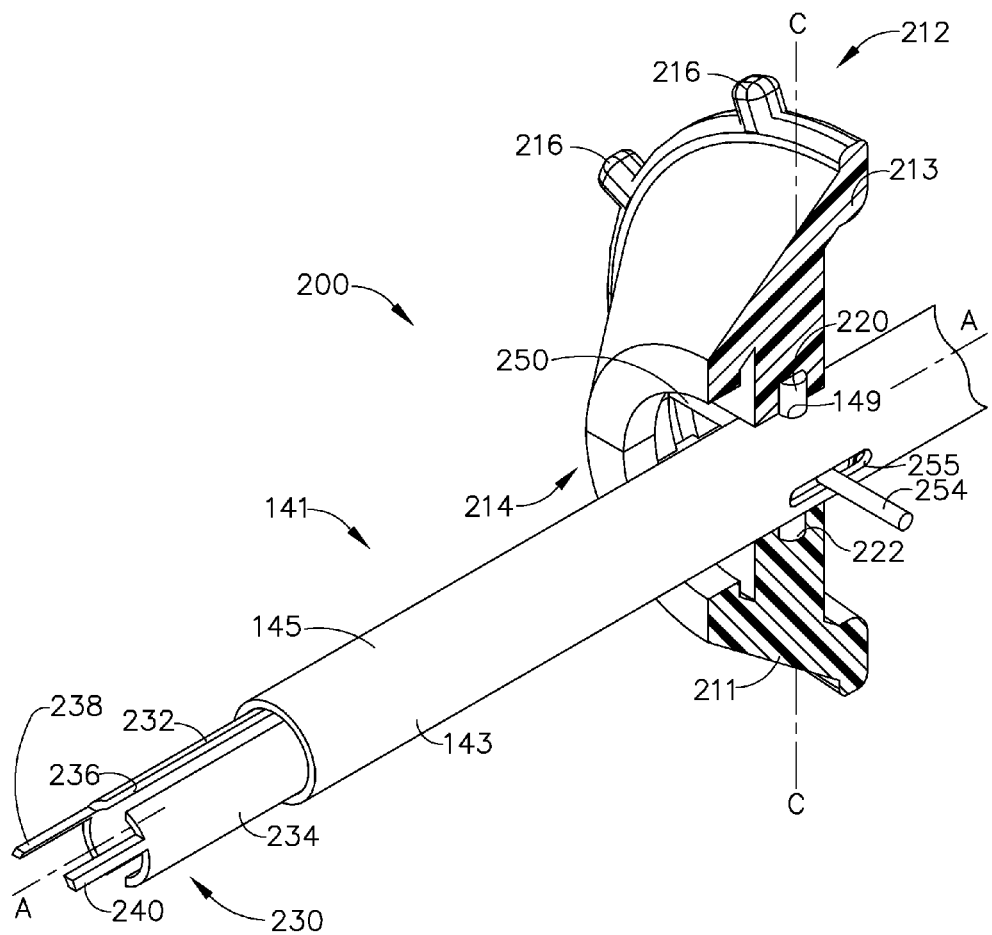
FIG. 6 is a perspective view of the non-limiting articulation control system of FIGS. 3-5 with a portion thereof shown in cross-section.

As can be seen in FIGS. 3 and 6, in various non-limiting embodiments, the upper pin 220 is rotatably received within a hole 149 in the upper shaft segment 145 and the lower pin 222 is rotatably received in a lower hole 147 in the lower shaft segment 143. The upper and lower pins 220, 222 are coaxially aligned and define a nozzle axis C-C about which the nozzle 210 may pivot relative to the proximal closure tube segment 141. As can be most particularly seen in FIG. 6, a hole 219 is provided through the proximal end 214 of the nozzle 210. The hole 219 is sized relative to the proximal closure tube segment 141 to permit the nozzle 210 to be pivoted about the nozzle axis C-C as will be discussed in further detail below.

In the non-limiting embodiment of FIG. 2, the articulation control system 200 includes an articulation assembly 230. In at least one embodiment, the articulation assembly 230 may comprise a right articulation rod 232 and a left articulation rod 234. The right and left articulation rods 232, 234 may be configured as shown in FIGS. 2 and 3 and be fabricated from stainless steel or other suitable material. The articulation assembly 230 comprises a right articulation rod 232 and a left articulation rod 234 that, when received within the proximal closure tube segment 141, may be axially moved therein relative to each other as will be discussed in further detail below. As can be seen in FIG. 2, the right and left articulation rods 232, 234 define a centrally disposed elongate slot 236 that is configured to accommodate the axial movement of the firing bar 180 therebetween. A right articulation band 238 protrudes distally from a distal end 233 of the right articulation rod 232 and a left articulation band 240 protrudes distally from the distal end 239 of the left articulation rod 234. See FIG. 2. In various non-limiting embodiments, the articulation bands 238, 240 are attached to the boss 96. For example, the bands 238, 240 may be pivotally pinned to the boss 96.

The articulation assembly 230 is configured to interface with the nozzle 210 such that pivotal travel of the nozzle 210 about the nozzle axis C-C results in the axial actuation of the right and left articulation rods 232, 234 which ultimately causes the end effector 20 to articulate about articulation axis B-B. More specifically and with reference to FIGS. 3, 5, and 6-9, the right articulation rod 232 has a right pivot pin 250 that is attached thereto and protrudes laterally therefrom through a right slot 251 in the proximal closure tube segment 141. The end of the right pivot pin 250 extends into a right socket or aperture 252 in the nozzle 210. Similarly, the left articulation rod 234 has a left pivot pin 254 that is attached thereto and protrudes laterally therefrom through a left slot 255 in the proximal closure tube segment 141. The end of the left pivot pin 254 extends into a socket or aperture 256 in the nozzle 210.

Figure 7:
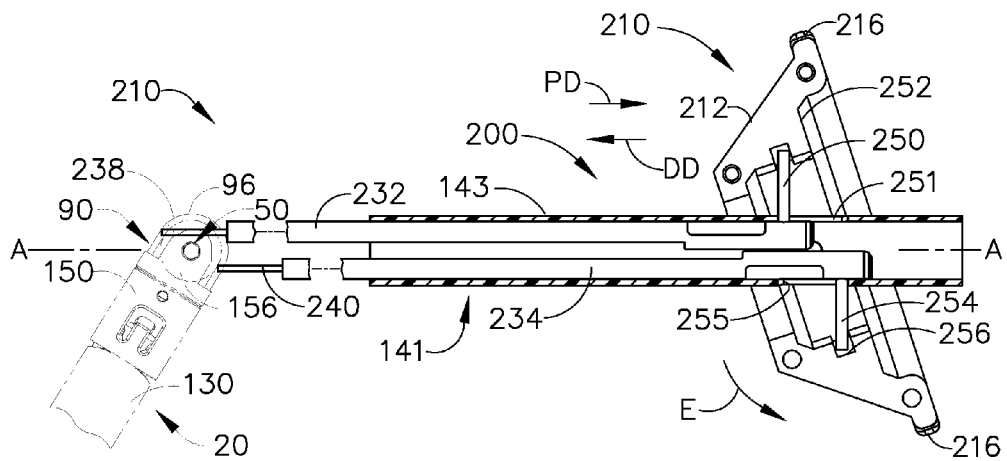
FIG. 7 is a cross-sectional plan view of the non-limiting articulation control system of FIGS. 3-6 with the end effector articulated in a first articulation direction.
Figure 8:
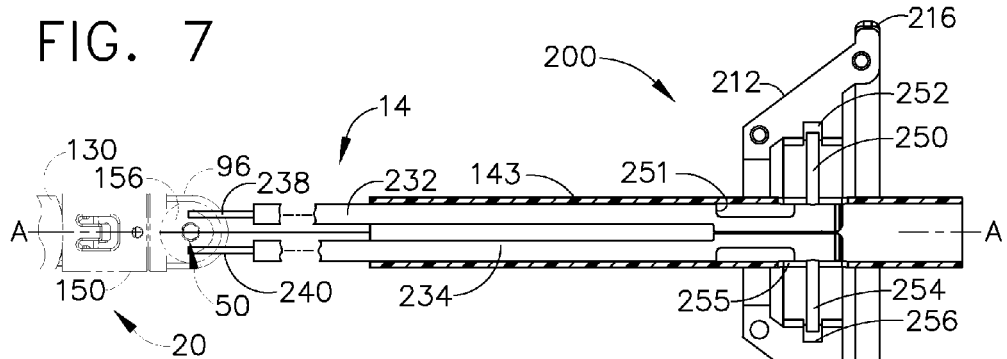
FIG. 8 is another cross-sectional plan view of the non-limiting articulation control system of FIGS. 3-7 with the end effector in an unarticulated orientation.
Figure 9:
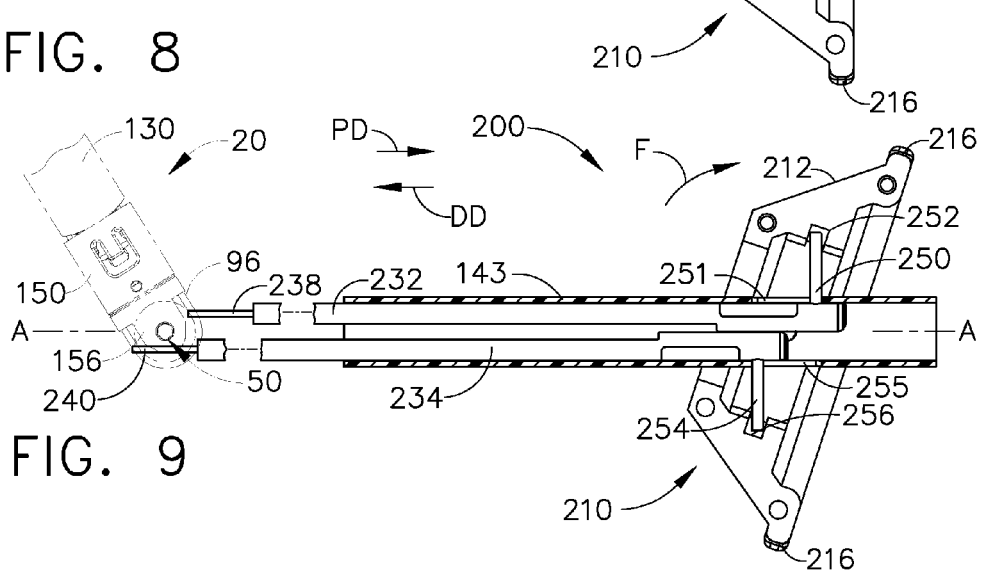
FIG. 9 is another cross-sectional plan view of the non-limiting articulation control system of FIGS. 3-8 with the end effector articulated in a second articulation direction.

The operation of the articulation control system 200 can be understood from reference to FIGS. 7-9. FIG. 7 illustrates articulation of the end effector 20 to the left of the articulation pivot 50 (about articulation axis B-B—shown in FIG. 1). To accomplish this range of articulation, the clinician pivots the nozzle 210 in the first actuation direction represented by arrow "E" in FIG. 7. When the nozzle 210 is pivoted in the "E" direction, the right articulation rod 232 is moved in the distal direction "DD" and the left articulation rod 234 is moved in the proximal direction "PD". Such movement of the right and left articulation rods 232, 234 result in the application of a pushing motion to the boss 96 by the right articulation band 238 and a pulling motion to the boss 96 by the left articulation band 240 which results in the articulation of the end effector 20 as shown. FIG. 8 illustrates the end effector 20 in coaxial alignment with the shaft 14 (e.g., in an unarticulated position). Such end effector orientation may be employed, for example, during insertion of the end effector 20 through a trocar cannula (not shown) or other opening in the patient. FIG. 9 illustrates articulation of the end effector 20 to the right of the articulation pivot 50 (about articulation axis B-B—shown in FIG. 1). To accomplish this range of articulation, the clinician pivots the nozzle 210 in a second actuation direction represented by arrow "F" in FIG. 9. When the nozzle 210 is pivoted in the "F" direction, the right articulation rod 232 is moved in the proximal direction "PD" and the left articulation rod 234 is moved in the distal direction "DD". Such movement of the right and left articulation rods 232, 234 result in the application of a pushing motion to the boss 96 by the left articulation band 240 and a pulling motion to the boss 96 by the right articulation band 238 which results in the articulation of the end effector 20 as shown. The end effector 20 may be rotated about the longitudinal axis simply by rotating the nozzle 210 about the longitudinal axis A-A. This action may be accomplished by a portion of the hand that is supporting the handle portion of the device, thereby avoiding the need for both hands to rotate the end effector about the longitudinal axis. Although the articulation assembly 230 as described above employs two elongated articulation rods or members, in alternative embodiments, only one elongated articulation member is employed.

Figure 10:
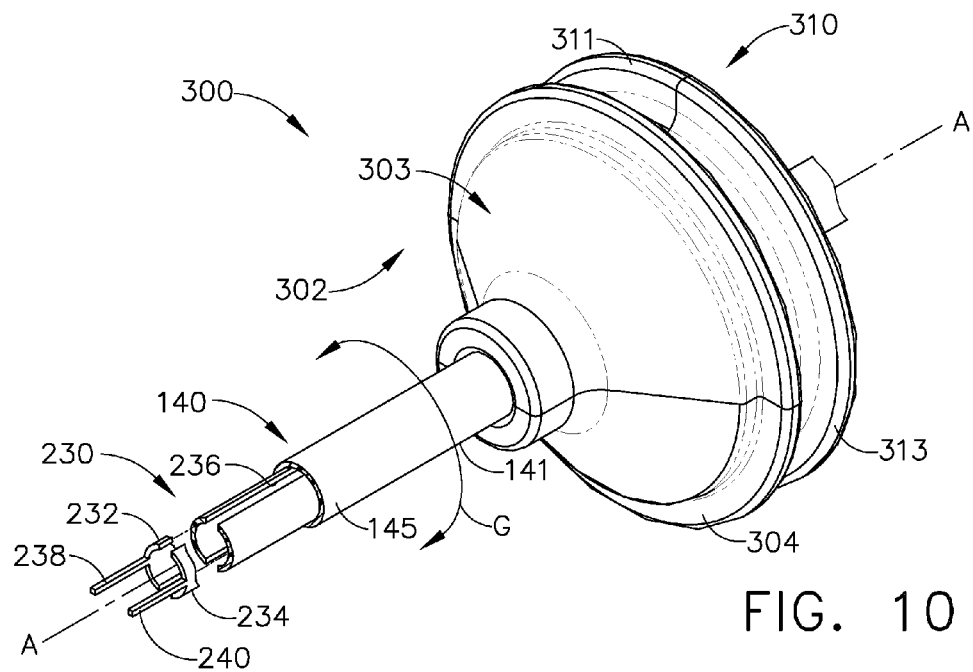
FIG. 10 is a perspective view of a non-limiting articulation control system embodiment of at least one other form of the present invention.
Figure 11:
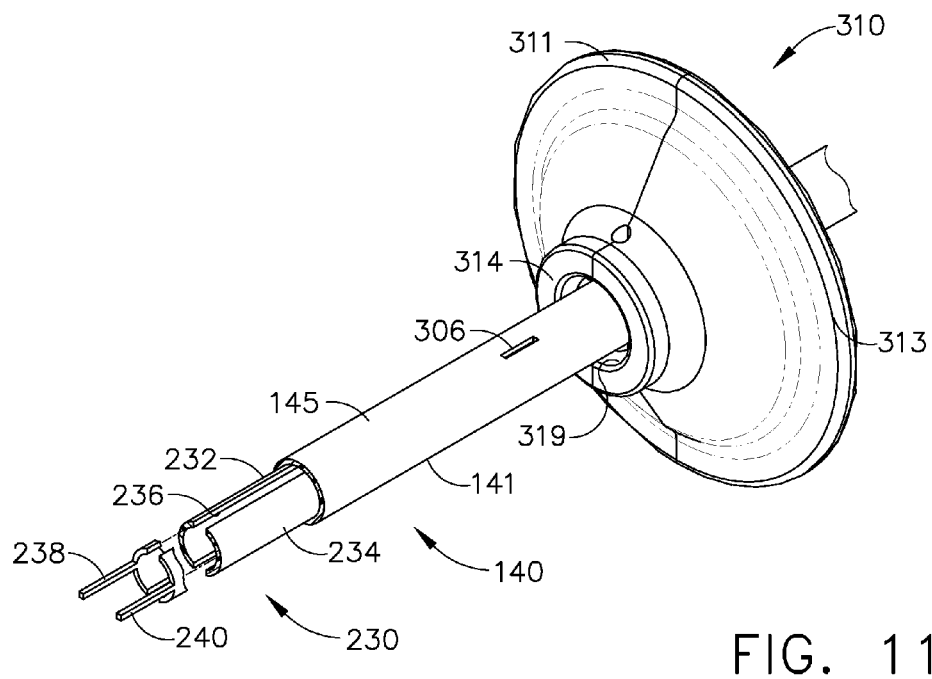
FIG. 11 is a perspective view of the non-limiting articulation control system of FIG. 10 with the rotation nozzle omitted for clarity.
Figure 12:
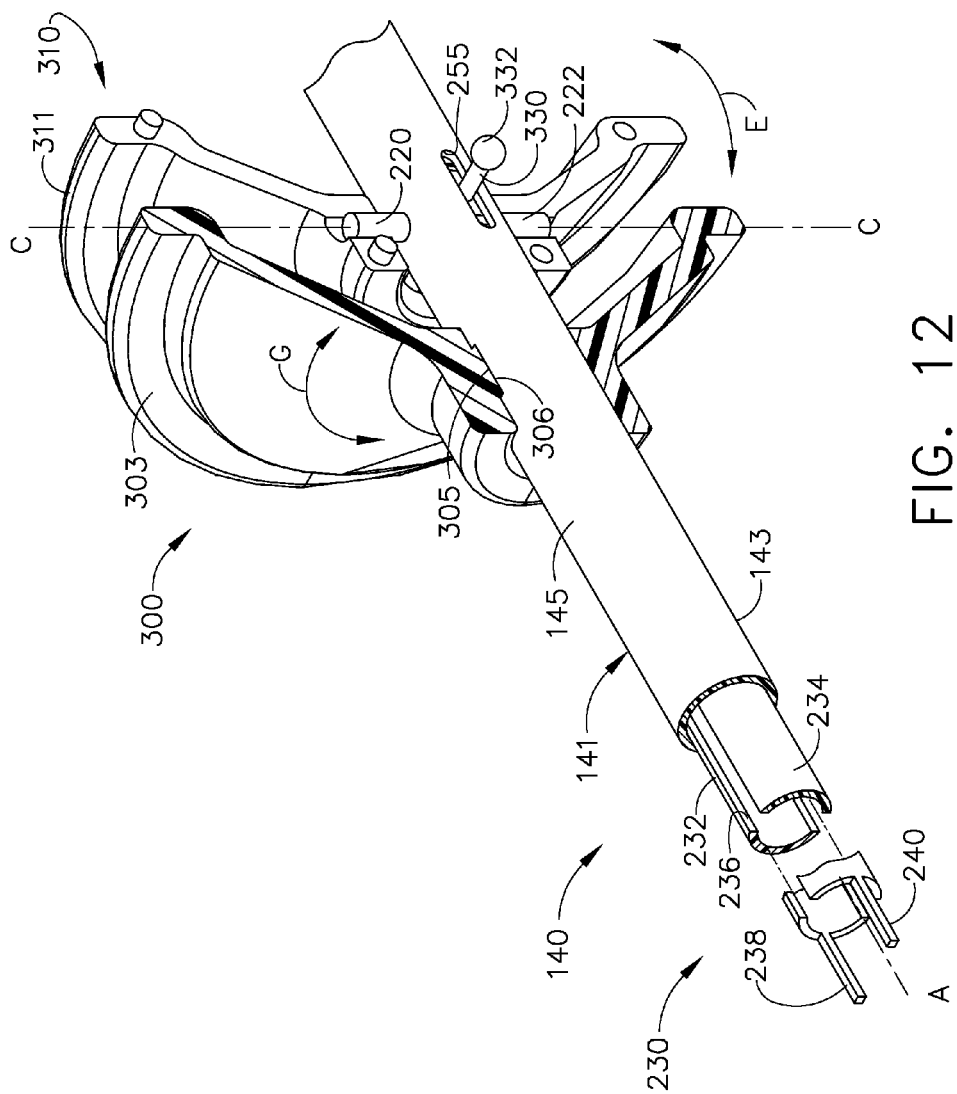
FIG. 12 is a perspective view of the non-limiting articulation control system of FIGS. 10 and 11 with some components thereof shown in cross-section.
Figure 13:
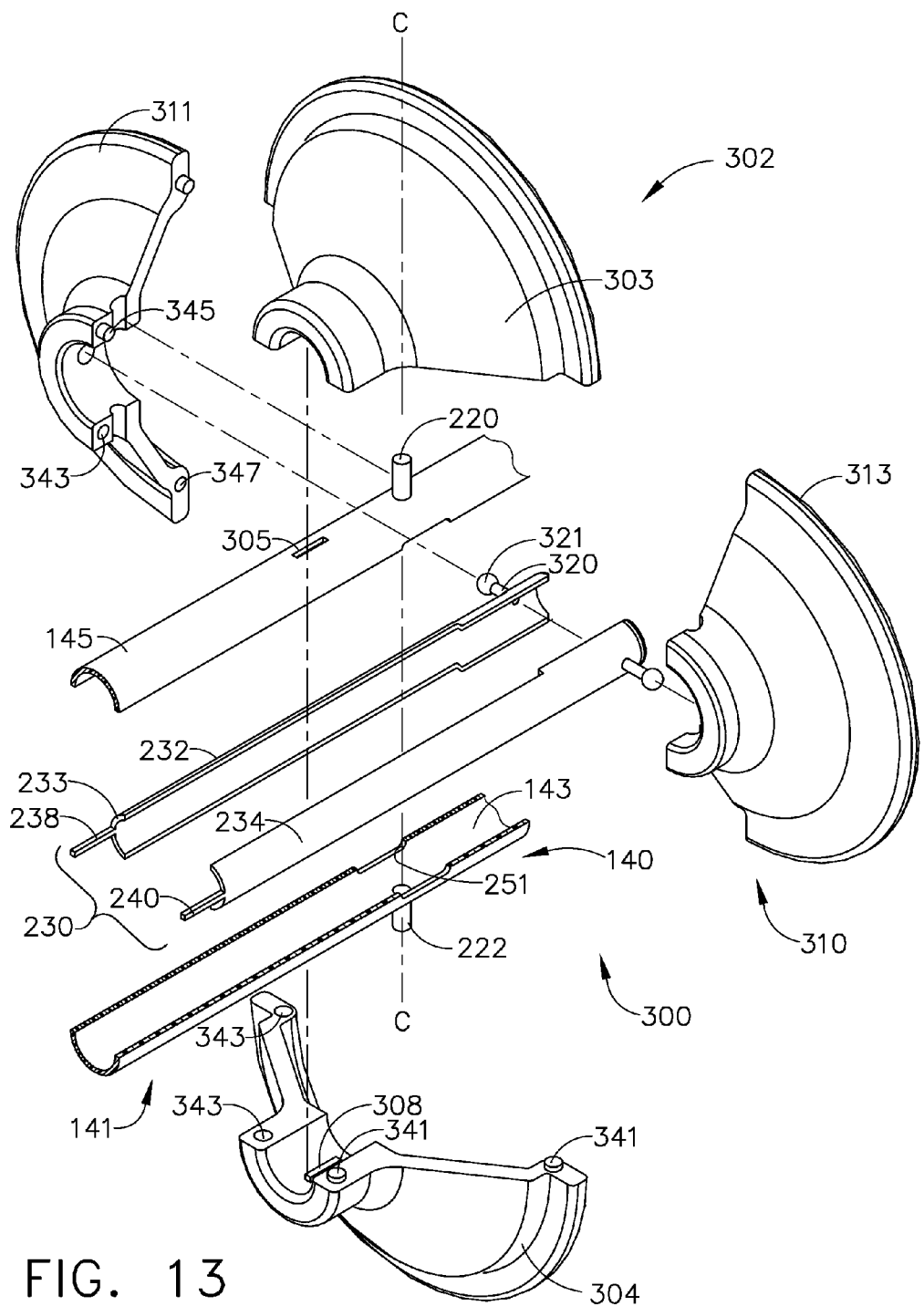
FIG. 13 is an exploded assembly view of the non-limiting articulation control system of FIGS. 10-12.

FIGS. 10-17 illustrate another non-limiting articulation control system embodiment of the present invention generally designed as 300 that is similar to the articulation control system 200 described above, except for the differences noted below. Those components that are the same as the components employed in the above-described embodiments will be labeled with the same element numbers and those of ordinary skill in the art can refer to the disclosure set forth hereinabove that explains their construction and operation. As can be seen in FIG. 10, articulation control system 300 employs a separate rotation nozzle 302 for controlling the rotation (arrow "G" in FIG. 10) of the closure tube assembly 140 and ultimately, the end effector 12. As can be seen in FIG. 13, in at least one embodiment, the rotation nozzle 302 is fabricated from an upper rotation nozzle portion 303 and a lower rotation nozzle portion 304 that is attached to the upper rotation nozzle portion 303 by, for example frictional posts and sockets 341, 343. However, the nozzle portions 303, 304 may be attached together by other suitable means such as adhesive, welding, snap features, screws, etc. The upper rotational nozzle portion 303 and the lower rotational nozzle portion 304 are attached to the proximal closure tube segment 141. In at least one embodiment, for example, the upper rotational nozzle section 303 is keyed to the upper shaft segment 145 by a key 305 that extends through an opening 306 in the upper shaft segment 145 and the lower rotational nozzle section 304 is keyed to the lower shaft segment 143 by a key 307 that extends through an opening 308 in the lower shaft segment 143. However, the rotational nozzle 302 may be non-rotatably attached to the proximal closure tube segment 141 by other suitable means such that rotation of the rotational nozzle 302 results in the rotation of the end effector 20 about the longitudinal axis A-A.

As shown in FIG. 13, the articulation nozzle 310 may be provided in multiple pieces for assembly purposes. In the illustrated embodiment, for example, the articulation nozzle 310 is formed from a right nozzle portion 311 and a left nozzle portion 313. Right and left nozzle portions 311, 313 may be fabricated from, for example, glass-filled polycarbonate and be interconnected together by frictional posts/holes, 345, 347. However, the right and left nozzle portions 311, 313 may be attached together by appropriate adhesive, welding, snap features, screws, etc. In various non-limiting embodiments, the articulation nozzle 310 is pivotally mounted on upper and lower pins 220, 222, respectively. The upper pin 220 is attached to the upper shaft segment 145 and the lower pin 222 is attached to the lower shaft segment 143. The upper and lower pins 220, 222 are coaxially aligned and define a nozzle axis C-C about which the articulation nozzle 310 may pivot relative to the proximal closure tube segment 141. As can be most particularly seen in FIG. 11, a hole 319 is provided through the proximal end 314 of the articulation nozzle 310. The hole 319 is sized relative to the closure tube section 141 to permit the articulation nozzle 310 to be pivoted about the nozzle axis C-C as will be discussed in further detail below.

Figure 14:
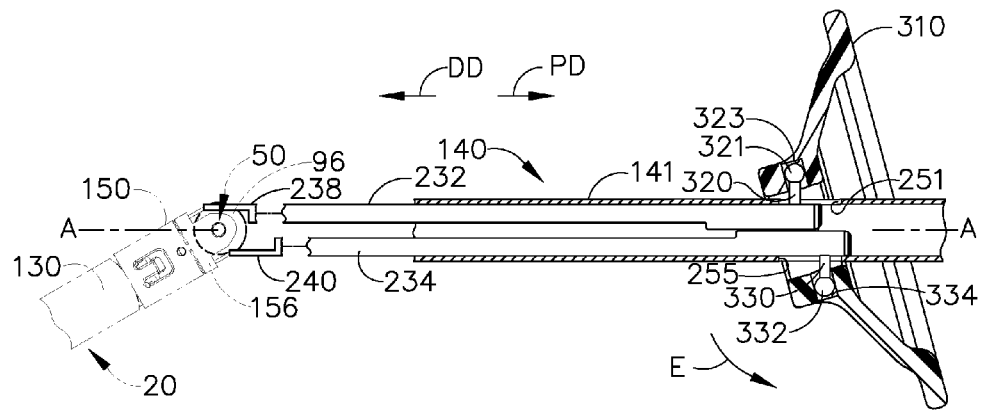
FIG. 14 is a cross-sectional plan view of the non-limiting articulation control system of FIGS. 10-13 with the end effector articulated in a first articulation direction.

In the non-limiting embodiment of FIG. 13, the articulation control system 300 includes an articulation assembly 230. In at least one embodiment, the articulation assembly 230 may comprise a right articulation rod 232 and a left articulation rod 234. The right and left articulation rods 232, 234 may be configured as shown in FIG. 14 and be fabricated from stainless steel or other suitable material. As was discussed above, when the right and left articulation rods are received within the proximal closure tube segment 141, they may be axially moved therein relative to each other. When received within the proximal closure tube segment 141, the right and left articulation rods 232, 234 define a centrally disposed elongate slot 236 that is configured to accommodate the axial movement of the firing bar 180. A right articulation band 238 protrudes distally from a distal end 233 of the right articulation rod 232 and a left articulation band 240 protrudes distally from the distal end 239 of the left articulation rod 234. In various non-limiting embodiments, the articulation bands 238, 240 are attached to the boss 96. For example, the bands 238, 240 may be pivotally pinned to the boss 96.

The articulation assembly 230 is configured to interface with the articulation nozzle 310 such that pivotal travel of the articulation nozzle 310 about the nozzle axis C-C results in the actuation of the articulation assembly 230 which ultimately causes the end effector 20 to articulate about articulation axis B-B at articulation pivot 50. More specifically and with reference to FIGS. 14-17, the right articulation rod 232 has a right pivot pin 320 that is attached thereto and protrudes laterally therefrom through a right slot 251 in the shaft closure tube section 141. In various non-limiting embodiments, a ball 321 may be provided on the end of the right pivot pin 320 and be rotatably received within an aperture 323 in the articulation nozzle 310. Similarly, the left articulation rod 234 has a left pivot pin 330 that is attached thereto and protrudes laterally therefrom through a left slot 255 in the proximal closure tube segment 141. A ball 332 may be provided on the end of the left pivot pin 330 and be rotatably received within an aperture 334 in the articulation nozzle 310.

Figure 15:
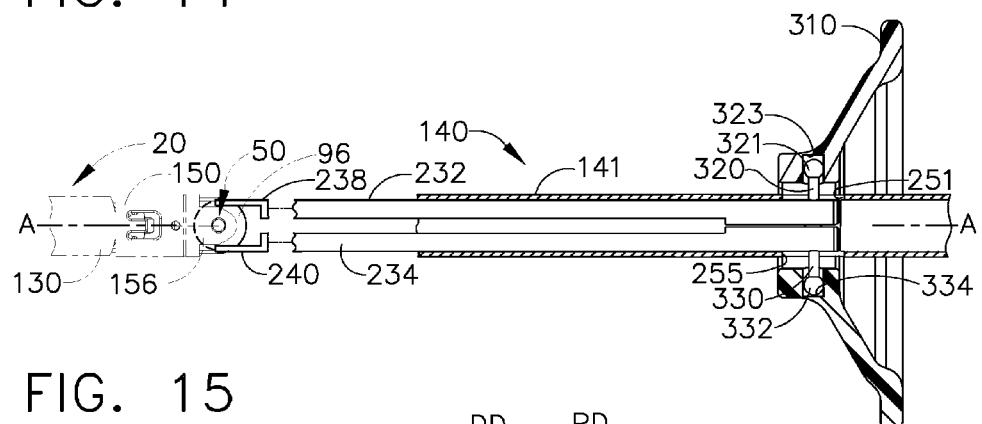
FIG. 15 is another cross-sectional plan view of the non-limiting articulation control system of FIGS. 10-14 with the end effector in an unarticulated orientation.
Figure 16:
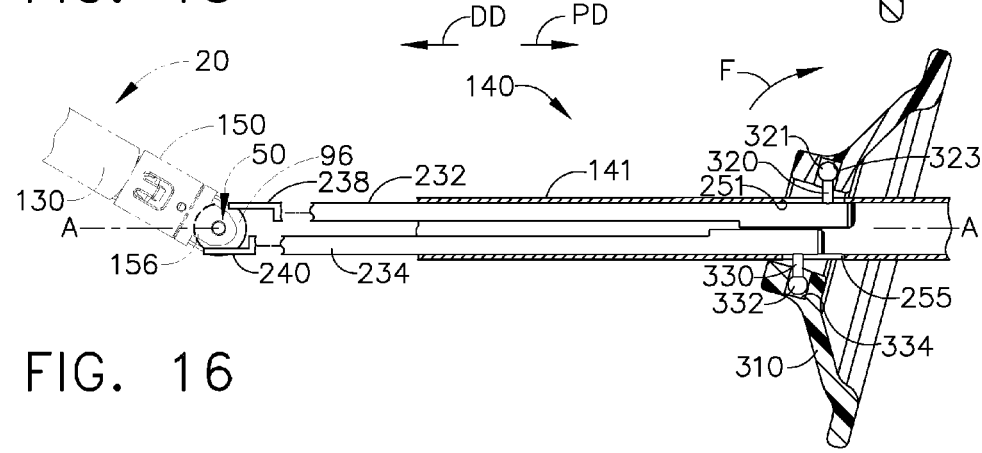
FIG. 16 is another cross-sectional plan view of the non-limiting articulation control system of FIGS. 10-15 with the end effector articulated in a second articulation direction.
Figure 17:
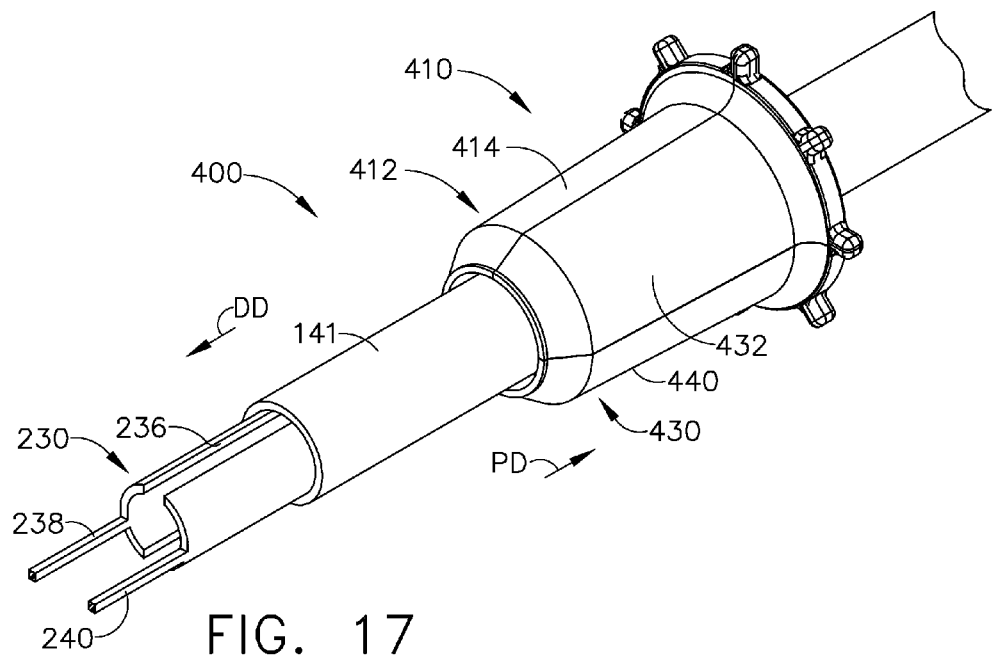
FIG. 17 is a perspective view of a non-limiting articulation control system embodiment of at least one other form of the present invention.
Figure 18:
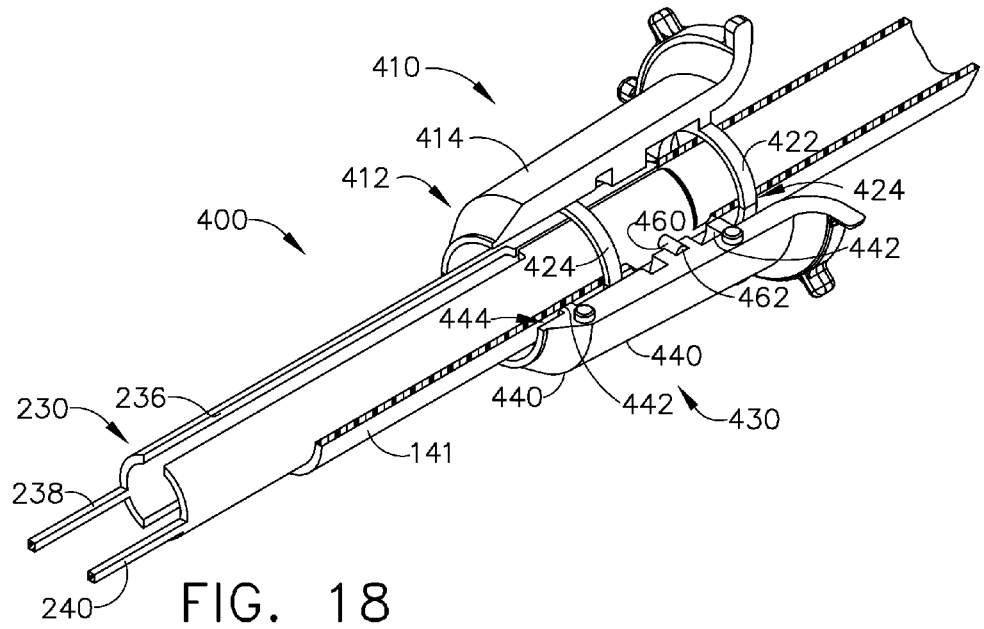
FIG. 18 is another perspective view of the non-limiting articulation control system of FIG. 17 with some components thereof shown in cross-section.

The operation of the articulation control system 300 can be understood from reference to FIGS. 14-16. FIG. 14 illustrates articulation of the end effector 20 to the left of the articulation pivot 50. To accomplish this range of articulation, the clinician pivots the articulation nozzle 310 in the actuation direction represented by arrow "E" in FIG. 14. When the articulation nozzle 310 is pivoted in the "E" direction, the right articulation rod 232 is moved in the distal direction "DD" and the left articulation rod 234 is moved in the proximal direction "PD". Such movement of the right and left articulation rods 232, 234 result in the application of a pushing motion to the boss 96 by the right articulation band 238 and a pulling motion to the boss 96 by the left articulation band 240 which results in the articulation of the end effector 20 as shown. FIG. 15 illustrates the end effector 20 in coaxial alignment with the shaft 14 (e.g., in an unarticulated position). Such end effector orientation may be employed, for example, during insertion of the end effector 20 through a trocar cannula (not shown) or other opening in the patient. FIG. 16 illustrates articulation of the end effector 20 to the right of the articulation pivot 50. To accomplish this range of articulation, the clinician pivots the articulation nozzle 310 in the actuation direction represented by arrow "F" in FIG. 15. When the articulation nozzle 310 is pivoted in the "F" direction, the right articulation rod 232 is moved in the proximal direction "PD" and the left articulation rod 234 is moved in the distal direction "DD". Such movement of the right and left articulation rods 232, 234 result in the application of a pushing motion to the boss 96 by the left articulation band 240 and a pulling motion to the boss 96 by the right articulation band 238 which results in the articulation of the end effector 20 as shown. Although the articulation assembly 230 as described above employs two elongated articulation rods or members, in alternative embodiments, only one elongated articulation member is employed.

FIGS. 17-23 illustrate another non-limiting articulation control system embodiment of the present invention generally designated as 400. Those components that are the same as the components employed in the above-described embodiments will be labeled with the same element numbers and those of ordinary skill in the art can refer to the disclosure set forth hereinabove that explains their construction and operation. In various non-limiting embodiments, the articulation control system 400 includes an articulation nozzle 410 that is fabricated in multiple pieces. For example, the articulation nozzle 410 has a right nozzle portion 412 that is axially movable relative to a left nozzle portion 430. See FIG. 21. In at least one non-limiting embodiment, the right nozzle portion 412 consists of an upper right portion 414 and a lower right portion 420. See FIG. 19. The upper and lower right nozzle portions 412, 414 may be fabricated from, for example, glass-filled polycarbonate or other suitable material. Similarly, the left nozzle portion 430 consists of an upper left nozzle portion 432 and a lower left nozzle portion 440. The upper and lower left nozzle portions 432, 440 may be fabricated from, for example, glass-filled polycarbonate or other suitable material.

Figure 20:
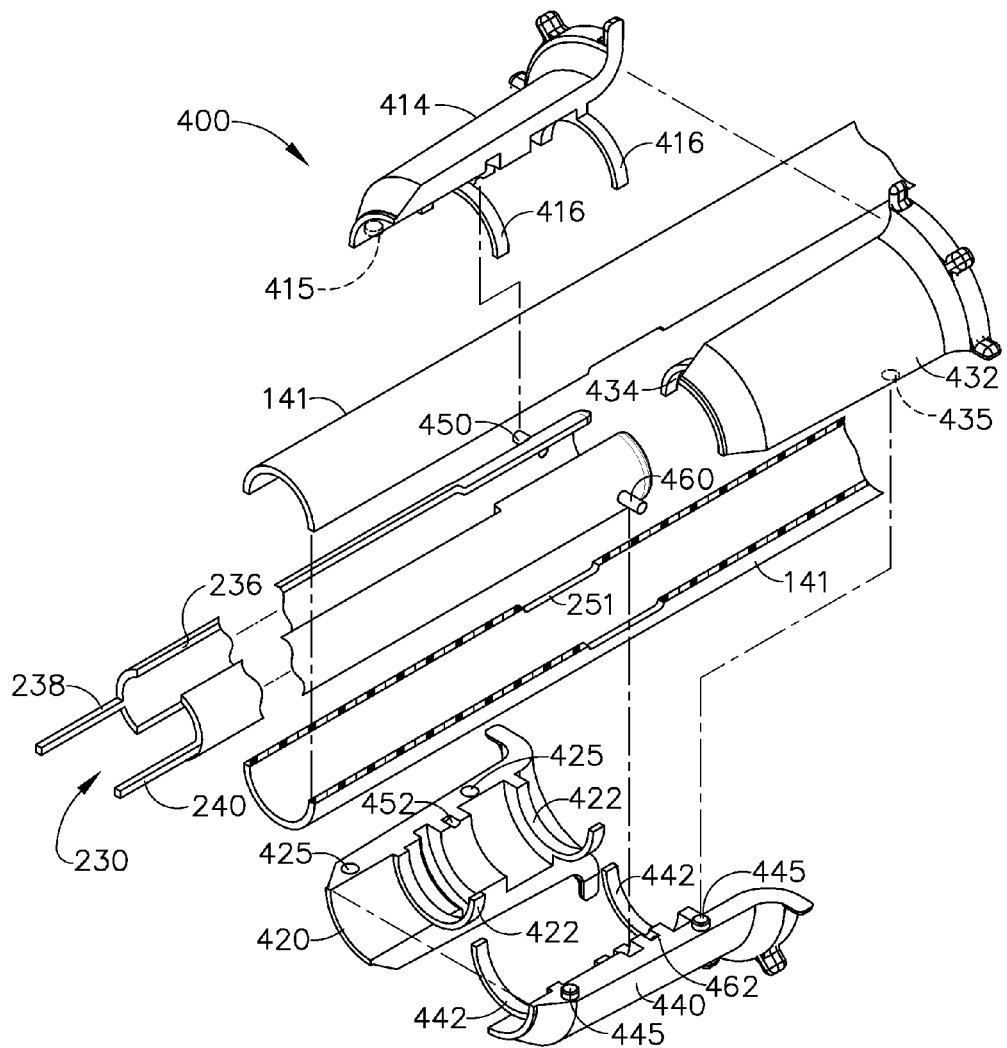
FIG. 20 is another exploded assembly view of the non-limiting articulation control system of FIGS. 17-19 with some components thereof shown in cross-section.
Figure 21:
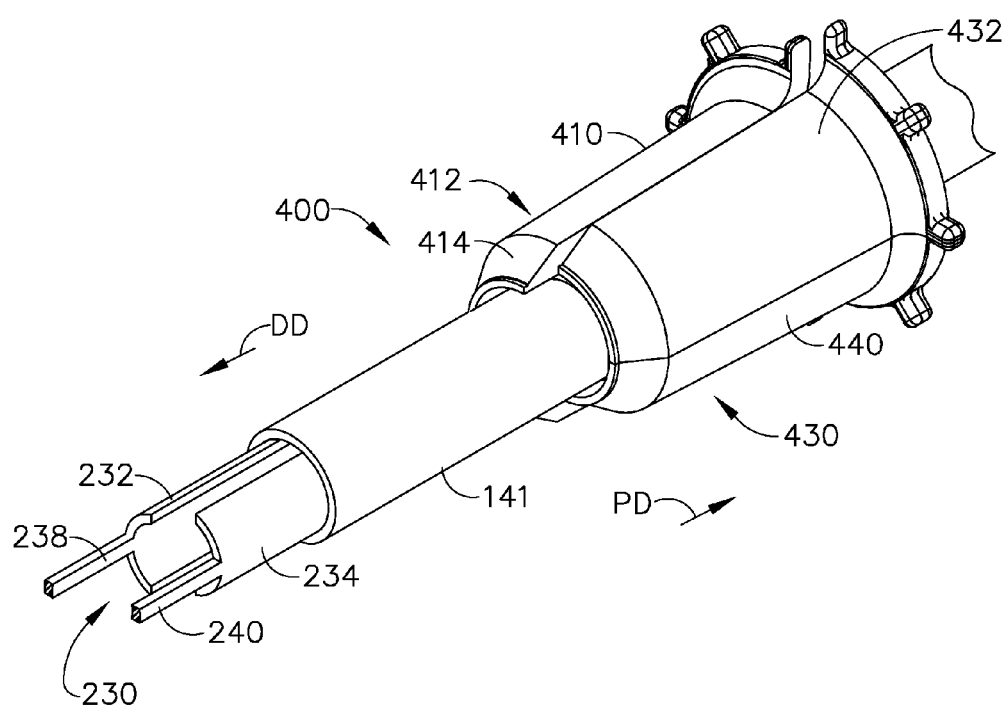
FIG. 21 is a perspective view of the non-limiting articulation control system of FIGS. 17-20 with the right nozzle portion thereof moved in the first actuation direction.

As can be seen in FIG. 20, the upper right nozzle portion 414 is provided with a pair of spaced retention band segments 416 and the lower right nozzle portion 420 is provided with a pair of spaced retention band segments 422. When the upper and lower right nozzle portions 414, 420 are joined together, the retention band segments 416 in the upper portion 414 cooperate with the retention band segments 422 in the lower portion 420 to form continuous annular right retention bands, generally designed as 424, the purpose of which will be discussed in further detail below. Similarly, the upper left nozzle portion 432 is provided with a pair of spaced retention band segments 434 and the lower left nozzle portion 440 is provided with a pair of spaced retention band segments 442. When the upper and lower left nozzle portions 432, 440 are joined together, the retention band segments 434 in the upper portion 432 cooperate with the retention band segments 442 in the lower portion 440 to form continuous annular left retention bands, generally designed as 444.

Figure 19:
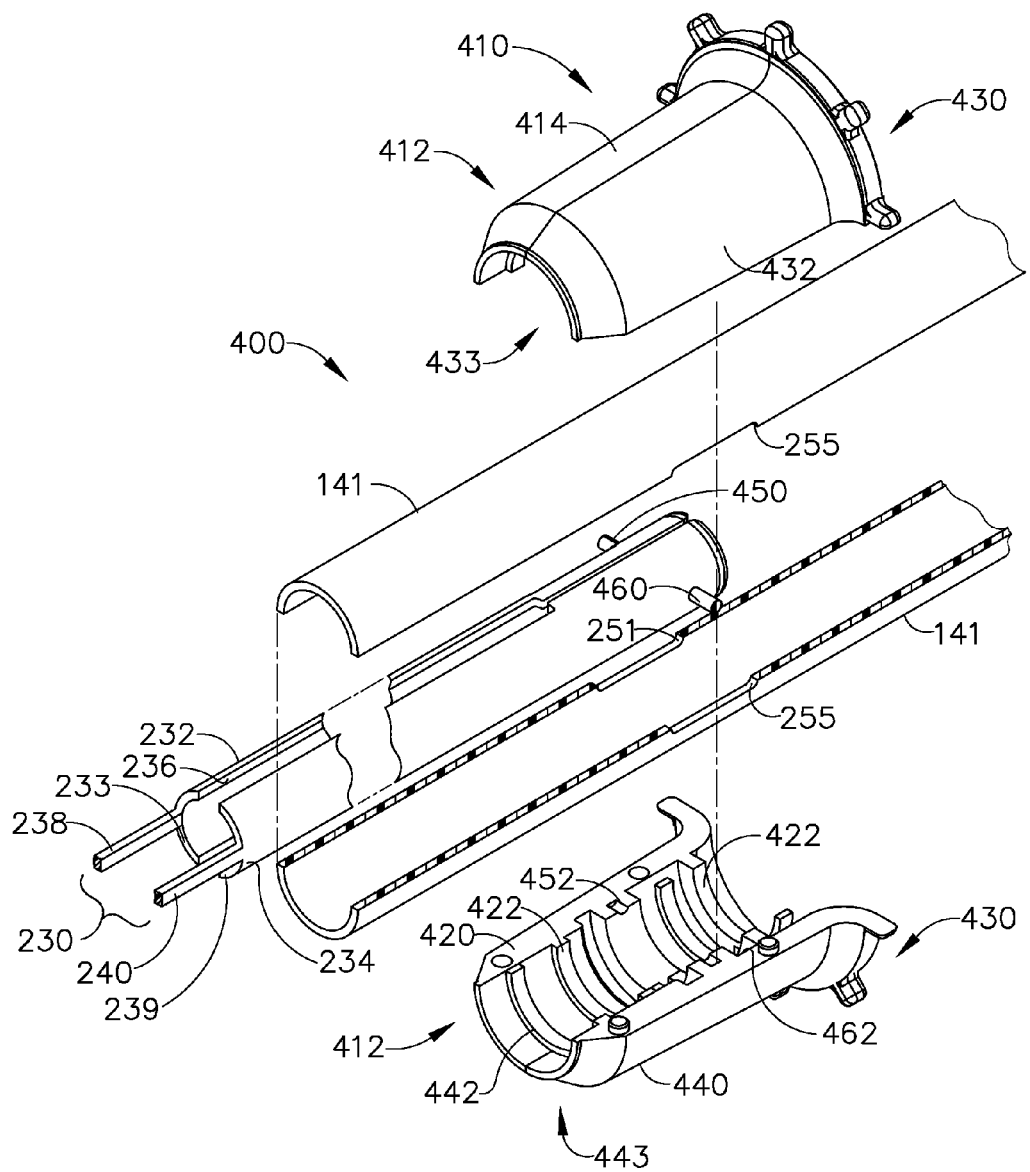
FIG. 19 is an exploded assembly view of the non-limiting articulation control system of FIGS. 17 and 18 with some components thereof shown in cross-section.

In at least one non-limiting embodiment, the articulation control system 400 includes an articulation assembly 230. In at least one embodiment, the articulation assembly 230 may comprise a right articulation rod 232 and a left articulation rod 234. The right and left articulation rods 232, 234 may be configured as shown in FIG. 19 and be fabricated from stainless steel or other suitable material. The right and left articulation rods 232, 234 when movably supported within the proximal closure tube segment 141 as illustrated, serve to define a centrally disposed elongate slot 236 that is configured to accommodate the axial movement of the firing bar 180. A right articulation band 238 protrudes distally from a distal end 233 of the right articulation rod 232 and a left articulation band 240 protrudes distally from the distal end 239 of the left articulation rod 234. In various non-limiting embodiments, the articulation bands 238, 240 are attached to the boss 96. For example, the bands 238, 240 may be pivotally pinned to the boss 96. The right and left articulation rods 232, 234 are slidably inserted into the hollow proximal closure tube segment 141. The right articulation rod 232 has a right pivot pin 450 that is attached thereto and protrudes laterally therefrom through a right slot 251 in the shaft closure tube section 141. Similarly, the left articulation rod 234 has a left pivot pin 460 that is attached thereto and protrudes laterally therefrom through a left slot 255 in the shaft closure tube section 141. Such arrangement enables the right articulation rod 232 and the second articulation rod to be independently axially movable within the proximal closure tube segment 141. The end of the right pivot pin 450 is configured to be received within an aperture 452 formed by the joined upper and lower right nozzle portions 414, 420. Likewise, the end of the left pivot pin 460 is configured to be received within an aperture 462 formed by the upper and lower left nozzle portions 432, 440.

To assemble at least one embodiment, the upper nozzle portions 414, 432 are brought together to form a temporary upper nozzle assembly 433, but remain unattached to each other as illustrated in FIG. 19. As is also illustrated in FIG. 19, the lower nozzle portions 420, 440 are brought together to form a temporary lower nozzle assembly 443, but remain unattached to each other. Then, the temporary upper nozzle assembly 433 is joined to the temporary lower nozzle assembly 443 over the proximal closure tube segment 141 while capturing the right pivot pin 450 in the right aperture 452 and the left pivot pin 460 in the left aperture 462. In at least one non-limiting embodiment, the right upper nozzle portion 414 is provided with attachment posts 415 (FIG. 20) that are sized to be frictionally fitted into attachment holes 425 in the lower right nozzle portion to retain those two portions 414, 420 together to form the right nozzle section 412. Likewise, the lower left nozzle portion 440 is provided with attachment posts 445 that are sized to be frictionally fitted into attachment holes 435 in the upper left nozzle portion 432 to retain those two portions 440, 432 together to form the left nozzle portion 430. However, other fastener arrangements and/or adhesive may be employed to attach the upper right nozzle portion 414 to the lower right nozzle portion 420 and the upper left nozzle portion 432 and the lower left nozzle portion 440.

Figure 22:
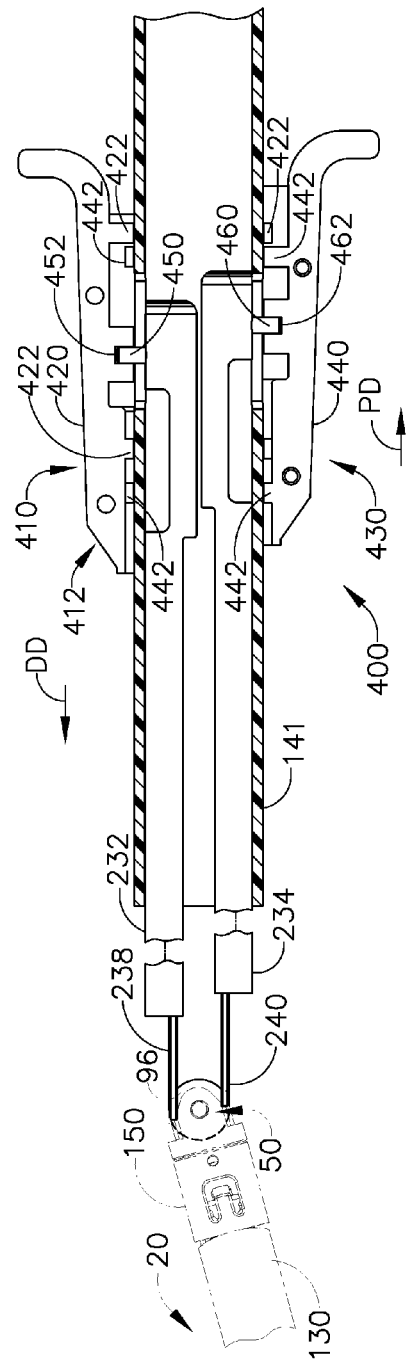
FIG. 22 is a cross-sectional plan view of the non-limiting articulation control system of FIGS. 17-21 with the end effector articulated in a first articulation direction.
Figure 23:
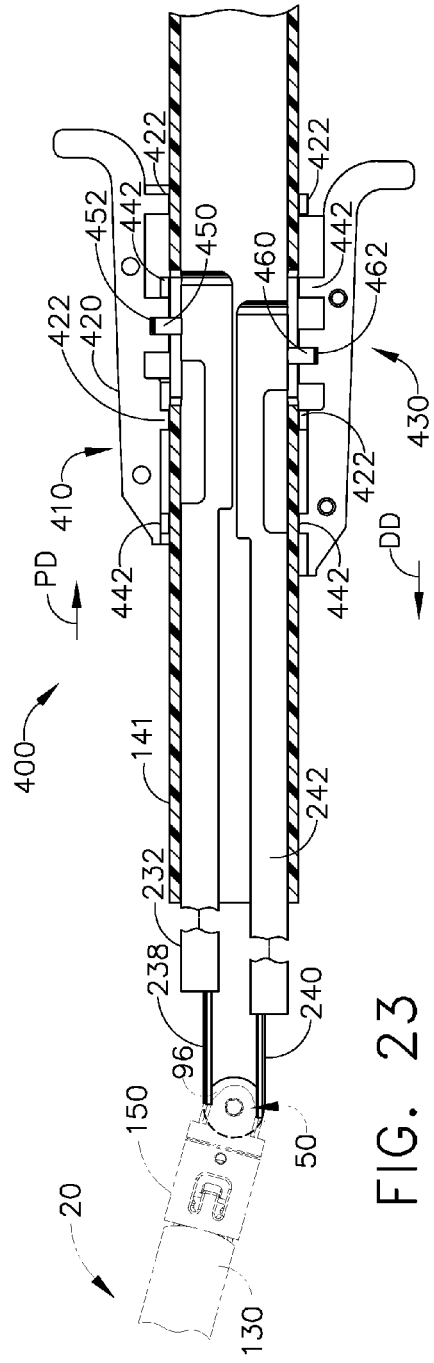
FIG. 23 is another cross-sectional plan view of the non-limiting articulation control system of FIGS. 17-22 with the end effector articulated in a second articulation direction.

The operation of the articulation control system 400 can be understood from reference to FIGS. 22 and 23. FIG. 22 illustrates articulation of the end effector 20 to the left of the articulation pivot 50. To accomplish this range of articulation, the clinician axially moves the right nozzle portion 412 in the distal direction "D-D" and the left nozzle portion 430 in the proximal direction "PD" which causes the right articulation rod 232 and left articulation rod 234 to move the end effector to the left about the articulation point 50. Such movement of the right and left articulation rods 232, 234 result in the application of a pushing motion to the boss 96 by the right articulation band 238 and a pulling motion to the boss 96 by the left articulation band 240 which results in the articulation of the end effector 20 as shown. FIG. 23 illustrates articulation of the end effector 20 to the right of the articulation pivot 50. To accomplish this range of articulation, the clinician axially moves the right nozzle portion 412 in the proximal direction "PD" and the left nozzle portion 430 in the distal direction "DD" which causes the right articulation rod 232 and left articulation rod 234 to move the end effector 20 to the right about the articulation point 50. Such movement of the right and left articulation rods 232, 234 result in the application of a pushing motion to the boss 96 by the left articulation band 240 and a pulling motion to the boss 96 by the right articulation band 238 which results in the articulation of the end effector 20 as shown. Although the articulation assembly 230 as described above employs two elongated articulation rods or members, in alternative embodiments, only one elongated articulation member is employed.

Figure 24:
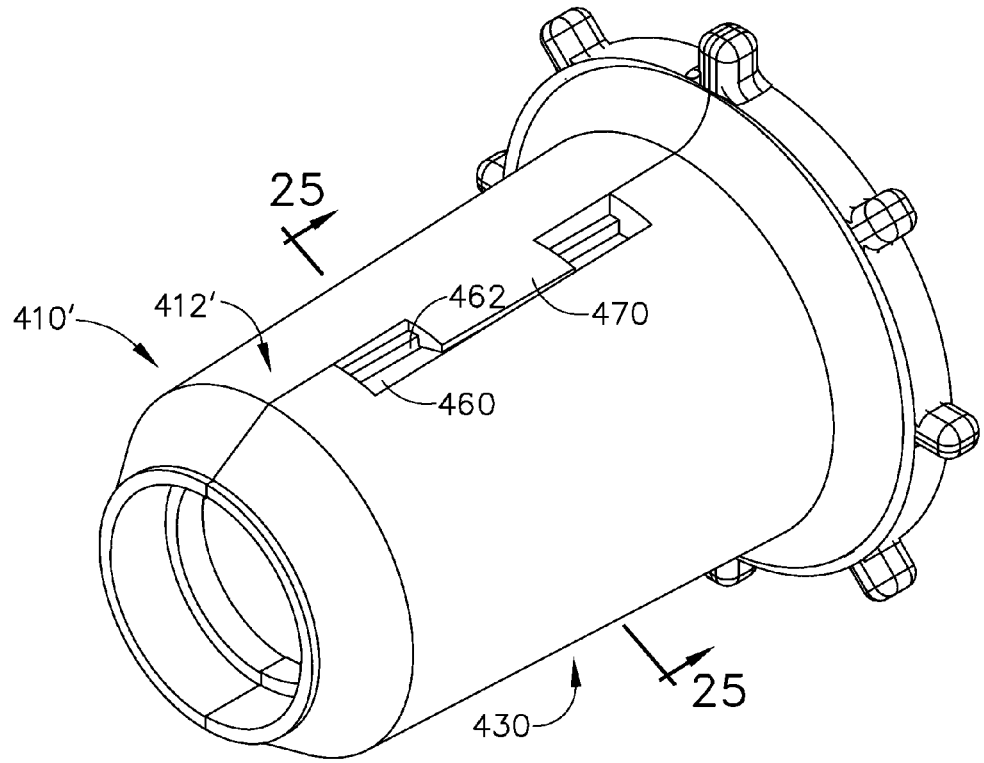
FIG. 24 is a perspective view of a non-limiting nozzle assembly embodiment of another form of the present invention.
Figure 25:
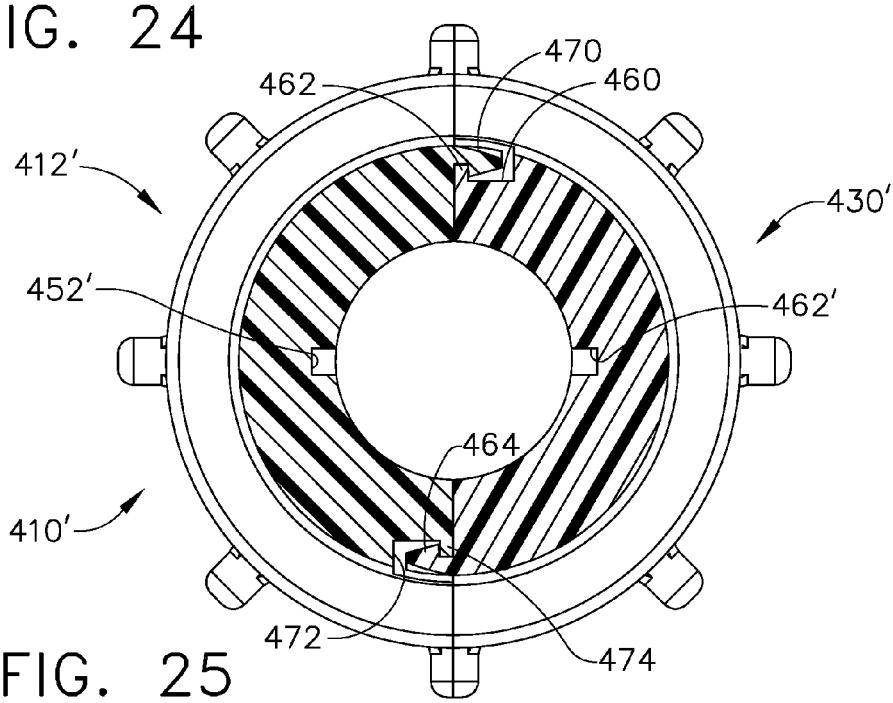
FIG. 25 is a cross-sectional view of the nozzle assembly of FIG. 24 taken along line 25-25 in FIG. 24.

FIGS. 24 and 25 illustrate an alternative nozzle embodiment 410' that may be employed instead of the nozzle embodiment 410 described above. In this embodiment, the nozzle 410' is fabricated from a right nozzle portion 412' that is axially movable relative to a left nozzle portion 430'. As can be seen in those Figures, the left nozzle portion 430' has a left axial opening 460 therein that defines a left axial ledge 462 that is adapted to be slidably engaged by a right latch portion 470. Likewise the right nozzle portion 412 has a right axial opening 472 that has a right axial ledge 474 that is adapted to be slidably engaged by a left latch portion 464. Such arrangement serves to join the right nozzle portion 412' to the left nozzle portion 430 to each other about the proximal closure shaft 141 while enabling those portions to move axially relative to each other. The right nozzle portion 412' has a right aperture 452' therein for receiving the right pivot pin 450 therein and the left nozzle portion 430' has a left aperture 462' therein for receiving the left pivot pin 460 therein. The alternative nozzle 410' is otherwise operated in the manner described above to articulate the end effector 20 about the articulation pivot 50 and articulation axis B-B.

FIGS. 26-33 illustrate another non-limiting articulation control system embodiment of the present invention generally designated as 500. Those components that are the same as the components employed in the above-described embodiments will be labeled with the same element numbers and those of ordinary skill in the art can refer to the disclosure set forth hereinabove that explains their construction and operation. In at least one embodiment, the articulation control system 500 includes an articulation nozzle 510 that is fabricated in multiple pieces. For example, the articulation nozzle 510 has a right nozzle portion 512 that is configured to be attached to a left nozzle portion 530. See FIG. 29. In at least one non-limiting embodiment, the right nozzle portion 512 may be provided with attachment posts 513 formed thereon that are sized to be frictionally received in corresponding attachment apertures (not shown) in the left nozzle portion 530. The right nozzle portion 512 may likewise have attachment apertures 515 therein that are sized to frictionally engage corresponding attachment posts 531 on the left nozzle portion 530 to couple the right and left nozzle portions 512, 530 together. See FIG. 29. Other fastening arrangements such as adhesive, welding, mechanical fasteners, snap features, etc. may be used to attach the right and left nozzle portions together. In various non-limiting embodiments, the right nozzle portion 512 has a proximal end 514 with actuation buttons or protrusions 516 formed thereon. The right nozzle portion 512 further has a distal end 517 that has a key 518 formed thereon for receipt within a key opening 519 in the proximal closure tube segment 141 to non-rotatably affix the right nozzle portion 512 to the proximal closure tube segment 141. Similarly, the left nozzle portion 530 has a proximal end 534 with actuation buttons or protrusions 516 formed thereon. The left nozzle portion 530 further has a distal end 537 that has a key 538 formed thereon for receipt in a key opening 539 in the proximal closure tube segment 141 to non-rotatably affix the left nozzle portion 530 to the proximal closure tube segment 141. See FIGS. 31-33.

Figure 29:
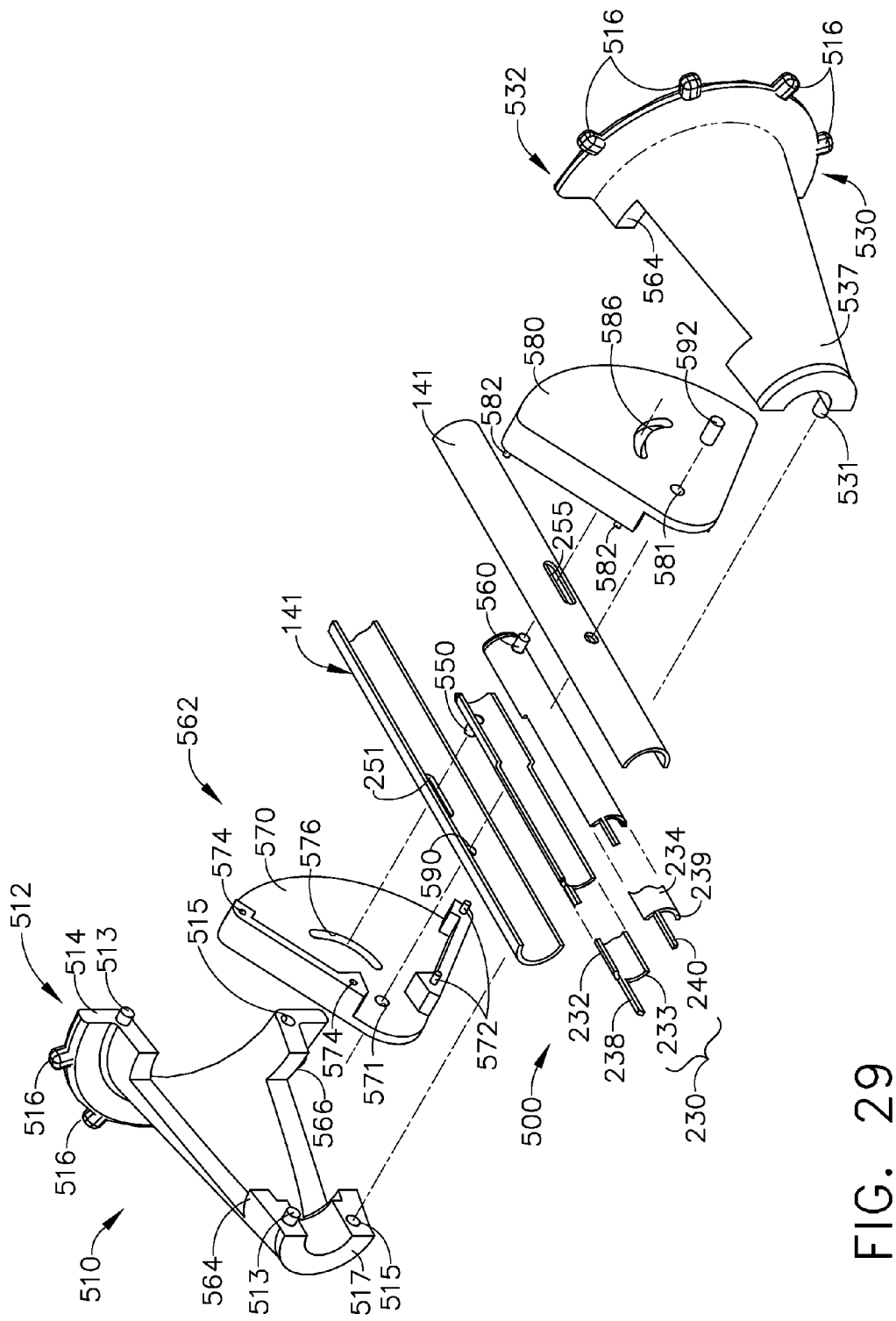
FIG. 29 is an exploded assembly view of the non-limiting articulation control system of FIGS. 26-28.
Figure 30:
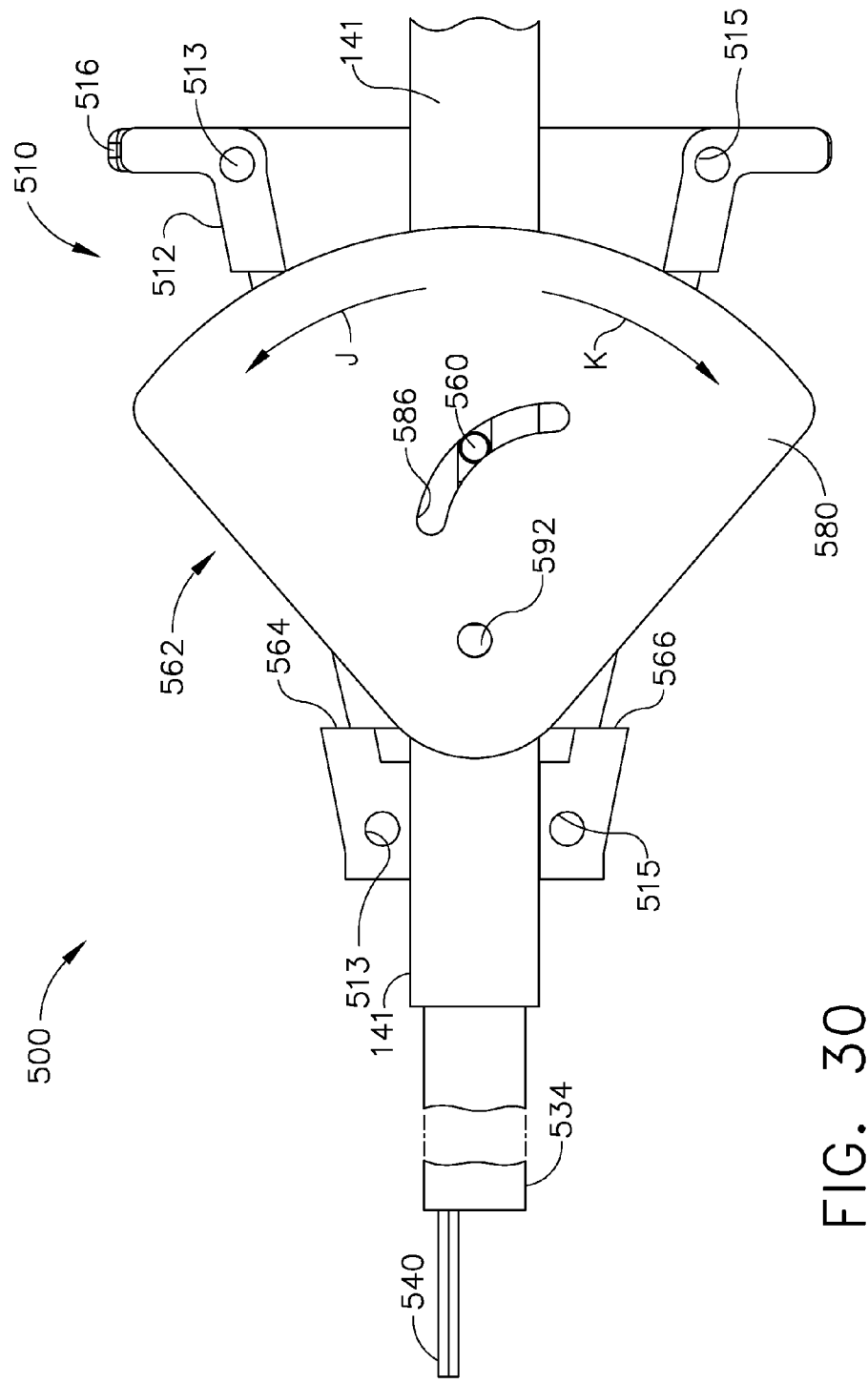
FIG. 30 is a side elevation view of a portion of the non-limiting articulation control system of FIGS. 26-29.

In at least one non-limiting embodiment, the articulation control system 500 includes an articulation assembly 230. In at least one embodiment, the articulation assembly 230 may comprise a right articulation rod 232 and a left articulation rod 234. The right and left articulation rods 232, 234 may be configured as shown in FIG. 29 and be fabricated from stainless steel or other suitable material. The right and left articulation rods 232, 234 when movably supported within the proximal closure tube segment 141 as illustrated, serve to define a centrally disposed elongate slot 236 that is configured to accommodate the axial movement of the firing bar 180. A right articulation band 238 protrudes distally from a distal end 233 of the right articulation rod 232 and a left articulation band 240 protrudes distally from the distal end 239 of the left articulation rod 234. In various embodiments, the articulation bands 238, 240 are attached to the boss 96. For example, the bands 238, 240 may be pivotally pinned to the boss 96. The right and left articulation rods 232, 234 are slidably inserted into the hollow proximal closure tube segment 141. The right articulation rod 232 has a right pivot pin 550 that is attached thereto and protrudes laterally therefrom through a right slot 251 in the proximal closure tube segment 141. Similarly, the left articulation rod 234 has a left pivot pin 560 that is attached thereto and protrudes laterally therefrom through a left slot 255 in the proximal closure tube segment 141.

In at least one non-limiting embodiment, the articulation control 500 includes an actuator assembly 562 that protrudes through openings 564, 566 in the nozzle 510 and is selectively pivotable about an actuator axis H-H that is substantially transverse to the longitudinal axis A-A. In various forms, the actuator assembly 562 comprises a first actuator portion 570 that is coupled to a second actuator portion 580. The first actuator portion 570 has a pivot hole 571 therethrough that is adapted to pivotally receive a first actuator pin 590 that is coupled to the proximal closure tube segment 141. See FIGS. 28 and 29. Similarly, the second actuator portion 580 has a pivot hole 581 therethrough that is adapted to pivotally receive a second actuator pin 592 that is coupled to the proximal closure tube segment 141. The first and second actuator pins 590, 592 serve to define the actuator axis H-H that is substantially transverse to the longitudinal axis A-A and about which the actuator assembly 562 may pivot. The first actuator portion 570 may be attached to the second actuator portion 580 by a variety of methods. In the illustrated version, for example, the first actuator portion 570 has a pair of attachment posts 572 that are sized to be frictionally received within corresponding attachment holes (not shown) in the second actuator portion 580. Likewise, the second actuator portion 580 may have attachment posts 580 that are sized to be frictionally received within attachment holes 574 in the first actuator portion, such that when the first and second actuator portions 570, 580 are joined together, the form the actuator assembly 562. However, the first and second actuator portions 570, 580 may be coupled together using any suitable means such as by adhesive, snap features, fasteners, etc.

Figure 28:
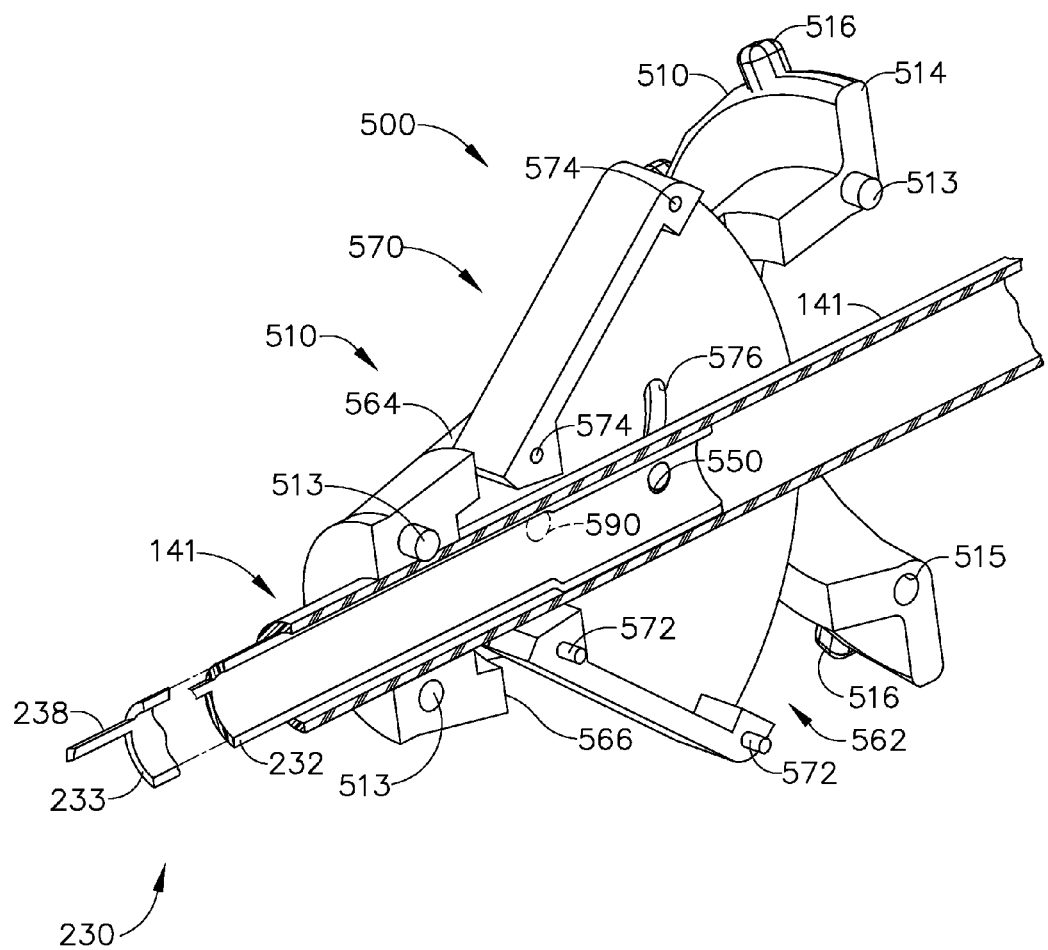
FIG. 28 is another perspective view of the portion of the non-limiting articulation control system embodiment of FIG. 27 with a portion shown in cross-section.

As can be seen in FIGS. 28 and 29, the first actuator portion 570 operably interfaces with the first articulation rod 232 to effectuate axial movement thereof within the proximal closure tube segment 141 by means of a first cam slot 576 that is configured to receive a portion of the right pivot pin 550 therein. Thus, by pivoting the first actuator portion 570 about the actuator axis H-H, the interaction between the first cam slot 576 and the right pivot pin 550 will cause the first articulation rod 232 to axially move within the proximal closure tube segment 141. Similarly, the second actuator portion 580 operably interfaces with the second articulation rod 234 to effectuate axial movement thereof within the proximal closure tube segment 141 by means of a second cam slot 586 that is configured to receive a portion of the left pivot pin 560 therein. Thus, when the second actuator portion 580 pivots about the actuator axis H-H, the interaction between the second cam slot 586 and the left pivot pin 560 will cause the second articulation rod 234 to axially move within the proximal closure tube segment 141.

Figure 26:
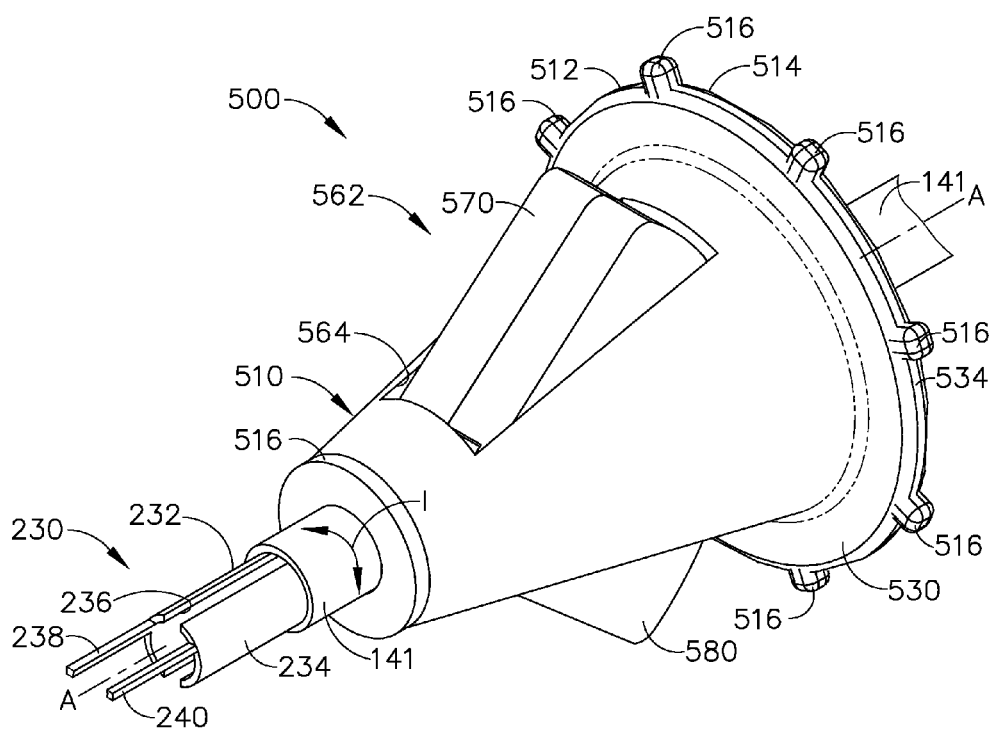
FIG. 26 is a perspective view of a non-limiting articulation control system embodiment of at least one other form of the present invention.
Figure 27:
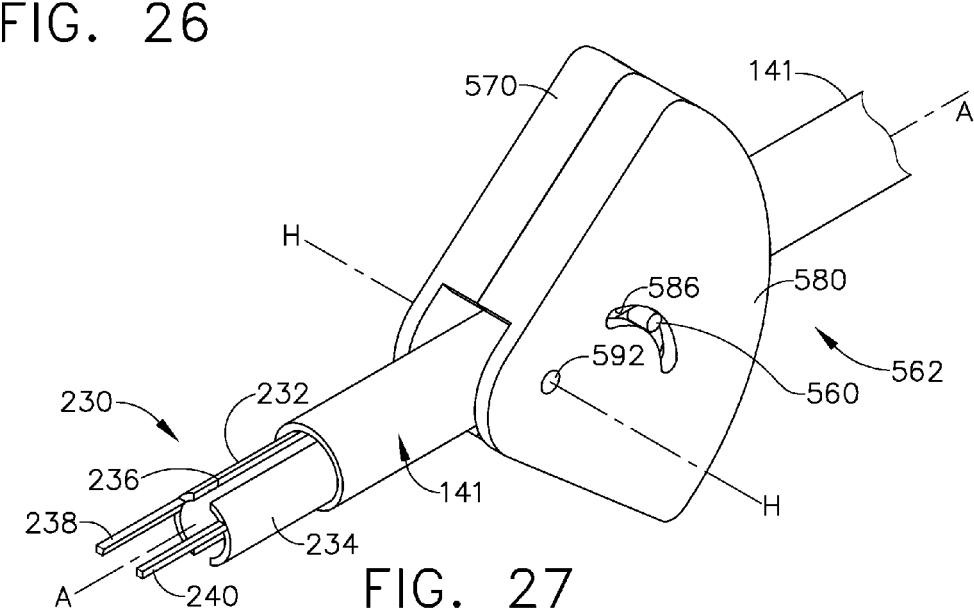
FIG. 27 is a perspective view of a portion of the non-limiting articulation control system embodiment of FIG. 26.
Figure 31:
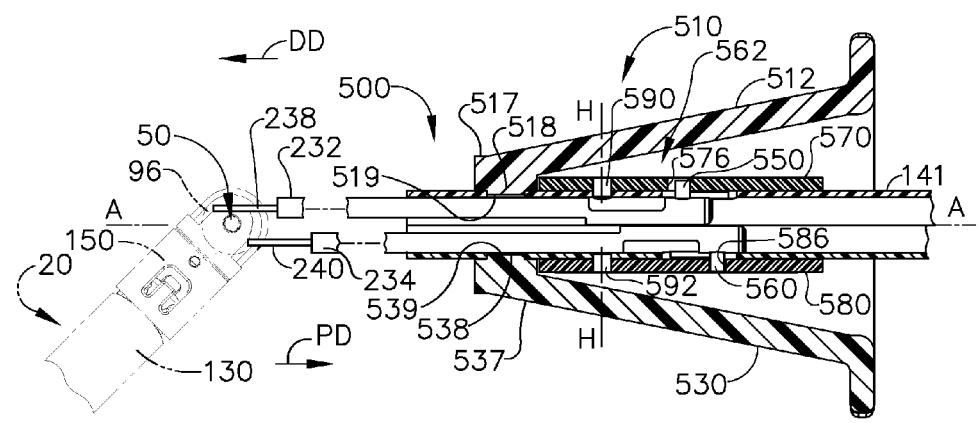
FIG. 31 is a cross-sectional plan view of the non-limiting articulation control system of FIGS. 26-30 with the end effector articulated in a first articulation direction.
Figure 32:
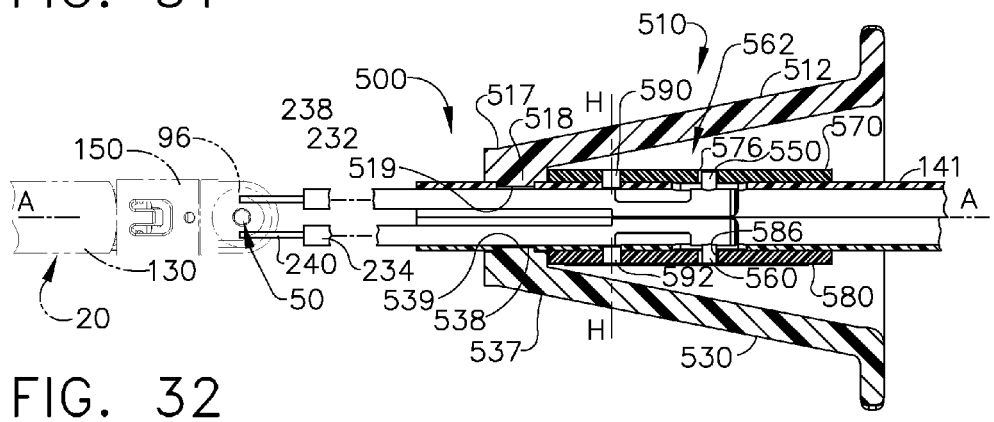
FIG. 32 is another cross-sectional plan view of the non-limiting articulation control system of FIGS. 26-31 with the end effector in an unarticulated orientation.
Figure 33:
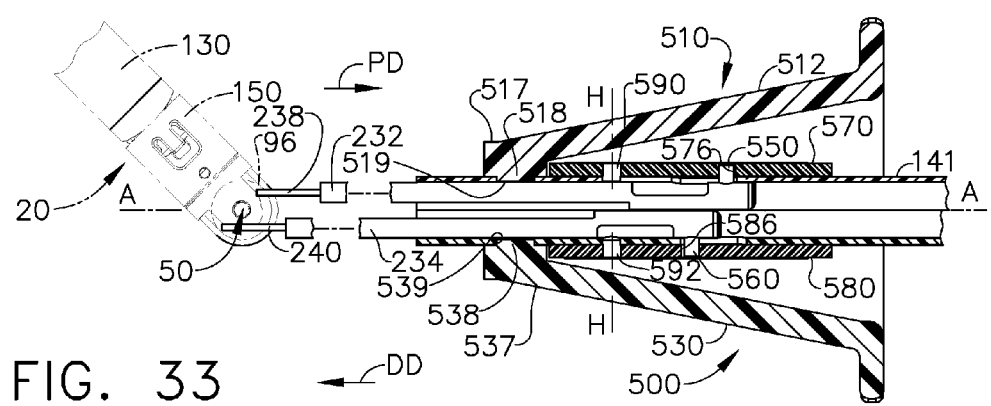
FIG. 33 is another cross-sectional plan view of the non-limiting articulation control system of FIGS. 26-32 with the end effector articulated in a second articulation direction.

The operation of the articulation control system 500 can be understood from reference to FIGS. 26 and 31-33. Turning first to FIG. 26, to rotate the proximal closure tube segment 141 and ultimately end effector 20 (shown in FIGS. 31-33) about the longitudinal axis AA, the clinician simply rotates the nozzle 510 about the longitudinal axis A-A as represented by arrow "I" in FIG. 26. FIG. 31 illustrates articulation of the end effector 20 to the left of the articulation pivot 50. To accomplish this range of articulation, the clinician simply pivots the actuator assembly 562 in the "J" direction (illustrated in FIG. 30) about the actuator axis H-H. Such movement of the actuator assembly 562 results in interaction between the right pivot pin 550 and the right cam slot 576 which results in the axial movement of the right articulation rod 232 in the distal direction "DD". Such movement of the actuator assembly 562 also results interaction between the left pivot pin 560 and the left cam slot 586 which simultaneously results in the axial movement of the left actuator rod 234 in the proximal direction "PD". Such movement of the right and left articulation rods 232, 234 result in the application of a pushing motion to the boss 96 by the right articulation band 238 and a pulling motion to the boss 96 by the left articulation band 240 which results in the articulation of the end effector 20 as shown. FIG. 33 illustrates articulation of the end effector 20 to the right of the articulation pivot 50. To accomplish this range of articulation, the clinician pivots the actuator assembly 562 in the "K" direction (shown in FIG. 30) about the actuator axis H-H. Such movement of the actuator assembly 562 results in interaction between the right pivot pin 550 and the right cam slot 576 which results in the axial movement of the right articulation rod 232 in the proximal direction "PD". Such movement of the actuator assembly 562 also results interaction between the left pivot pin 560 and the left cam slot 586 which simultaneously results in the axial movement of the left actuator rod 234 in the distal direction "DD". Such movement of the right and left articulation rods 232, 234 result in the application of a pushing motion to the boss 96 by the left articulation band 240 and a pulling motion to the boss 96 by the right articulation band 238 which results in the articulation of the end effector 20 as shown. Although the articulation assembly 230 as described above employs two elongated articulation rods or members, in alternative embodiments, only one elongated articulation member is employed.

FIGS. 34-42 illustrate another non-limiting articulation control system embodiment of the present invention, generally designated as 600. Those components that are the same as the components employed in the above-described embodiments will be labeled with the same element numbers and those of ordinary skill in the art can refer to the disclosure set forth hereinabove that explains their construction and operation. In this embodiment, the articulation control system 600 includes an articulation nozzle 610 that is fabricated in multiple pieces. For example, the articulation nozzle 610 has an upper nozzle portion 612 that is configured to be attached to a lower nozzle portion 630. See FIG. 38. In at least one non-limiting embodiment, the upper nozzle portion 612 may be provided with attachment posts (not shown) formed thereon that are sized to be frictionally received in corresponding attachment apertures 631 in the lower nozzle portion 630. Other fastening arrangements such as adhesive, mechanical fasteners, snap features, etc. may be used to attach the upper and lower nozzle portions 612, 630 together. In various non-limiting embodiments, the upper nozzle portion 612 has a proximal end 614 with actuation buttons or protrusions 616 formed thereon. Similarly, the lower nozzle portion 630 has a proximal end 634 with actuation buttons or protrusions 616 formed thereon.

Figure 38:
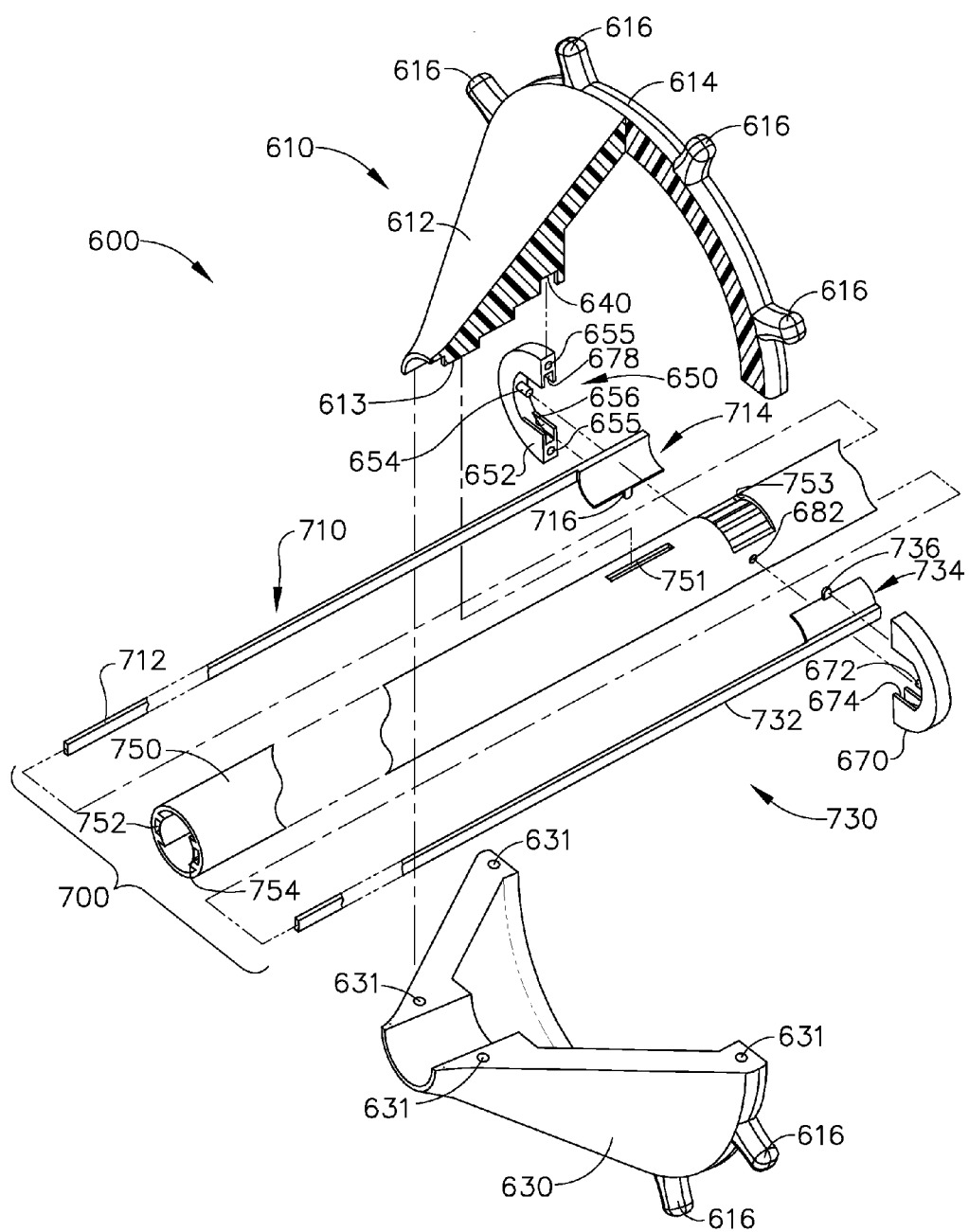
FIG. 38 is an exploded assembly view of the non-limiting articulation control system embodiment of FIGS. 34-37.

In at least one non-limiting embodiment, the articulation control system 600 includes an articulation assembly 700. In at least one embodiment, the articulation assembly 700 may comprise a right articulation band 710 and a left articulation band 730 that are received with a proximal closure tube segment 750. The right articulation band 710 has an elongated right band portion 712 and a proximal actuation portion 714. Similarly the left articulation band 730 has a left elongated band portion 732 and a proximal actuation portion 734. The right and left articulation bands 710, 730 may be fabricated from stainless steel or other suitable material. The proximal closure tube segment 750 comprises a hollow tube that may be fabricated from, for example, stainless steel or other suitable material. In at least one non-limiting embodiment, the hollow proximal closure shaft segment 750 has a right band passage 752 and a left band passage 754 formed in its wall. The center of the proximal closure tube segment 750 provides a passage to accommodate the device's proximal frame or spine portion (not shown) as well as the firing bar (not shown) in the various manners described above. As illustrated in FIG. 38, the elongated right articulation band portion 712 is slidably supported within the right band passage 752 and the elongated left articulation band portion 732 is slidably supported in the left band passage 754. In various non-limiting embodiments, the articulation bands 712, 732 are attached to the boss 96. See FIGS. 40 and 42. For example, the bands 238, 240 may be pivotally pinned to the boss 96. The right and left articulation rods 232, 234 are slidably inserted into the hollow proximal closure tube segment 141. The right articulation rod 232 has a right pivot pin 550 that is attached thereto and protrudes laterally therefrom through a right slot 251 in the proximal closure tube segment 141. Similarly, the left articulation rod 234 has a left pivot pin 560 that is attached thereto and protrudes laterally therefrom through a left slot 255 in the proximal closure tube segment 141.

Figure 36:
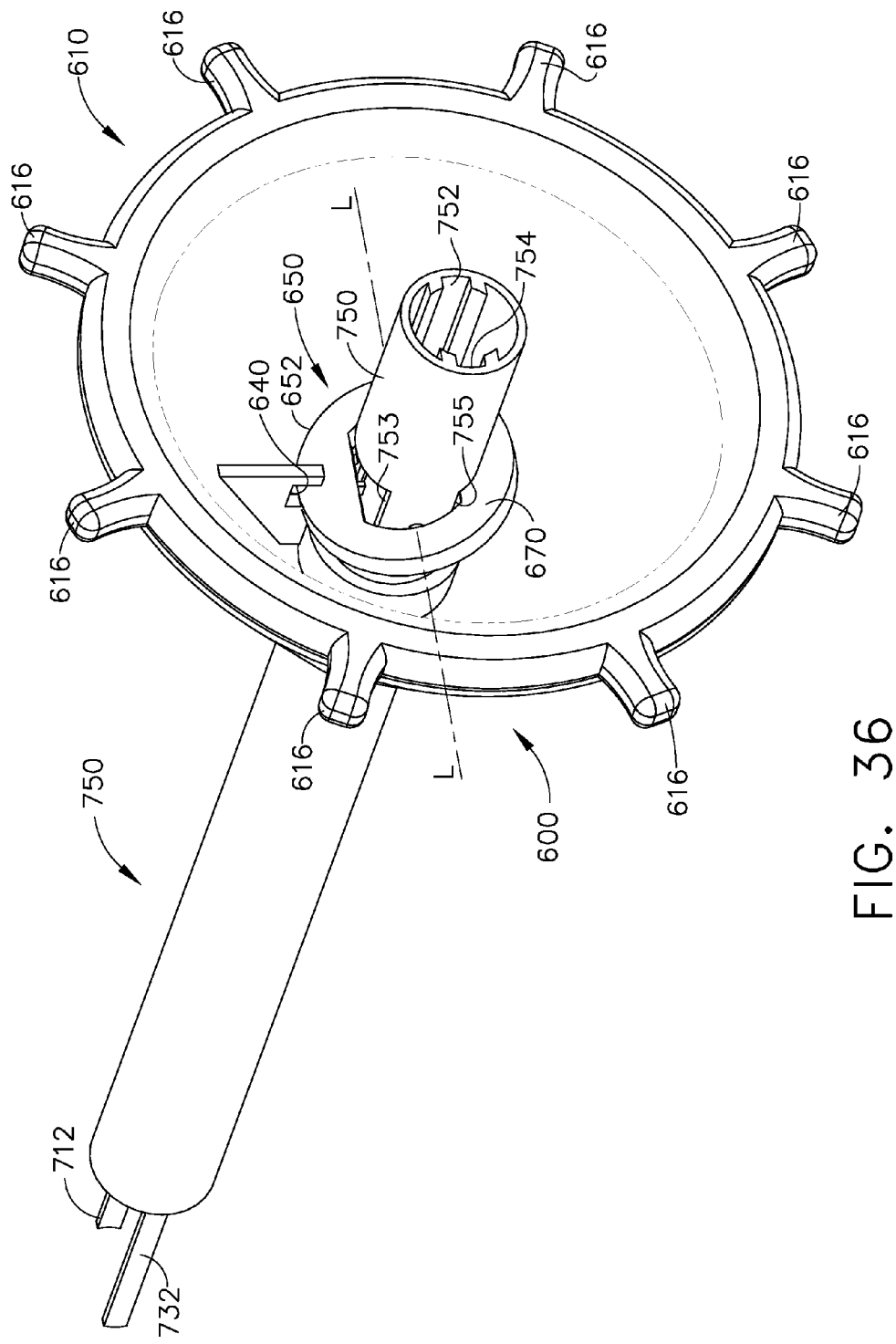
FIG. 36 is a rear perspective view of the non-limiting articulation control system embodiment of FIGS. 34 and 35.
Figure 37:
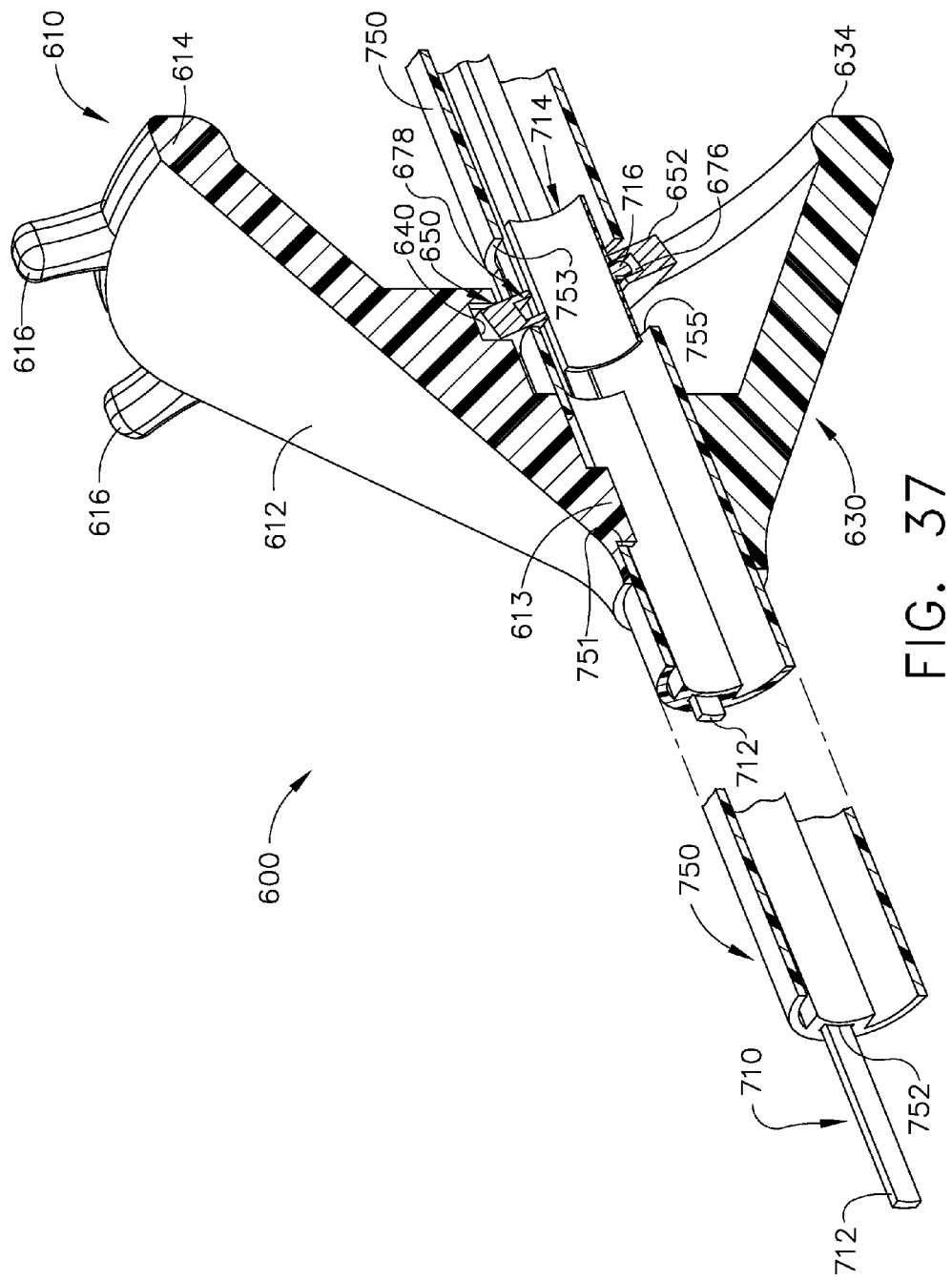
FIG. 37 is a cross-sectional perspective view of the non-limiting articulation control system embodiment of FIGS. 34-36.
Figure 39:
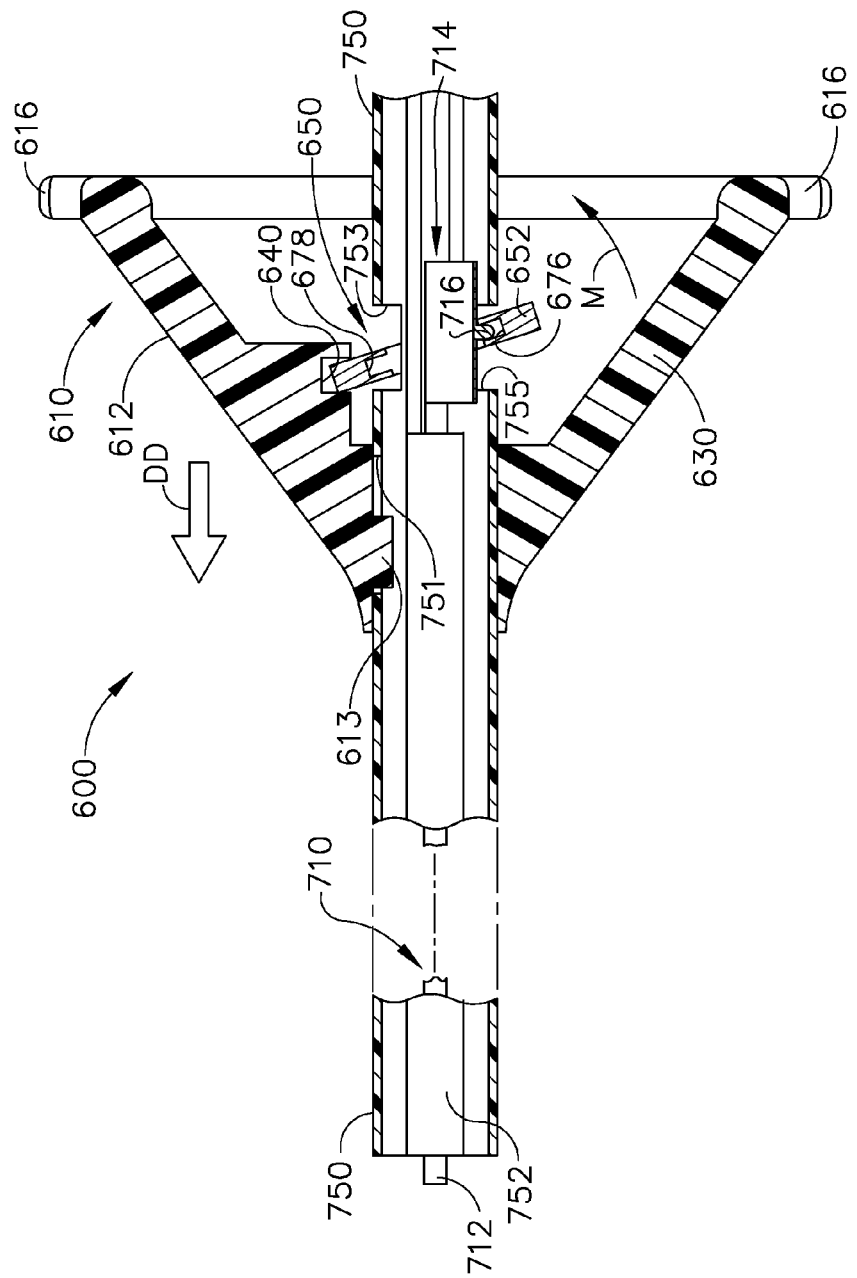
FIG. 39 is a cross-sectional view of the non-limiting articulation control system embodiment of FIGS. 34-38.

The nozzle 610 is non-rotatably affixed to the proximal closure shaft segment 750 such that rotation of the nozzle 610 about the longitudinal axis A-A will result in the rotation of the end effector 20 about the longitudinal axis A-A. In at least one non-limiting embodiment, the nozzle 610 has a key 613 that extends into a slot 751 in the proximal closure tube segment 750. See FIG. 38. Such arrangement serves to non-rotatably affix the nozzle 610 to the proximal closure tube segment 750 while facilitating the axial movement of the nozzle 610 relative thereto. As can also be seen in FIGS. 37 and 38, the upper nozzle portion 612 further has an actuation notch 640 formed therein that is configured to operably engage an actuation pivot member or pivot plate 650. In at least one non-limiting embodiment, the pivot plate 650 comprises a right pivot plate portion 652 and a left pivot plate portion 670. The right pivot portion has a pivot pin 654 formed therein that is adapted to be pivotally received within a pivot hole 780 in the proximal closure tube segment 750. See FIG. 42. Similarly, the left pivot plate portion 670 has a right pivot pin 672 formed therein that is adapted to be pivotally received within a pivot hole 682 in the proximal closure tube segment 750. The right and left pivot pins 654, 672 are coaxially aligned with each other to define an actuation axis L-L about which the pivot plate 650 may pivot and which is substantially transverse to the longitudinal axis "L-L". The right and left pivot plate portions 650, 670 are attached together by posts (not shown) and holes 655 that are designed for frictional engagement. The right and left pivot plate portions 650, 670 may also be attached together by adhesive or other suitable fastener arrangement. As can be seen in FIGS. 36, 37, and 39 the proximal closure tube segment 750 has upper and lower clearance slots 753, 755 therein to facilitate pivotal travel of the pivot plate 650 about the actuation axis L-L (FIG. 36).

As can be further seen in FIGS. 37-40 and 41, the right pivot plate portion 650 has a lower right actuation slot 656 that is configured to align with a corresponding lower left actuation slot 674 in the left pivot plate portion 670 to form a lower actuation slot 676 in the pivot plate 650 for receiving and operably engaging an actuator tab 716 formed on the actuator portion 714 of the actuator band assembly 710. The right pivot plate portion 650 has an upper right articulation slot 658 that is configured to align with a corresponding upper left articulation slot (not shown) in the left pivot plate portion 670 to form an upper articulation slot 678 in the pivot plate 650 for receiving and operably engaging an actuator tab 736 formed on the actuator portion 734 of the actuator band assembly 730.

Figure 40:
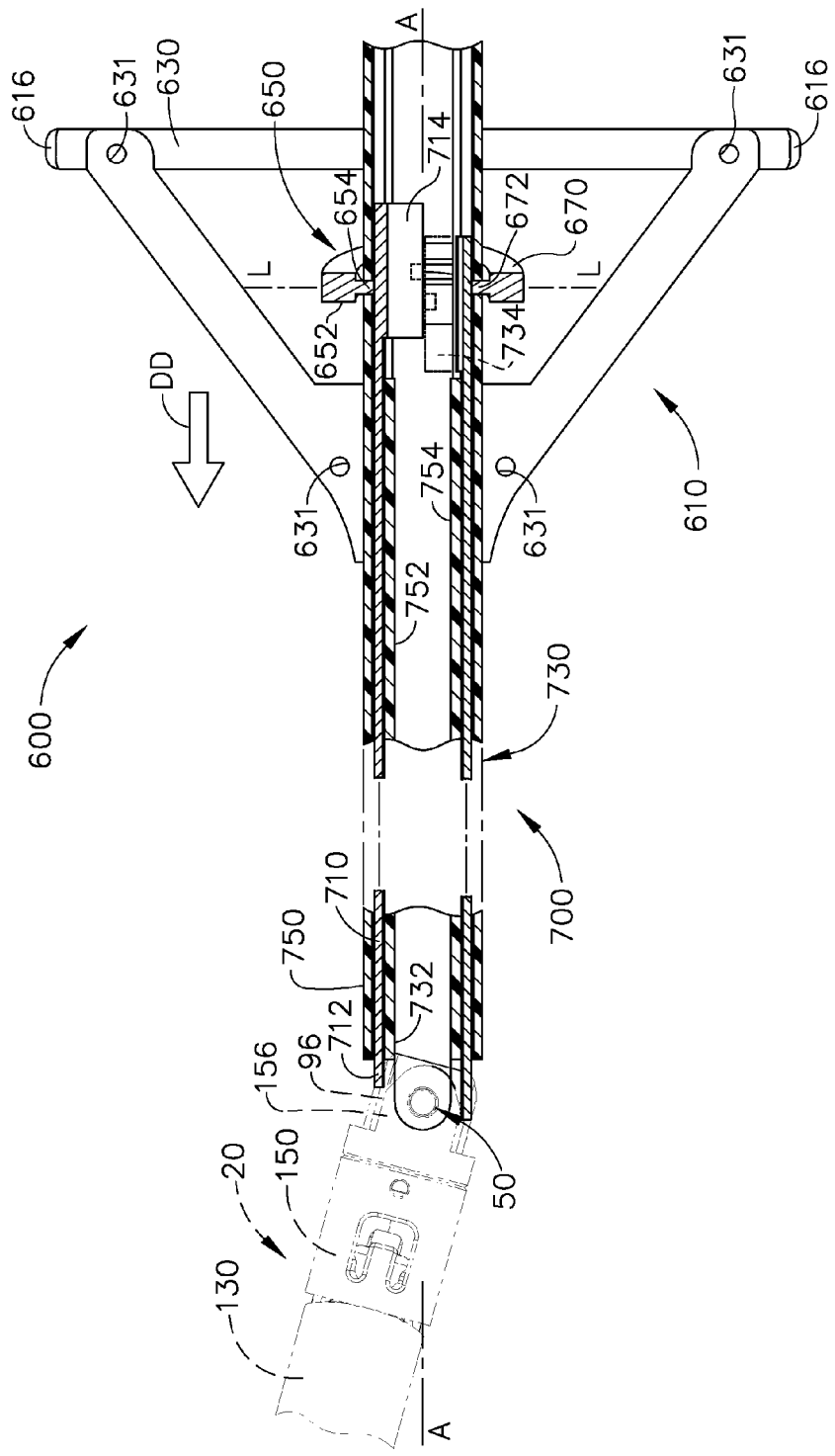
FIG. 40 is another cross-sectional view of the non-limiting articulation control system embodiment of FIGS. 34-39 with the end effector articulated in a first articulation direction.
Figure 41:
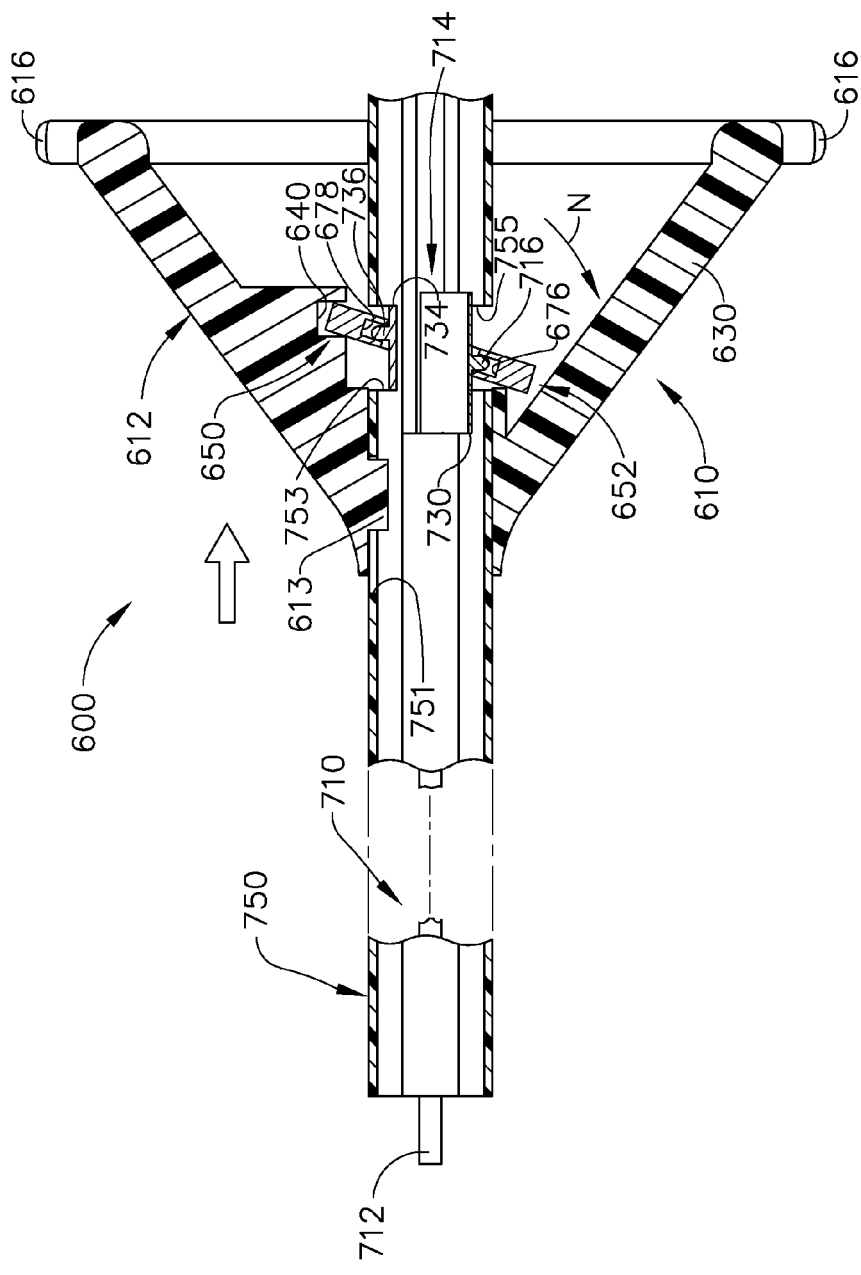
FIG. 41 is another cross-sectional view of the non-limiting articulation control system embodiment of FIGS. 34-40.
Figure 42:
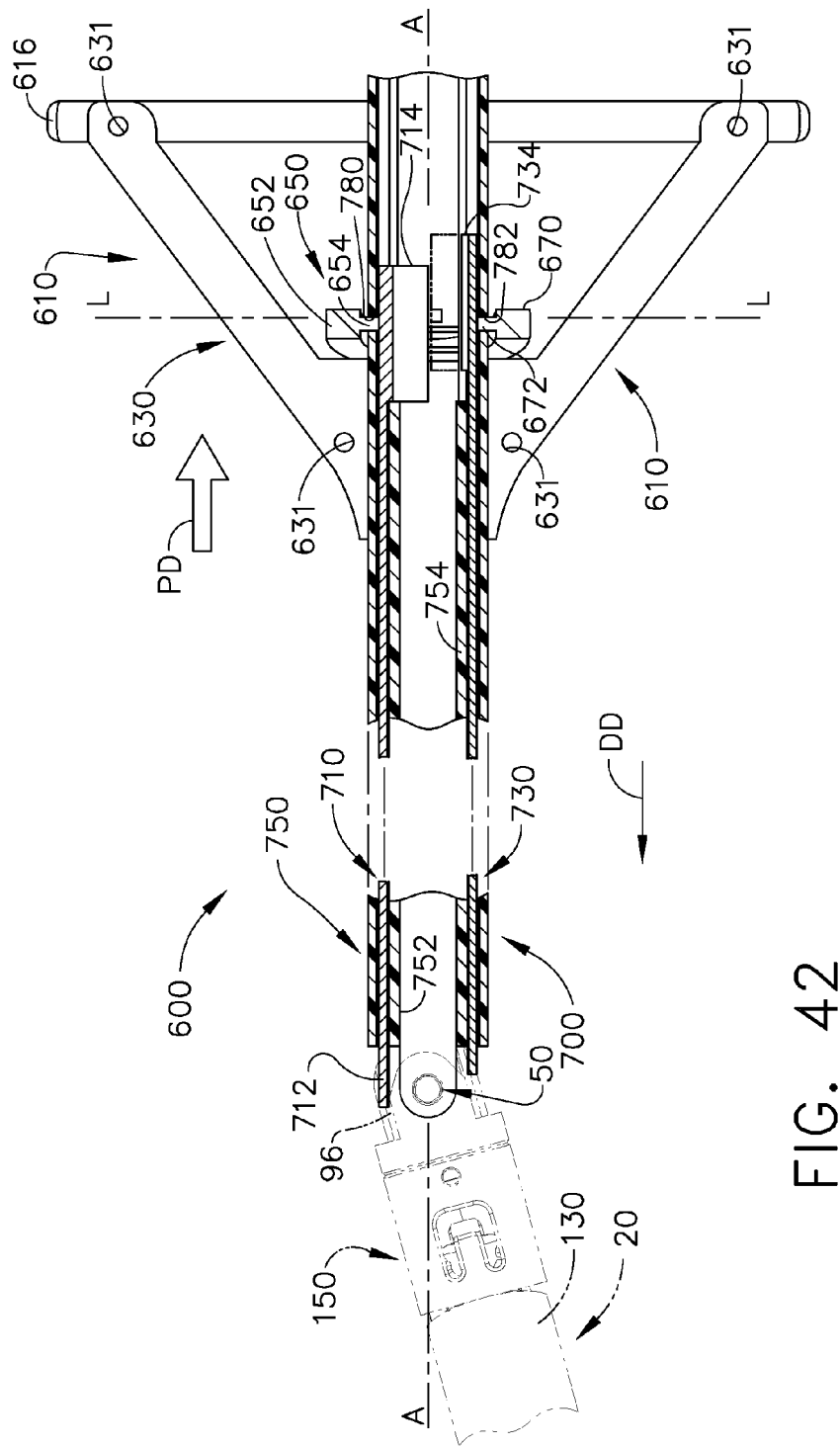
FIG. 42 is a cross-sectional view of the non-limiting articulation control system embodiment of FIGS. 34-41 with the end effector articulated in a second articulation direction.
Figure 43:
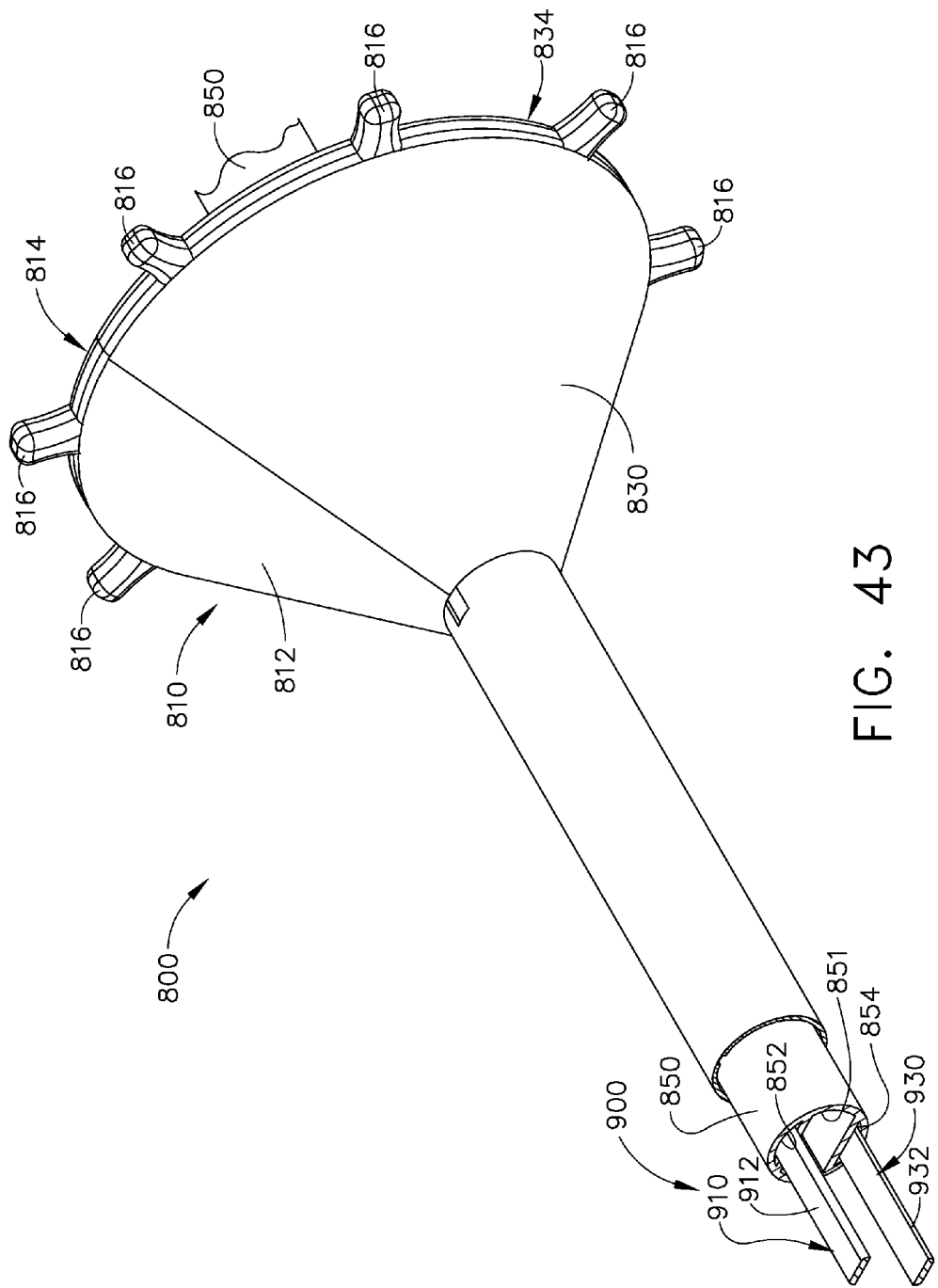
FIG. 43 is a perspective view of another non-limiting articulation control system embodiment of the present invention.
Figure 44:
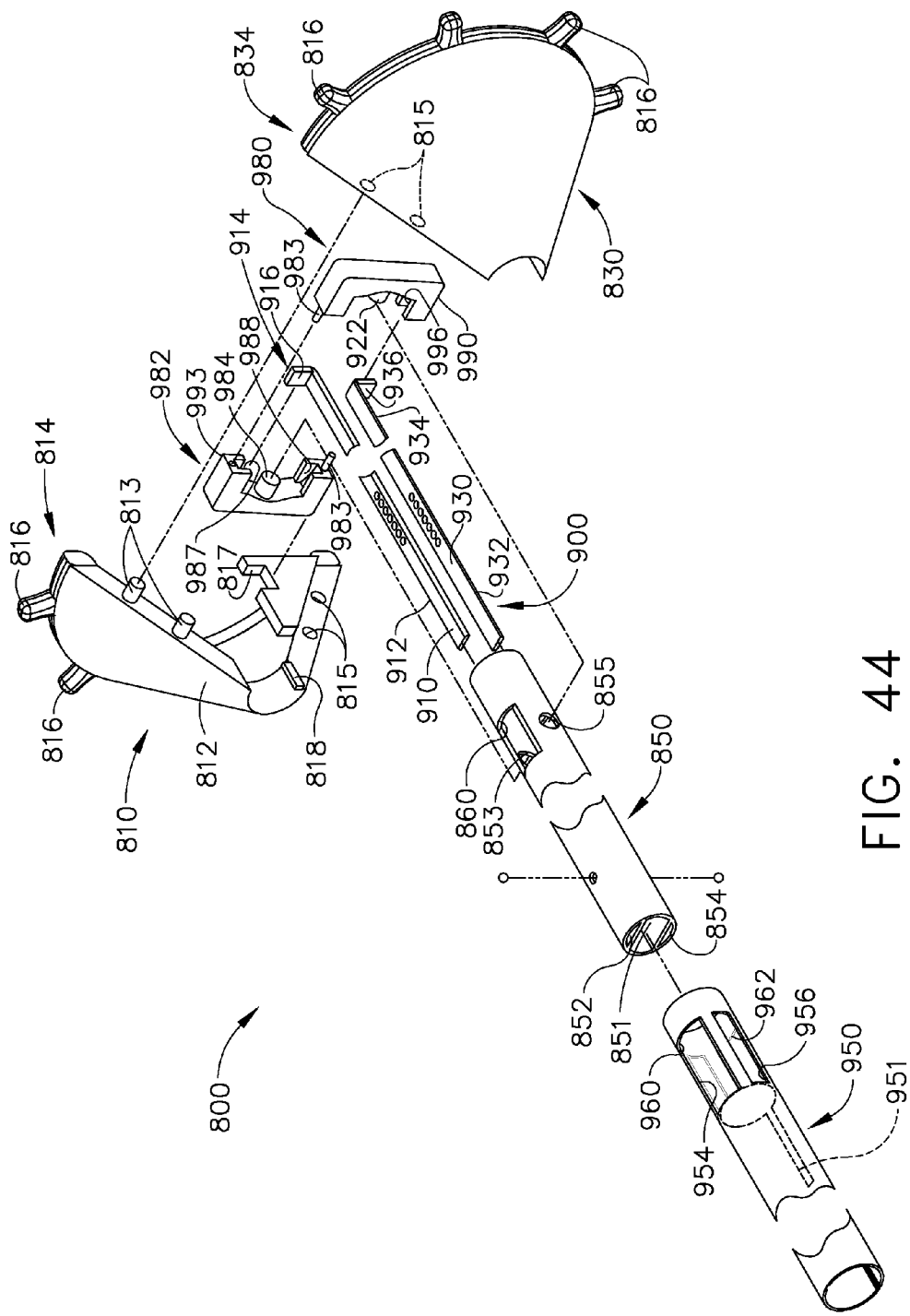
FIG. 44 is an exploded assembly view of the non-limiting articulation control system embodiment of FIG. 43.

The operation of the articulation control system 600 can be understood from reference to FIGS. 39-42. Turning first to FIGS. 39 and 40, to pivot the end effector 20 in the right direction about the pivot point 50, the clinician axially pushes the nozzle 610 axially in the distal direction "DD". Such movement of the nozzle 610 in the distal direction "DD" causes the pivot plate 650 to pivot about the actuation axis L-L in the "M" direction (FIG. 39) thereby pushing the left articulation band assembly 730 in the distal direction "DD" and pulling the right articulation band assembly 750 in the proximal direction "PD". Such axial movement of the nozzle 610 and the right and left articulation band assemblies 710, 730 result in the application of a pushing motion to the boss 96 by the left articulation band assembly 730 and a pulling motion to the boss 96 by the right articulation band assembly 710 which results in the articulation of the end effector 20 as shown in FIG. 40. Likewise, to pivot the end effector 20 about the pivot point 50 in the left direction (FIG. 42), the clinician pulls the nozzle 610 in the proximal direction "PD". Such movement of the nozzle 610 in the proximal direction "PD" causes the pivot plate 650 to pivot about the actuation axis L-L in the "N" direction (FIG. 41) thereby pushing the right articulation band assembly 710 in the distal direction "DD" and pulling the left articulation band assembly 750 in the proximal direction "PD". Such axial movement of the nozzle 610 and the right and left articulation band assemblies 710, 730 result in the application of a pushing motion to the boss 96 by the right articulation band assembly 710 and a pulling motion to the boss 96 by the left articulation band assembly 730 which results in the articulation of the end effector 20 as shown in FIG. 42. To rotate the end effector 20 about the longitudinal axis A-A, the clinician simply rotates the nozzle 610 about the longitudinal axis A-A. Such action may be accomplished by a portion of eth same hand that is supporting the handle of the instrument. Although the articulation assembly 230 as described above employs two elongated articulation rods or members, in alternative embodiments, only one elongated articulation member is employed.

FIGS. 43-50 illustrate another articulation control system embodiment of the present invention, generally designated as 800. Those components that are the same as the components employed in the above-described embodiments will be labeled with the same element numbers and those of ordinary skill in the art can refer to the disclosure set forth hereinabove that explains their construction and operation. In at least one non-limiting embodiment, the articulation control system 800 includes an articulation nozzle 810 that is fabricated in multiple pieces. For example, the articulation nozzle 810 has a first nozzle portion 812 that is configured to be attached to a second nozzle portion 830. See FIGS. 44-46. In at least one non-limiting embodiment, the right nozzle portion 812 and left nozzle portion 830 are attached together by a collection of posts 813 that are frictionally received in corresponding apertures 815. Other fastening arrangements such as adhesive, mechanical fasteners, snap features, etc. may be used to attach the first and second nozzle portions 812, 830 together. In various non-limiting embodiments, the first nozzle portion 812 has a proximal end 814 with actuation buttons or protrusions 816 formed thereon. Similarly, the second nozzle portion 830 has a proximal end 834 with actuation buttons or protrusions 816 formed thereon.

In at least one non-limiting embodiment, the articulation control system 800 includes a selectively lockable articulation assembly 900. In at least one non-limiting embodiment, the articulation assembly 900 may comprise a right articulation band 910 and a left articulation band 930 that are received with a spine segment 850 that is affixed to the instrument handle (not shown). The right articulation band 910 has an elongated right band portion 912 and a proximal actuation portion 914 that has a right actuation tab 916 formed thereon. Similarly the left articulation band 930 has a left elongated band portion 932 and a proximal actuation portion 934 that has a left actuation tab 936 formed thereon. The right and left articulation bands 910, 930 may be fabricated from stainless steel or other suitable material.

Figure 47:
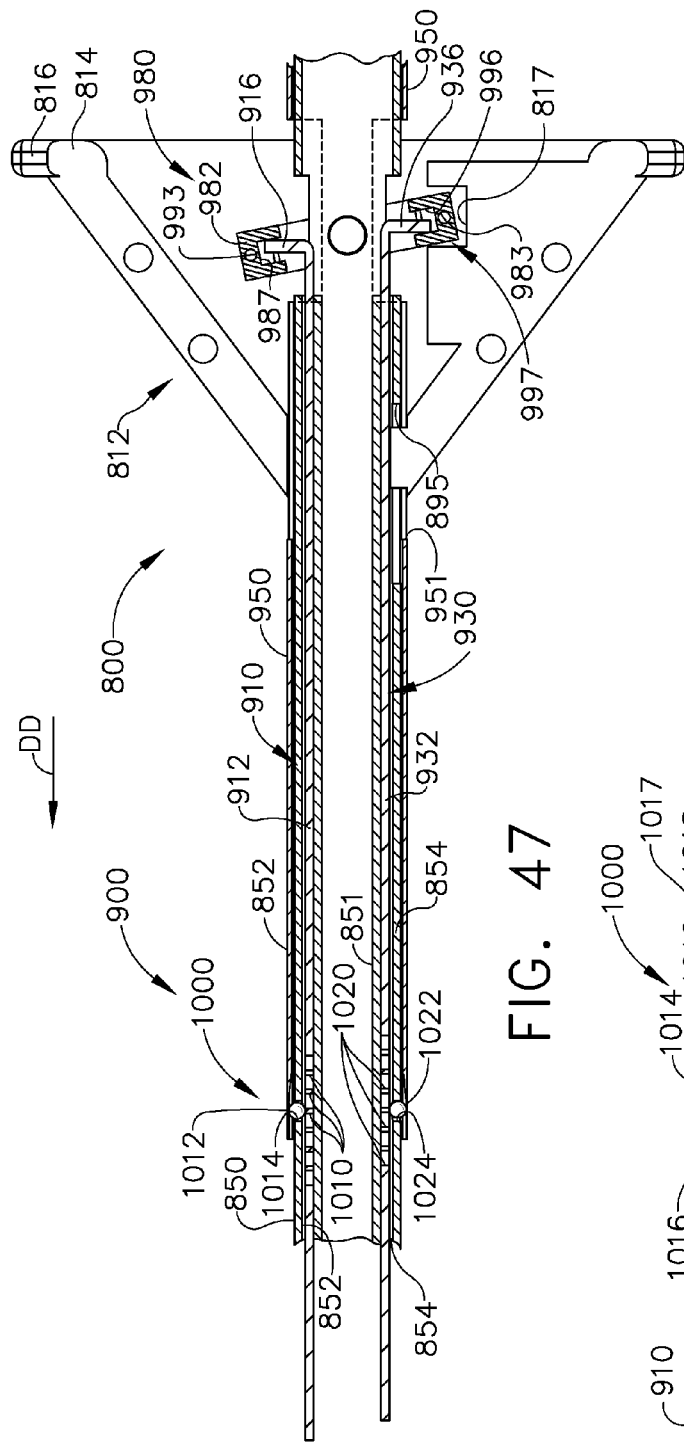
FIG. 47 is a cross-sectional view of the non-limiting articulation control system embodiment of FIGS. 43-46 in an unlocked position.

In various non-limiting embodiments, the spine segment 850 comprises a hollow tube that may be fabricated from, for example, stainless steel or other suitable material. In at least one non-limiting embodiment, the hollow spine segment 850 has a right band passage 852 and a left band passage 854 formed in its wall. The center of the spine segment 850 provides a passage 851 sized and configured to accommodate the device's proximal frame or spine portion 100 (shown in FIG. 2) as well as the firing bar 180 (shown in FIG. 2) in the various manners described above. As illustrated in FIG. 47, the elongated right articulation band portion 912 is slidably supported within the right band passage 852 and the elongated left articulation band portion 932 is slidably supported in the left band passage 854. In various non-limiting embodiments, the articulation bands 912, 932 are attached to the boss 96 of the end effector frame 90 as was discussed above.

As can be seen in FIGS. 44-47 and 49, in at least one non-limiting embodiment, the right and left actuation tabs 916, 936 are configured for operable engagement with an actuation or pivot plate 980. In various embodiments, the pivot plate 980 comprises a first pivot plate portion 982 and a second pivot plate portion 990. The first pivot plate portion 982 has a first pivot pin 984 formed thereon that is adapted to be pivotally received within a first pivot hole 853 in the spine segment 850. See FIGS. 44 and 46. Similarly, the second pivot plate portion 990 has a second pivot pin 992 formed thereon that is adapted to be pivotally received within a second pivot hole 852 in the spine segment 850. The first pivot pin 984 also extends through an elongated first slot 954 in a proximal closure tube segment 950. Similarly the second pivot pin 992 extends through an elongated second slot 956 in the proximal closure tube segment 950. Such arrangement enables the proximal closure tube segment 950 to move axially on the spine segment 850 while facilitating pivotal travel of the pivot plate 980 relative thereto. The first and second pivot pins 984, 992 are coaxially aligned with each other to define an actuation axis N-N about which the pivot plate 980 may pivot and which is substantially transverse to the longitudinal axis "A-A". See FIG. 45. The first and second pivot plate portions 982, 990 are attached together by posts 983 and holes 993 that are designed for frictional engagement. The first and second pivot plate portions 982, 990 may also be attached together by adhesive, welding, snap features or other suitable fastener arrangements.

As can be seen in FIG. 49, the spine segment 850 has a right tab slot 860 through which right actuator tab 916 extends. The spine segment 850 further has a left tab slot 862 through which the left articulation tab 936 extends. In addition, the right actuator tab 916 extends through a right slot 960 in the proximal closure tube segment 950 and the left actuator tab 936 extends through a left slot 962 in the proximal closure tube segment 950. As can be further seen in FIGS. 44-47, the first pivot plate portion 982 has a right actuation slot 987 that is configured to align with a corresponding right actuation slot (not shown) in the second pivot plate portion 990 to form a right articulation slot 995 in the pivot plate 980 for receiving and operably engaging the right actuator tab 916 therein. Similarly, the right pivot plate portion 982 has a left actuation slot 988 that is configured to align with a corresponding left actuation slot 996 in the second pivot plate portion 990 to form a left articulation slot 997 in the pivot plate 980 for receiving and operably engaging the left actuator tab 936 therein.

In various non-limiting embodiments, the articulation nozzle 810 is non-rotatably affixed to a proximal closure shaft segment 950 such that rotation of the articulation nozzle 610 about the longitudinal axis A-A will result in the rotation of the end effector 20 about the longitudinal axis A-A. In at least one non-limiting embodiment, the articulation nozzle 810 has a key 818 that extends into a corresponding elongated slot 951 in the proximal closure tube segment 950 and corresponding slot 859 in the spine segment 850 as shown in FIG. 49. Such arrangement facilitates the axial movement of the articulation nozzle 810 relative to the proximal closure tube segment 950 and spine segment 950 while also facilitating the rotation of the proximal closure tube segment 950 as a unit by rotating the nozzle 810 about the longitudinal axis A-A. As can also be seen in FIGS. 44 and 49, an actuator notch 817 is provided in the articulation nozzle 810 to engage the pivot plate 980. Thus, axial movement of the nozzle 810 will cause the pivot plate 980 to pivot about the actuation axis N-N.

To pivot the end effector in the left direction about the pivot point or articulation axis, the clinician moves the articulation nozzle 810 axially in the distal direction "DD". Such movement of the articulation nozzle 810 in the distal direction "DD" causes the pivot plate 980 to pivot about the actuation axis N-N in thereby moving the right articulation band 910 in the distal direction "DD" and pulling the left articulation band 930 in the proximal direction "PD". Such axial movement of the articulation nozzle 810 and the right and left articulation bands 910, 930 result in the application of a pushing motion to the boss 96 by the right articulation band 910 and a pulling motion to the boss 96 by the left articulation band assembly 930 which results in the articulation of the end effector. See FIG. 49. Likewise, to pivot the end effector about the pivot point or the articulation axis in the right direction, the clinician pulls the articulation nozzle 810 in the proximal direction "PD". Such movement of the nozzle 810 in the proximal direction "PD" causes the pivot plate 980 to pivot about the actuation axis N-N thereby pushing the left articulation band 930 in the distal direction "DD" and pulling the right articulation band 910 in the proximal direction "PD". Such axial movement of the articulation nozzle 810 and the right and left articulation bands 910, 930 result in the application of a pushing motion to the boss 96 by the left articulation band 930 and a pulling motion to the boss 96 by the right articulation band 910 which results in the articulation of the end effector to the right of the longitudinal axis A-A. To rotate the end effector about the longitudinal axis A-A, the clinician simply rotates the articulation nozzle 810 about the longitudinal axis A-A.

As was discussed above, the proximal closure tube segment 950 interfaces with the closure trigger, such that when the clinician actuates the closure trigger, the proximal closure tube segment 950 moves in the distal direction. In various non-limiting embodiments, the distal end portion of the proximal closure tube segment may be configured as shown, for example, in FIG. 2, to be pivotally coupled to the distal closure tube segment 150 to apply opening and closing motions to the anvil 130. In various non-limiting embodiments, the articulation locking system 1000 is configured to be locked when the proximal closure tube segment 950 is axially moved in the distal direction "DD" and be unlocked when the proximal closure tube segment 950 is axially moved in the proximal direction "PD".

Figure 45:
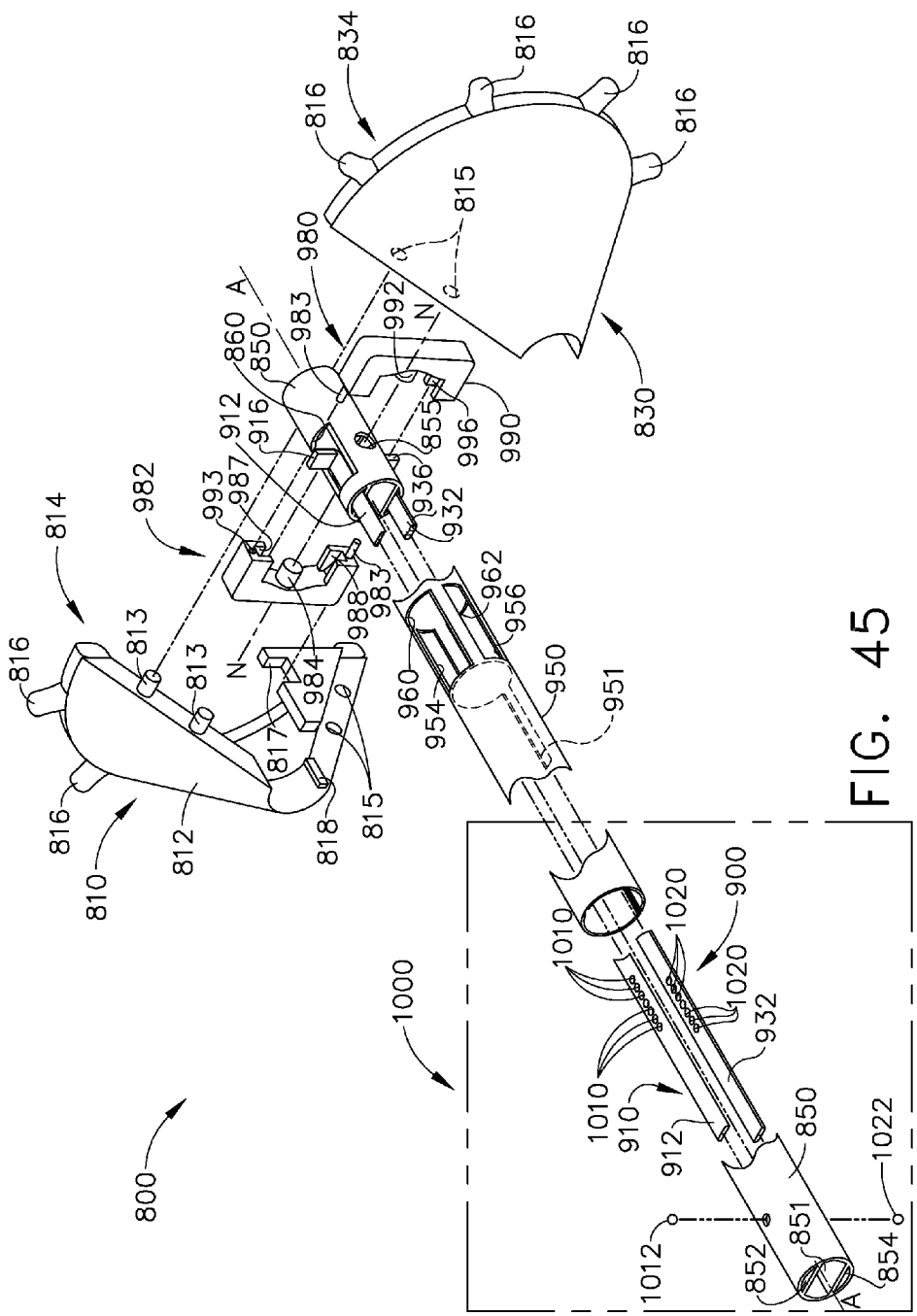
FIG. 45 is another exploded assembly view of the non-limiting articulation control system embodiment of FIGS. 43 and 44.
Figure 46:
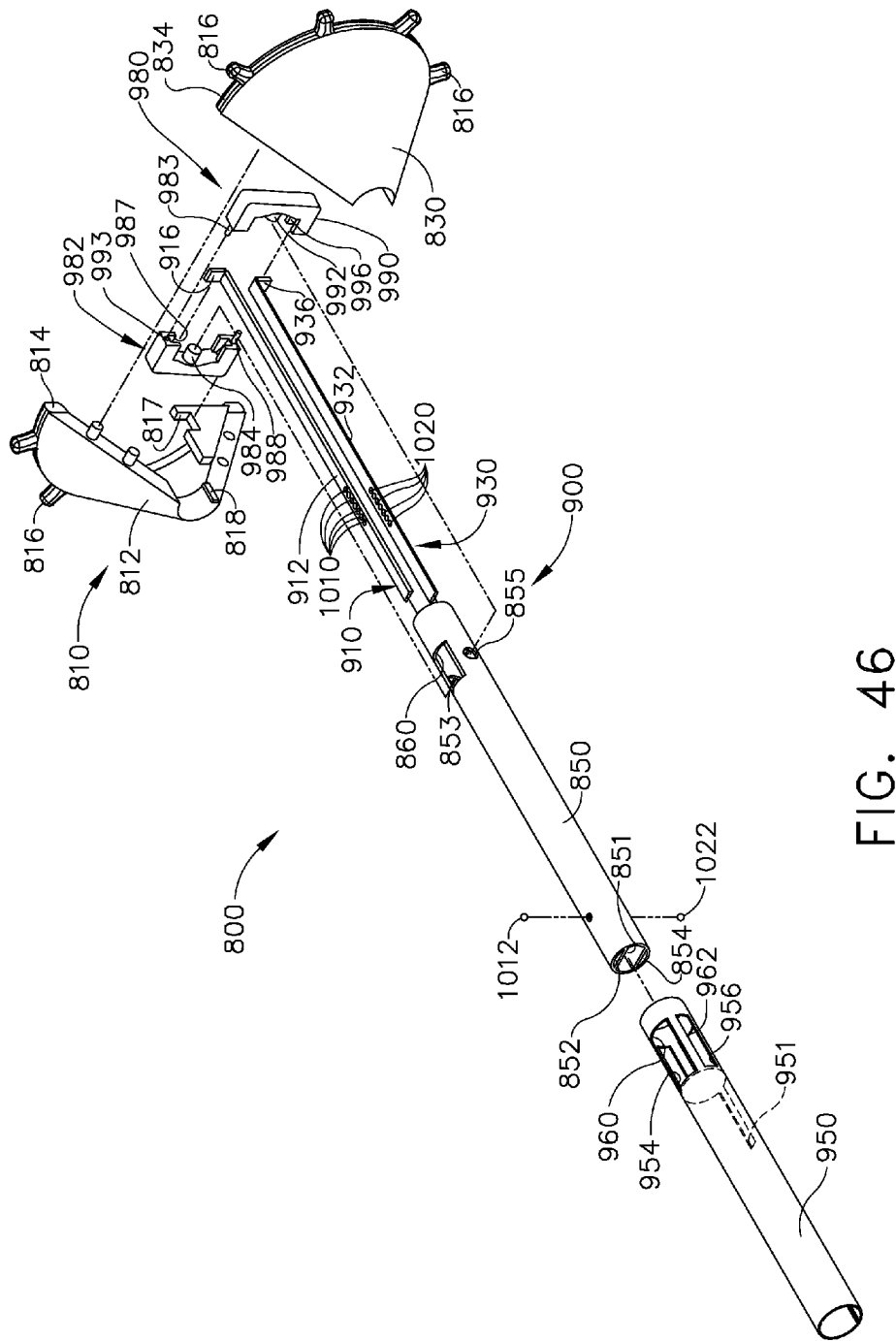
FIG. 46 is another exploded assembly view of the non-limiting articulation control system embodiment of FIGS. 43-45.

More specifically, as can be seen in FIG. 45, the right articulation band 910 has a plurality of right locking detents 1010 formed therein. Each detent 1010 corresponds to a particular angular or articulated orientation of the end effector about the articulation axis. The right locking detents 1010 are configured to be engaged by a right locking ball 1012 that is movably supported in a right locking hole 1014 in the spine segment 850. Similarly, the left articulation band 930 as a plurality of left locking detents 1020 formed therein that are configured to be engaged by a left locking ball 1022 that is movably supported in a left locking hole 1024 in the spine segment 850. See FIG. 49. The right locking ball 1012 is received in an elongated right locking cavity 1016 formed in the proximal closure tube segment 950. Such elongated locking cavity 1016 provides sufficient clearance for the right locking ball 1012 to move radially as the right articulation band 912 is moved axially within the spine segment 850. As can be most particularly seen in FIGS. 48 and 50, the proximal end 1017 of the elongated right locking cavity 1016 has a locking ramp 1018 formed thereon. Similarly, the left locking ball 1022 is received in an elongated left locking cavity 1026 formed in the proximal closure tube segment 950. Such elongated locking cavity 1026 provides sufficient clearance for the left locking ball 1022 to move radially as the left articulation band 932 is moved axially within the spine segment 850. As can be most particularly seen in FIG. 49, the proximal end of the elongated left locking cavity 1026 has a left locking ramp 1028 formed thereon.

Figure 48:
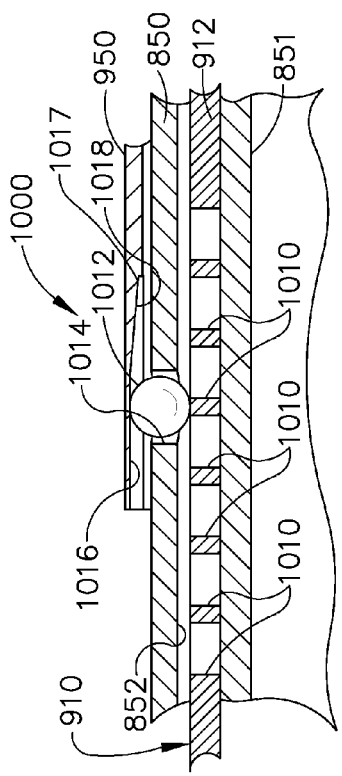
FIG. 48 is an enlarged cross-sectional view of a portion of the non-limiting articulation control system embodiment of FIGS. 43-47 in an unlocked position.

The operation of the articulation control system 800 and articulation locking system 1000 will now be described with reference to FIGS. 47-50. In various non-limiting embodiments, when the clinician desires to articulate the end effector about the articulation axis, the nozzle 810 is axially moved in a desired direction in the manner described above. The clinician may accomplish this action with the same hand that he or she is using to grasp and support the handle of the instrument. During the articulation process, the closure trigger has not been actuated and the proximal closure tube 950 is in the "open" position as shown in FIGS. 47 and 48. As the right articulation band 912 is moved axially, the right locking ball 1012 is permitted to move sufficiently radially away from the right articulation band 912 to permit it to move axially thereby and as the left articulation band 932 is moved axially, the left locking ball 1022 is permitted to move sufficiently radially away from the left articulation band 932 to permit it to move axially thereby. As the clinician advances the nozzle 810 in the appropriate axial direction and the right and left articulation bands 912, 932 move past the right and left locking balls 1012, 1022, respectively, the clinician receives tactile feedback as the locking detents 1010, 1020 movably engage the locking balls 1012, 1022, respectively. Once the clinician has attained the desired amount of articulation which corresponds to a position wherein the right locking ball 1012 engages a right locking detent 1010 that corresponds with that articulated position and the left locking ball 1022 likewise engages the left locking detent 1020 that corresponds with that articulated position, the clinician can then activate the closure trigger.

As discussed above, when the clinician activates the closure trigger, the proximal closure tube segment 950 is axially advanced in the distal direction "DD". As the proximal closure tube segment 950 is distally advanced, the right locking ramp 1018 engages the right locking ball 1012 and presses it radially inward into locking engagement with the corresponding right locking detent 1010. Likewise, the left locking ramp 1028 engages the left locking ball 1022 and presses it radially inward into locking engagement with the corresponding left locking detent 1020. Further axial advancement of the proximal closure tube segment 950 in the distal direction "DD" will continue to press the right and left locking balls 1012, 1022 into locking engagement to retain the end effector in the desired articulated position while the anvil is closed and the instrument is further used. After the end effector has been used "fired" and the closure trigger is unlocked an returned to the open position, the proximal closure tube segment 950 is moved in the proximal direction "PD" to the starting position wherein the articulation bands 912, 932 may be axially moved if desired to orient the end effector in the desired position for removal from the surgical site. Thus, such articulation locking system is essentially activated by the application of closing motions to the end effector. Although the articulation assembly as described above employs two elongated articulation rods or members, in alternative embodiments, only one elongated articulation member is employed. Likewise, in alternative embodiments, the articulation locking system may only employ one locking ball arrangement configured to engage locking detents in the corresponding elongated articulation member. Also, in embodiments that employ two elongated articulation members, only one locking ball may be employed to lock one of the articulation members upon application of a closure force to the end effector.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the inventions described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An articulatable surgical instrument, the instrument comprising:
    a shaft defining a longitudinal axis;
    an end effector coupled to said shaft for selective travel about an articulation axis that is substantially transverse to said longitudinal axis;
    a nozzle supported relative to said shaft such that said nozzle may be axially moved in first and second axial directions relative to said shaft and rotation of said nozzle about said longitudinal axis causes said shaft to rotate about said longitudinal axis without articulating the end effector about the longitudinal axis; and
    an articulation assembly operably interfacing with said end effector and said nozzle such that movement of said nozzle in said first axial direction causes said articulation assembly to apply a first articulation motion to said end effector to thereby cause said end effector to pivot about said articulation axis in a first articulation direction and movement of said nozzle in said second axial direction causes said articulation assembly to apply a second articulation motion to said end effector to thereby cause said end effector to pivot about said articulation axis in a second articulation direction.

2. The articulatable surgical instrument of claim 1 wherein said articulation assembly comprises:
    a first elongated articulation member having a first proximal end and a first distal end wherein the first distal end is operably coupled to said end effector and said first proximal end operably interfaces with said nozzle; and
    a second elongated articulation member having a second proximal end and a second distal end wherein the second distal end is operably coupled to said end effector and wherein said second proximal end operably interfaces with said nozzle.

3. The articulatable surgical instrument of claim 2 further comprising a pivot member operably supported for pivotal travel about an actuation axis that is substantially transverse to said longitudinal axis, said pivot member interacting with said first and second elongated articulation members and said nozzle such that movement of said nozzle in said first axial direction causes said first and second elongated articulation members to apply said first articulation motion to said end effector and wherein movement of said nozzle in said second axial direction causes said first and second elongated articulation members to apply said second articulation motion to said end effector.

4. The articulatable surgical instrument of claim 3 wherein said first elongated articulation member has a first pivot pin protruding therefrom and received within a corresponding first aperture in said pivot member and wherein said second elongated articulation member has a second pivot pin protruding therefrom and received within a corresponding second aperture in said pivot member.

5. The articulatable surgical instrument of claim 1 wherein said end effector comprises a surgical cutting and fastening instrument.

6. An articulatable surgical instrument, the instrument comprising:
    a shaft defining a longitudinal axis;
    an end effector coupled to said shaft for selective travel about an articulation axis that is substantially transverse to said longitudinal axis;
    a nozzle pivotally supported relative to said shaft such that said nozzle may be pivoted in first and second actuation directions relative to said shaft and rotation of said nozzle about said longitudinal axis causes said end effector to rotate about said longitudinal axis without articulating the end effector about the longitudinal axis; and
    an articulation assembly operably interfacing with said end effector and said nozzle such that movement of said nozzle in said first actuation direction causes said articulation assembly to apply a first articulation motion to said end effector to thereby cause said end effector to pivot about said articulation axis in a first articulation direction and movement of said nozzle in said second actuation direction causes said articulation assembly to apply a second articulation motion to said end effector to thereby cause said end effector to pivot about said articulation axis in a second articulation direction.

7. The articulatable surgical instrument of claim 6 wherein said articulation assembly comprises:
    a first elongated articulation member having a first proximal end and a first distal end wherein the first distal end is operably coupled to said end effector and said first proximal end operably interfaces with said nozzle; and
    a second elongated articulation member having a second proximal end and a second distal end wherein the second distal end is operably coupled to said end effector and wherein said second proximal end operably interfaces with said nozzle.

8. The articulatable surgical instrument of claim 7 wherein said first elongated articulation member has a first pivot pin received within a corresponding first aperture in said nozzle and wherein said second elongated articulation member has a second pivot pin received within a corresponding second aperture in said nozzle.

9. An articulatable surgical instrument, the instrument comprising:
    a shaft defining a longitudinal axis;
    an end effector coupled to said shaft for selective travel about an articulation axis that is substantially transverse to said longitudinal axis;
    a rotation nozzle coupled to said shaft such that rotation of said rotation nozzle causes said end effector to rotate about said longitudinal axis without articulating the end effector about the longitudinal axis;
    an articulation nozzle coaxially aligned with said rotation nozzle on said shaft and pivotally supported relative to said shaft such that said nozzle may be pivotally moved in first and second pivotal directions relative to said shaft; and an articulation assembly operably interfacing with said end effector and said articulation nozzle such that movement of said articulation nozzle in said first pivotal direction causes said articulation assembly to apply a first articulation motion to said end effector to thereby cause said end effector to pivot about said articulation axis in a first articulation direction and movement of said articulation nozzle in said second pivotal direction causes said articulation assembly to apply a second articulation motion to said end effector to thereby cause said end effector to pivot about said articulation axis in a second articulation direction.

10. The articulatable surgical instrument of claim 9 wherein said articulation assembly comprises:

a first elongated articulation member having a first proximal end and a first distal end wherein the first distal end is operably coupled to said end effector and said first proximal end operably interfaces with said articulation nozzle; and a second elongated articulation member having a second proximal end and a second distal end wherein the second distal end is operably coupled to said end effector and wherein said second proximal end operably interfaces with said articulation nozzle.

11. The articulatable surgical instrument of claim 10 wherein said first elongated articulation member has a first pivot pin received within a corresponding first aperture in said articulation nozzle and wherein said second elongated articulation member has a second pivot pin received within a corresponding second aperture in said articulation nozzle.

12. The articulatable surgical instrument of claim 9 wherein said end effector comprises a surgical cutting and fastening instrument.

13. An articulatable surgical instrument, the instrument comprising:

a shaft defining a longitudinal axis;

an end effector pivotally coupled to said shaft for selective pivotal travel about an articulation axis substantially transverse to said longitudinal axis;

a nozzle assembly comprising:
  a first nozzle segment movably supported on said shaft; and
  a second nozzle segment movably coupled to said first nozzle segment and movably supported on said shaft such that said first and second nozzle segments may be selectively moved on said shaft relative to each other and wherein said articulatable surgical instrument further comprises:

an articulation assembly operably interfacing with said end effector and said first and second nozzle segments such that movement of said first nozzle segment in a first axial direction causes said articulation assembly to apply a first articulation motion to said end effector to thereby cause said end effector to pivot about said articulation axis in a first articulation direction and movement of said second nozzle segment a second axial direction causes said articulation assembly to apply a second articulation motion to said end effector to thereby cause said end effector to pivot about said articulation axis in a second articulation direction.

14. The articulatable surgical instrument of claim 13 wherein said articulation assembly comprises:

a first elongated articulation member having a first proximal end and a first distal end wherein the first distal end is operably coupled to said end effector and said first proximal end operably interfaces with said first nozzle segment; and a second elongated articulation member having a second proximal end and a second distal end wherein the second distal end is operably coupled to said end effector and wherein said second proximal end operably interfaces with said second nozzle segment.

15. The articulatable surgical instrument of claim 13 wherein said end effector comprises a surgical cutting and fastening instrument.

16. An articulatable surgical instrument, comprising:

a shaft defining a longitudinal axis;

an end effector pivotally coupled to said shaft for selective pivotal travel about an articulation axis substantially transverse to said longitudinal axis;

an actuator pivotally supported relative to said shaft for selective pivotal travel about an actuation axis that is transverse to said longitudinal axis and comprising:
  a first actuator portion pivotally supported relative to said shaft and having a first actuator cam slot therein; and
  a second actuator portion pivotally supported relative to said shaft and having a second actuator cam slot therein and wherein said articulatable surgical instrument further comprises:
    a first elongated articulation member having a first proximal end and a first distal end wherein the first distal end is operably coupled to said end effector and said first proximal end has a first pivot pin extending therefrom into said first cam slot; and
    a second elongated articulation member having a second proximal end and a second distal end wherein the second distal end is operably coupled to said end effector and said second proximal end has a second pin extending therefrom into said second cam slot such that operation of said actuator in a first pivotal direction causes said first elongated articulation member to apply a first articulation motion to said end effector and operation of said actuator in a second pivotal direction causes said second elongated articulation member to apply a second articulation motion to said end effector.

17. The articulatable surgical instrument of claim 16 wherein said end effector comprises a surgical cutting and fastening instrument.

18. A method of operating a surgical instrument comprising:

grasping the articulatable surgical instrument of claim 1 in a single hand;

applying a first amount of force to the nozzle by a portion of the single hand to rotate the end effector about the longitudinal axis; and applying a second amount of force to the nozzle by a portion of the single hand to cause the end effector to pivot relative to the shaft.

19. A method of operating a surgical instrument comprising:

grasping the articulatable surgical instrument of claim 6 in a single hand;

applying a first amount of force to the nozzle by a portion of the single hand to rotate the end effector about the longitudinal axis;

applying a second amount of force to the nozzle by a portion of the single hand to cause the end effector to pivot relative to the shaft in the first articulation direction; and applying a third amount of force to the nozzle by a portion of the single hand to cause the end effector to pivot relative to the shaft in the second articulation direction.

20. A method of operating a surgical instrument comprising:
   grasping the articulatable surgical instrument of claim 9 in a single hand;
   applying a first amount of force to the rotation nozzle by a portion of the single hand to rotate the end effector about the longitudinal axis;
   applying a second amount of force to the articulation nozzle by a portion of the single hand to cause the end effector to pivot relative to the shaft in the first articulation direction; and
   applying a third amount of force to the articulation nozzle by a portion of the single hand to cause the end effector to pivot relative to the shaft in the second articulation direction.

21. A method of operating a surgical instrument comprising:
   grasping the articulatable surgical instrument of claim 13 in a single hand;
   applying a first amount of force to the nozzle assembly by a portion of the single hand to rotate the end effector about the longitudinal axis;
   applying a second amount of force to the first nozzle segment by a portion of the single hand to cause the end effector to pivot relative to the shaft in the first articulation direction; and
   applying a third amount of force to the second nozzle segment by a portion of the single hand to cause the end effector to pivot relative to the shaft in the second articulation direction.

22. A method of operating a surgical instrument comprising:
   grasping the articulatable surgical instrument of claim 16 in a single hand;
   applying a first amount of force to the actuator by a portion of the single hand to rotate the end effector about the longitudinal axis;
   applying a second amount of force to the first actuator portion by a portion of the single hand to cause the end effector to pivot relative to the shaft in the first pivotal direction; and
   applying a third amount of force to the second actuator portion by a portion of the single hand to cause the end effector to pivot relative to the shaft in the second pivotal direction.

* * * * *